(12) United States Patent
Ng et al.

(10) Patent No.: US 11,331,354 B2
(45) Date of Patent: May 17, 2022

(54) FECAL VIROME AND THERAPEUTIC EFFICACY OF FECAL MICROBIOTA TRANSPLANTATION

(71) Applicant: The Chinese University of Hong Kong, Hong Kong (CN)

(72) Inventors: Siew Chien Ng, Hong Kong (CN); Tao Zuo, Qingzhou (CN)

(73) Assignee: The Chinese University of Hong Kong, Hong Kong (CN)

( * ) Notice: Subject to any disclaimer, the term of this patent is extended or adjusted under 35 U.S.C. 154(b) by 502 days.

(21) Appl. No.: 16/292,907

(22) Filed: Mar. 5, 2019

(65) Prior Publication Data

US 2019/0321421 A1  Oct. 24, 2019

Related U.S. Application Data

(60) Provisional application No. 62/660,780, filed on Apr. 20, 2018.

(51) Int. Cl.
| | |
|---|---|
| *A61K 35/76* | (2015.01) |
| *C12Q 1/70* | (2006.01) |
| *C12Q 1/6888* | (2018.01) |
| *G16H 50/30* | (2018.01) |
| *C12Q 1/6869* | (2018.01) |

(52) U.S. Cl.
CPC ............ *A61K 35/76* (2013.01); *C12Q 1/6869* (2013.01); *C12Q 1/6888* (2013.01); *C12Q 1/70* (2013.01); *G16H 50/30* (2018.01); *C12Q 2600/106* (2013.01)

(58) Field of Classification Search
None
See application file for complete search history.

(56) References Cited

PUBLICATIONS

Conceio-Neto, Nadia, et al. "Low eukaryotic viral richness is associated with faecal microbiota transplantation success in patients with UC." Gut 67.8 (2018): 1558-1559. (Year: 2017).*
Zuo, Tao, et al. "Bacteriophage transfer during faecal microbiota transplantation in Clostridium difficile infection is associated with treatment outcome." Gut 67.4 (2018): 634-643. (Year: 2017).*
Barr, et al. "Bacteriophage adhering to mucus provide a non-host-derived immunity." Proceedings of the National Academy of Sciences 110, No. 26 (2013) 10771-10776.
Bouwknegt et al., "Burden of Clostridium Difficile Infection in the United States," Letters to the Editor, New England Journal of Medicine, 372;24 Jun. 11, 2015, 2368.
Broecker, et al. "Long-term changes of bacterial and viral compositions in the intestine of a recovered Clostridium difficile patient after fecal microbiota transplantation." Molecular Case Studies 2, No. 1 (2016): a000448.
Broecker, et al. "Stable core virome despite variable microbiome after fecal transfer." Gut Microbes 8, No. 3 (2017): 214-220.
Broecker, et al. "Long-term microbiota and virome in a Zurich patient after fecal transplantation against Clostridium difficile infection." Annals of the New York Academy of Sciences 1372, No. 1 (2016): 29-41.
Bryson, et al.. "A novel sister clade to the enterobacteria microviruses (family M icroviridae) identified in methane seep sediments." Environmental microbiology 17, No. 10 (2015): 3708-3721.
Cadweli, "The virome in host health and disease." Immunity 42, No. 5 (2015) 805-813.
Chehoud, et al. "Transfer of viral communities between human individuals during fecal microbiota transplantation." MBio 7, No. 2 (2016): e00322-16.
Colman, et al. "Fecal microbiota transplantation as therapy for inflammatory bowel disease: a systematic review and meta-analysis." Journal of Crohn's and Colitis 8, No. 12 (2014): 1569-1581.
Cortez, et al. "Coevolution can reverse predator-prey cycles." Proceedings of the National Academy of Sciences 111, No. 20 (2014): 7486-7491.
Delcher, et al. "Identifying bacterial genes and endosymbiont DNA with Glimmer." Bioinformatics 23, No. 6 (2007): 673-679.
De Leon, et al. "Transient flare of ulcerative colitis after fecal microbiota transplantation for recurrent Clostridium difficile infection." Clinical Gastroenterology and Hepatology 11, No. 8 (2013): 1036-1038.
Drekonja, etal. "Fecal microbiota transplantation for Clostridium difficile infection: a systematic review." Annals of internal medicine 162, No. 9 (2015): 630-638.
Duerkop, et al. "A composite bacteriophage alters colonization by an intestinal commensal bacterium." Proceedings of the National Academy of Sciences 109, No. 43 (2012): 17621-17626.
Fu, et al. "CD-HIT: accelerated for clustering the next-generation sequencing data." Bioinformatics 28, No. 23 (2012): 3150-3152.
Hannigan, et al. "The human skin double-stranded DNA virome: topographical and temporal diversity, genetic enrichment, and dynamic associations with the host microbiome." MBio 6, No. 5 (2015): e01578-15.
Kelly, et al. "Update on fecal microbiota transplantation 2015: indications, methodologies, mechanisms, and outlook." Gastroenterology 149, No. 1 (2015): 223-237.
Khoruts, et al. "Changes in the composition of the human fecal microbiome after bacteriotherapy for recurrent Clostridium difficile-associated diarrhea." Journal of clinical gastroenterology 44, No. 5 (2010): 354-360.
Khoruts, et al. "Therapeutic transplantation of the distal gut microbiota." Mucosal immunology 4, No. 1 (2011): 4.
Langmead, et al. "Fast gapped-read alignment with Bowtie 2." Nature methods 9, No. 4 (2012): 357.

(Continued)

*Primary Examiner* — Robert J Yamasaki
(74) *Attorney, Agent, or Firm* — Kilpatrick Townsend & Stockton LLP

(57) ABSTRACT

The present invention resides in the discovery that abundance and diversity of viral species in the fecal matter from a donor used in fecal microbiota transplantation (FMT) treatment can influence the outcome of the FMT treatment. Thus, novel methods are provided for identifying subjects as suitable donors for FMT, for assessing the likelihood of FMT treatment success, and for enhancing FMT treatment efficacy. Also provided are kits and compositions for FMT with enhanced efficacy.

14 Claims, 36 Drawing Sheets
(36 of 36 Drawing Sheet(s) Filed in Color)

(56) References Cited

PUBLICATIONS

Lee, et al. "Frozen vs fresh fecal microbiota transplantation and clinical resolution of diarrhea in patients with recurrent Clostridium difficile infection: a randomized clinical trial." Jama 315, No. 2 (2016): 142-149.

Lim, et al. "Early life dynamics of the human gut virome and bacterial microbiome in infants." Nature medicine 21, No. 10 (2015): 1228.

Manichanh, et al. "Reshaping the gut microbiome with bacterial transplantation and antibiotic intake." Genome research 20, No. 10 (2010): 1411-1419.

McDonald, et al. "An improved Greengenes taxonomy with explicit ranks for ecological and evolutionary analyses of bacteria and archaea." The ISME journal 6, No. 3 (2012): 610.

Minot, et al. "Rapid evolution of the human gut virome." Proceedings of the National Academy of Sciences 110, No. 30 (2013): 12450-12455.

Norman, et al. "Disease-specific alterations in the enteric virome in inflammatory bowel disease." Cell 160, No. 3 (2015): 447-460.

Ott, et al. "Efficacy of sterile fecal filtrate transfer for treating patients with Clostridium difficile infection." Gastroenterology 152, No. 4 (2017): 799-811.

Peng, et al. "IDBA—a practical iterative de Bruijn graph de novo assembler." In Annual international conference on research in computational molecular biology, pp. 426-440. Springer, Berlin, Heidelberg, 2010.

Rea, et al. "Effect of broad-and narrow-spectrum antimicrobials on Clostridium difficile and microbial diversity in a model of the distal colon." Proceedings of the National Academy of Sciences 108, No. Supplement 1 (2011): 4639-4644.

Reyes, et al. "Gnotobiotic mouse model of phage-bacterial host dynamics in the human gut." Proceedings of the National Academy of Sciences 110, No. 50 (2013) 20236-20241.

Reyes, et al. "Viruses in the faecal microbiota of monozygotic twins and their mothers." Nature 466, No. 7304 (2010): 334.

Rodriguez-Valera, et al. "Explaining microbial population genomics through phage predation." Nature Reviews Microbiology 7, No. 11 (2009): 828.

Schloss, et al. "Introducing mothur: open-source, platform-independent, community-supported software for describing and comparing microbial communities." Appl. Environ. Microbiol. 75, No. 23 (2009): 7537-7541.

Schmieder, et al. "Fast identification and removal of sequence contamination from genomic and metagenomic datasets." PloS one 6, No. 3 (2011): e17288.

Thingstad, "Elements of a theory for the mechanisms controlling abundance, diversity, and biogeochemical role of lytic bacterial viruses in aquatic systems." Limnology and Oceanography 45, No. 6 (2000): 1320-1328.

Van Nood, et al. "Duodenal infusion of donor feces for recurrent Clostridium difficile." New England Journal of Medicine 368, No. 5 (2013): 407-415.

Yang, et al. "Enteric viruses ameliorate gut inflammation via toll-like receptor 3 and toll-like receptor 7-mediated interferon-β production." Immunity 44, No. 4 (2016): 889-900.

\* cited by examiner

FIGURE 6

FECAL VIROME AND THERAPEUTIC EFFICACY OF FECAL MICROBIOTA TRANSPLANTATION

This application claims priority to U.S. Provisional Patent Application No. 62/660,780, filed Apr. 20, 2018, the contents of which are hereby incorporated by reference in the entirety for all purposes.

BACKGROUND OF THE INVENTION

*Clostridium difficile* infection (CDI) is a symptomatic infection due to the spore-forming bacterium, *Clostridium difficile*. *C. difficile* infection is spread by bacterial spores found within feces. Risk factors for infection include antibiotic or proton pump inhibitors use, hospitalization, other health problems, and older age. Its symptoms including watery diarrhea, fever, nausea, and abdominal pain, CDI makes up about 20% of cases of antibiotic-associated diarrhea. About 453,000 cases *C. difficile* infection occurred in the United States in 2011, resulting in 29,000 deaths. Each year, *C. difficile* infections accounts for health care cost of approximately $1.5 billion. Globally, rates of *C. difficile* infection have increased between 2001 and 2016, typically with more women than men affected by the infections.

Fecal microbiota transplantation (FMT) is highly effective for the treatment of CDI, especially among patients suffering from recurrent CDI. Also known as stool transplant, FMT involves a process of transplanting fecal matter containing fecal microorganism from a healthy individual into the gastrointestinal tract of a recipient. The goal of FMT is restoration of the colonic microflora disrupted due to CDI by introducing (or re-introducing) healthy bacterial flora via various means of infusion of a healthy individual's stool, e.g., by colonoscopy, enema, orogastric tube, or by mouth in the form of a capsule containing freeze-dried material obtained from a healthy donor. Aside from CDI, FMT is increasingly being used to treat other intestinal and extra-intestinal diseases, including other gastrointestinal diseases, such as ulcerative colitis, Crohn's disease, constipation, irritable bowel syndrome, obesity, diabetes, metabolic syndrome, intestinal graft versus host disease, hepatic encephalopathy, colorectal cancer, and the like. In addition, FMT has been used for treating certain neurological conditions, such as multiple sclerosis, autism, and Parkinson's disease, as well diseases associated with antibiotic-resistant enterococci. Considering the prevalence of CDI and other conditions treatable by FMT in the human population and their significant economic implications, there exists an urgent need for developing new and improved methods for treating CDI and other disorders by FMT with enhanced efficacy. The present invention fulfills this and other related needs.

BRIEF SUMMARY OF THE INVENTION

The invention relates to novel methods and compositions useful for more effectively treating *Clostridium difficile* infection (CDI) and other diseases suitable by fecal microbiota transplantation (FMT) treatment. In particular, the present inventors discovered that CDI patients typically have an elevated level of Caudovirales in their gut and stool, whereas the bacteriophage richness and diversity within the Caudovirales taxa tends to be lower. Upon a successful FMT, the patients typically have an increased level of Caudovirales richness and diversity (which may be expressed in Chao1 richness index and Shannon's diversity index, respectively), with more bacteriophage species derived from the donor. This finding allows the inventors to devise methods and compositions that can improve FMT effectiveness. Thus, in the first aspect, the present invention provides a novel method for assessing the likelihood of effective FMT. The method includes a step of determining Caudovirales richness or Caudovirales diversity in a stool sample obtained from a potential donor prior to FMT is performed, i.e., before fecal material is obtained from a donor and processed to be transplanted into a recipient in need of FMT. In some embodiments, when Caudovirales richness (Chao1 richness index) is found to be greater than 400, FMT is assessed as likely to be effective for a potential recipient. In some embodiments, when Caudovirales diversity (Shannon's diversity index) is found to be greater than 4, FMT is assessed as likely to be effective for a potential recipient. When a conclusion of effective FMT is reached, the method further includes the step of performing FMT on the potential recipient. In some embodiments, when Caudovirales richness (Chao1 richness index) is no greater than 400, FMT is assessed as unlikely to be effective for a potential recipient. In some embodiments, when Caudovirales diversity (Shannon's diversity inde) is no greater than 4, FMT is assessed as unlikely to be effective for a potential recipient. Upon reaching the conclusion that the proposed FMT is assessed to be unlikely to be effective, the procedure may not be performed.

In some embodiments, this method further includes a step of determining Caudovirales richness or diversity in a stool sample obtained from a potential recipient prior to FMT. The potential recipient's Caudovirales richness or diversity can then be compared with the donor's Caudovirales richness or diversity: when the donor's Caudovirales richness is greater than the potential recipient's Caudovirales richness, the proposed FMT is assessed as likely to be effective for the potential recipient. In some cases, when the donor's Caudovirales diversity is greater than the potential recipient's Caudovirales diversity, the proposed FMT is assessed as likely to be effective for the potential recipient. In some examples, the proposed FMT is assessed as likely to be effective for the potential recipient when the donor's Caudovirales richness is substantially greater than the potential recipient's Caudovirales richness, e.g., by at least 10%, 20%, 25%, 30%, 40%, 50%, 75%, 80%, 100%, or even higher. Similarly, the proposed FMT is assessed as likely to be effective for the potential recipient when the donor's Caudovirales diversity is substantially greater than the potential recipient's Caudovirales diversity, e.g., by at least 10%, 20%, 25%, 30%, 40%, 50%, 75%, 80%, 100%, or even higher. Upon reaching the conclusion that the proposed FMT is likely to be effective, the method is often practiced with an additional step of performing the FMT procedure on the potential recipient. Conversely, if the donor's Caudovirales richness is no greater than the potential recipient's Caudovirales richness, the proposed FMT is assessed as unlikely to be effective for the potential recipient and thus may not be performed. In some embodiments, when the FMT procedure is performed, the claimed method may in addition include a step of determining Caudovirales richness or Caudovirales diversity in a stool sample obtained from the recipient after the recipient has already undergone the FMT procedure.

In some embodiments, more than one potential FMT donor is tested to determine the potential donor's appropriateness based on the level of Caudovirales richness or Caudovirales diversity in the potential donor's stool. For example, Caudovirales richness or diversity is determined in a first stool sample obtained from a first potential donor prior to FMT and in a second stool sample obtained from a second potential donor prior to FMT. If the first potential donor has a lower Caudovirales richness or diversity value than the second potential donor, the first potential donor is assessed to have a lower likelihood of being an appropriate donor for an effective FMT than the second potential donor, then the second donor may provide his fecal material for processing before being used in FMT. On the other hand, if a first donor has a higher Caudovirales richness or diversity value than that of other donors being tested, the first donor's fecal material is deemed of better quality for processing to make transplant material for FMT. In some cases, the first donor's fecal material may be taken for further processing, either alone or pooled with fecal material from other potential donors, before being used in FMT. In some cases, Caudovirales richness or Caudovirales diversity is determined by quantitative polymerase chain reaction (PCR) or metagenomics sequencing.

In a second aspect, the present invention provides a novel and improved method for identifying a suitable donor who would provide stool or fecal material for use in FMT. The method includes the step of determining Caudovirales richness or diversity in a stool sample obtained from a candidate who is being considered as a potential donor for FMT. In some embodiments, when Caudovirales richness (Chao1 richness index) is found to be greater than 400, the candidate is identified as a suitable donor for FMT; or when Caudovirales diversity (Shannon's diversity index) is found to be greater than 4, the candidate is identified as a suitable donor for FMT. In some embodiments, when Caudovirales richness (Chao1 richness index) is no greater than 400, and the candidate is identified as an unsuitable donor for FMT; or when Caudovirales diversity (Shannon's diversity index) is no greater than 4, the candidate is identified as an unsuitable donor for FMT. In some embodiments, the method further includes a step of obtaining fecal matter from the candidate or a step of processing the fecal matter from the candidate for use in FMT. In some embodiments, the method further includes a step of combining fecal matter from the candidate with fecal matter obtained from one or more other donors (whose Caudovirales richness or diversity value may or may not be as desirable for FMT as that of the candidate) such that the combined fecal material can be processed for use in FMT. In some embodiments, Caudovirales richness or diversity is determined by quantitative polymerase chain reaction (PCR) or metagenomics sequencing.

In a third aspect, the present invention provides kits and compositions useful for enhanced FMT treatment with improved efficacy. In some embodiments, the kit comprises (1) a first composition comprising donor stool; and (2) a second composition comprising one or more reagents for determining Caudovirales richness or diversity. In some embodiments, the first composition comprises donor stool that has been dried, frozen, and placed in a capsule for oral ingestion. In some embodiments, the one or more reagents comprise reagents for a quantitative polymerase chain reaction (PCR) or metagenomics sequencing, such as primers, a DNA polymerase (especially a thermal stable DNA polymerase), dNTPs, and the like for a PCR. In some embodiments, the kit may further comprise printed user instructions.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

(FIG. 1A) Comparison of the relative abundance of enteric viruses in CDI subjects and healthy controls at the order level. The bars indicate the median and IQR. Statistical significance was determined by Mann-Whitney test. $*p<0.05$. Comparison of Caudovirales diversity (FIG. 1B), richness (FIG. 1C) and evenness (FIG. 1D) between CDI subjects and healthy controls at the species level. Statistical significance was determined by Mann-Whitney test. $*p<0.05$. (E) Relative abundance of viruses at the family level. Statistical significance was determined by LEfSe analysis with FDR correction comparing all samples with all samples. $*q<0.05$. (FIG. 1F) Spearman correlation plots of the virus orders Caudovirales, Microvirida and Anelloviridae in CDI subjects and controls. Statistical significance was determined for all pairwise comparisons; those with values of $p<0.05$ are shown. Positive values (blue circles) indicate positive correlations, and negative values (red circles) indicate inverse correlations. The size and shading of the circle indicate the magnitude of the correlation, whereby darker shades are more correlated than lighter shades.

(FIG. 2A) Relative abundance of Caudovirales, Microviridae, and Anelloviridae in pre-FMT samples and post-FMT samples collected at the last follow-up. Statistical significance was determined by paired Wilcoxon sign permutation test, $*p<0.05$. (FIG. 2B) Alterations in the relative abundance of viral species in the stool of *Clostridium difficile* infection subjects after FMT at different time points until the last follow-up. 'F' indicates FMT-treated subject. 'D' indicates FMT donor. 'W' indicates weeks post treatment.

(FIG. 3C) Presence-absence heat map of Caudovirales contigs in the stool samples of CDI subjects and their corresponding donors. Only contigs with reads per kilobase per million >1 were shown. 'D' indicates FMT donor; 'R' indicates FMT recipient. 'Donor>recipient' indicates the Caudovirales richness in stool samples of donor were higher than that of the recipient. 'Responder' indicates CDI subjects who responded to FMT; 'non-responders' indicates CDI subjects who had disease recurrence after FMT.

(FIG. 4A) Presence-absence heat map of Caudovirales contigs in pre-FMT and post-FMT collected at the last follow-up for nine FMT recipients. Only contigs with reads per kilobase per million >3 were shown to assure the colonisation of donor-derived contigs. Red lines indicate contigs transferred from the donor. (FIG. 4B) Percentage of donor-transferred Caudovirales contigs in FMT recipients at the last follow-up. The size of the circle indicates the count of Caudovirales contigs transferred from donor. The colour of the circle indicates the richness of Caudovirales in the recipient relating to the treatment response. (FIG. 4C) Comparison of the frequency of donor-derived Caudovirales contigs in FMT responders and in non-responders. Statistical significance was determined by Mann-Whitney test. $*p<0.05$. (FIG. 4D) Presence of bacterial operational taxonomic unit (OTUs) in FMT recipients at the last follow-up. The colour of the bar indicates the origin of the bacterial OTUs. Purple indicates donor-derived OTUs colonised in the recipient, orange indicates OTUs exclusively present in recipient but not in the donor, while green indicates OTUs present both in donor and in recipient. (FIG. 4E) Comparison of the frequency of donor-derived bacterial OTUs in FMT responders and in non-responders. Statistical significance was determined by Mann-Whitney test.

(FIG. 5B) The correlation of bacteria richness with Caudovirales diversity and bacteria diversity with Caudovirales diversity before and after faecal microbiota transplantation (FMT). (FIG. 5C) Bacteria-Caudovirales correlation pattern during FMT treatment. Spearman correlation plots of the relative abundances of Caudovirales species and bacterial families identified to be significantly associated with CDI and controls, in donor, pre-FMT and post-FMT samples. Statistical significance was determined for all pairwise comparisons; significant correlations (p<0.05) are displayed with asterisk. Blue circles and positive values indicate positive correlations, and red circles and negative values indicate inverse correlations. The size and shading indicate the magnitude of the correlation, where darker shades are more correlated than lighter ones.

FIG. 6 Longitudinal timeline of stool sample collection (expressed in weeks). "F" indicates FMT treated subject. "D" indicates FMT donor. "S" indicates subject treated with standard therapy (STD, vancomycin). "W" indicates weeks post treatment. Red dots indicate donor samples, green dots indicate FMT recipient samples sampled at different time points.

(FIG. 7B) Rarefaction curves of Caudovirales richness, at the species level, versus an increasing number of subsamplings with replacement. (FIG. 7C) Microviridae species diversity in CDI and controls. Statistical significance was determined by Mann-Whitney test. *P<0.05.

(FIG. 8B) Relative abundances of Caudovirales, Microviridae and Anellovirdae in NI and healthy controls. Statistical significance was determined by Mann-Whitney test. *P<0.05. NI, patients with norovirus infection.

(FIG. 10B) Present ratio of Caudovirales contigs in FMT recipients across the follow-up time period of post FMT. The color of the bar indicates the origin of the Caudovirales contigs. Purple indicates donor-derived contigs colonized in the recipient, orange indicates contigs exclusively present in the recipient but not in the donor, while green indicates contigs present both in donor and in recipient.

(FIG. 11B) Heatmap of the abundance of differentially presented bacterial families in donor, pre-FMT and post-FMT last follow-up samples. Bacterial families with significant changes post FMT are labeled with asterisk. (FIG. 11C) Plots of bacterial Shannon diversity (top) and Chao1 richness (bottom) in the follow-up stool samples of FMT recipients and their corresponding donor.

(FIG. 12B) Donor-to-recipient ratios of the relative abundance of each Caudovirales species as calculated as the relative abundance of Caudovirales species in donor divided by the relative abundance of Caudovirales species in recipient before FMT.

(FIG. 13A) Diversity (Shannon) and richness (Chao1) alterations of the Caudovirales virome and bacterial microbiome in stool samples of CDI patients after vancomycin treatment (STD) up to last follow-up. "S" indicates subject treated with vancomycin (standard therapy, STD). "W" indicates weeks post treatment. (FIG. 13B) Spearman correlation plots of bacteria-Caudovirales relationship pattern across vancomycin treatment (STD) and FMT follow-up samples respectively. Statistical significance was determined for all pairwise comparisons, significant correlations (P value <0.05) are displayed with asterisk. Blue circles and positive values indicate positive correlations, red circles and negative values indicate inverse correlations. The size and shading indicate the magnitude of the correlation where darker shades are more correlated than lighter ones. (FIG. 13C) Virome community structure changes over the course of vancomycin at the family level. (FIG. 13D) Change in the relative abundance of Caudovirales and Microviridae after treatment with FMT and vancomycin (STD). Statistical significance was determined by Mann-Whitney test. *P<0.05.

DEFINITIONS

Figure 1A:
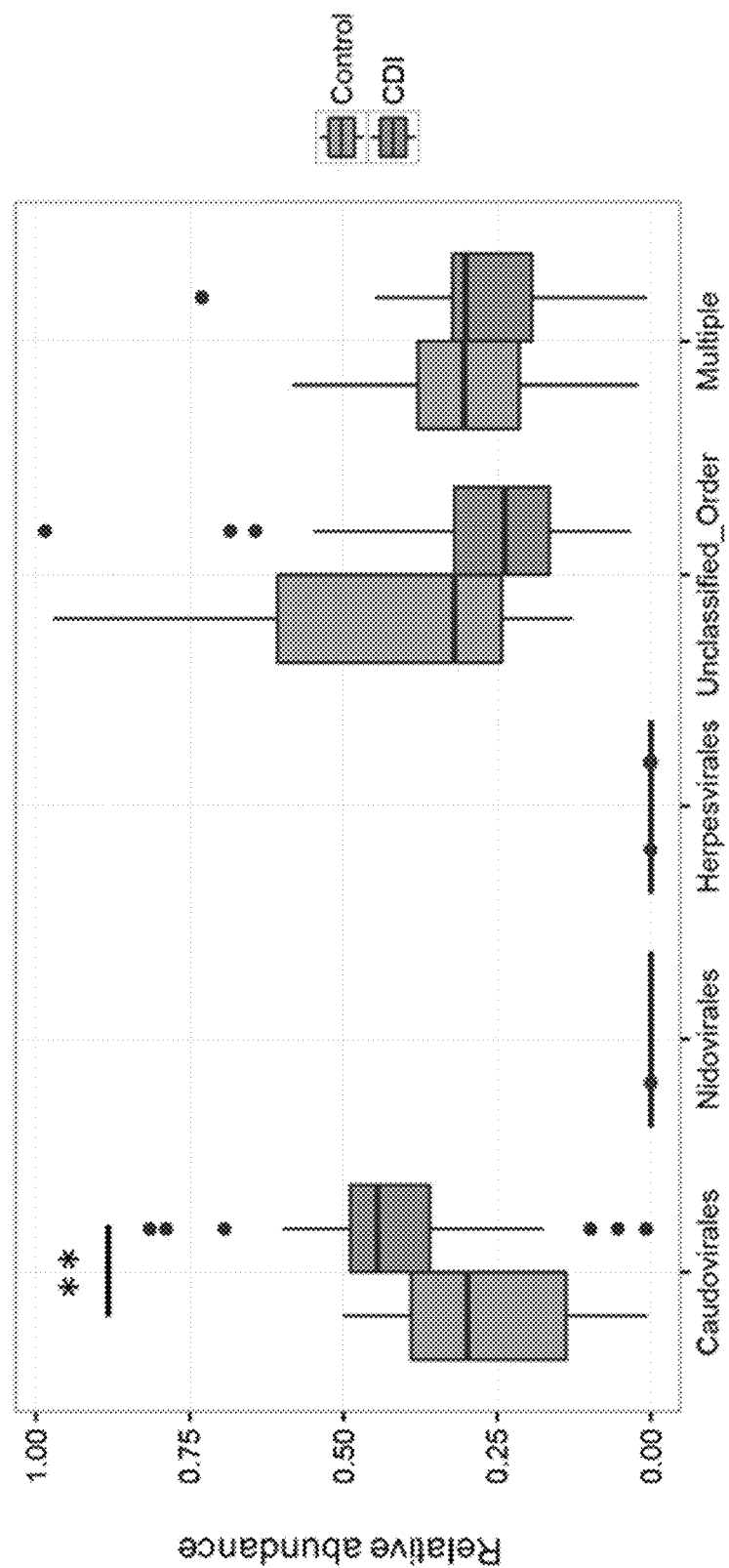
FIGS. 1A-1F Virome alterations in *Clostridium difficile* infection (CDI).
Figure 1D:
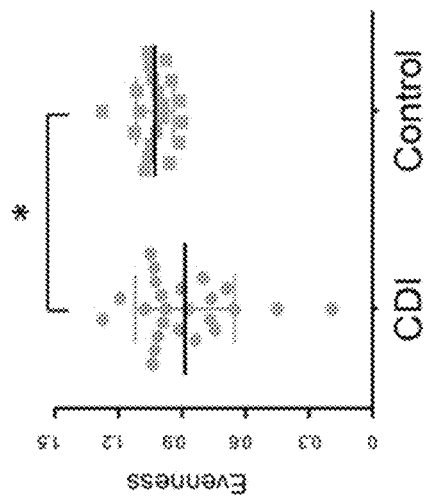

The term "fecal microbiota transplantation (FMT)" or "stool transplant" refers to a medical procedure during which fecal matter containing live fecal microorganisms (bacteria, fungi, and the like) obtained from a healthy individual is transferred into the gastrointestinal tract of a recipient to restore healthy gut microflora that has been disrupted or destroyed by a variety of medical conditions. Typically, the fecal matter from a healthy donor is first processed into an appropriate form for the transplantation, which can be made through direct deposit into the lower gastrointestinal tract such as by colonoscopy, or by nasal intubation, or through oral ingestion of an encapsulated material containing dried and frozen fecal matter. *Clostridium difficile* infection (CDI) is the condition most commonly treated by FMT, although a number of other diseases and disorders including in the digestive system and in the nervous system have been reported to be successfully treated by FMT.

The term "inhibiting" or "inhibition," as used herein, refers to any detectable negative effect on a target biological process, such as RNA/protein expression of a target gene, the biological activity of a target protein, cellular signal transduction, cell proliferation, and the like. Typically, an inhibition is reflected in a decrease of at least 10%, 20%, 30%, 40%, 50%, 60%, 70%, 80%, 90% or greater in the target process (e.g., growth or proliferation of bacteriophage), or any one of the downstream parameters mentioned above, when compared to a control. "Inhibition" further includes a 100% reduction, i.e., a complete elimination, prevention, or abolition of a target biological process or signal. The other relative terms such as "suppressing," "suppression," "reducing," and "reduction" are used in a similar fashion in this disclosure to refer to decreases to different levels (e.g., at least 10%, 20%, 30%, 40%, 50%, 60%, 70%, 80%, 90% or greater decrease compared to a control level) up to complete elimination of a target biological process or signal. On the other hand, terms such as "activate," "activating," "activation," "increase," "increasing," "promote," "promoting," "enhance," "enhancing," or "enhancement" are used in this disclosure to encompass positive changes at different levels (e.g., at least 10%, 20%, 30%, 40%, 50%, 60%, 70%, 80%, 90%, 100%, 200%, or greater such as 3, 5, 8, 10, 20-fold increase compared to a control level) in a target process or signal.

As used herein, "Caudovirales" refers to an order of viruses also known as the tailed bacteriophages. These tailed bacteriophages are believed to have a common origin, due to their characteristic structure and possession of potentially homologous genes. The order of Caudovirales comprises three families. The Caudovirales are group I viruses having double-stranded DNA (dsDNA) genomes ranging from 18,000 base pairs to 500,000 base pairs in length. The viral particles of Caudovirales have a distinct shape; each virion has an icosohedral head that contains the viral genome, and is attached to a flexible tail by a connector protein. The order encompasses a wide range of viruses, many of which containing genes of similar nucleotide sequence and function. Some tailed bacteriophage genomes can vary quite significantly in nucleotide sequence, however, even among the same genus. Different bacteriophage species within the order of Caudovirales can be distinguished from one another by sequencing date generated from distinct contigs and/or their signature 16S rDNA.

"Diversity" is a term of art in the microbiome research field. The diversity of microbes within a given body habitat, such as the gut and feces, is defined as the number and abundance of distinct types of organisms present in a sample. Diversity can be measured and expressed as Shannon's diversity index and Simpson's diversity index, etc., which are quantitative measures that reflect how many different types of biological entities (such as species) present in a dataset (a community) while simultaneously taking into account how evenly the basic entities are distributed among those types. "Caudovirales diversity" is a term defined as the number and abundance of distinct viral organisms or species within the order Caudovirales. For instance, the relative abundance of each bacteriophage can be determined by comparing the quantity of DNA (contig) specific within the order of Caudovirales in one given sample with the quantity of all bacteriophage DNA belonging to the order of Caudovirales in the same sample. Diversity can be determined using various polynucleotide sequence-based techniques such as metagenomic sequencing and polymerase chain reaction (PCR), especially quantitative PCR.

"Richness" is another term of art frequently used in the microbiome research field. The richness of microbes within a given body habitat, such as the gut and feces, is defined as the number of distinct types of organisms (species) present in a sample. Richness can be measured and expressed as Chao1 richness index, etc., quantitative measures that reflect how many different types of biological entities (such as species) there are in a dataset (a community). "Caudovirales richness" is defined as the number of distinct viral organisms/species within the order Caudovirales. For instance, Caudovirales richness can be determined by enumerating the quantity of species or their representative DNA (contig) within a particular bacteriophage taxon, such as the order of Caudovirales. Richness can be determined by metagenomic sequencing or quantitative PCR.

The term "effective amount," as used herein, refers to an amount of a substance that produces a desired effect (e.g., an inhibitory or suppressive effect on any one particular bacteriophage species within the Caudovirales order) for which the substance (e.g., an antiviral agent) is used or administered. The effects include the prevention, inhibition, or delaying of any pertinent biological process during the bacteriophage species of the Caudovirales order growth or development to any detectable extent. The exact amount will depend on the nature of the substance (the active agent), the manner of use/administration, and the purpose of the application, and will be ascertainable by one skilled in the art using known techniques as well as those described herein.

As used herein, the term "about" denotes a range of value that includes +/−10% of a specified value. For instance, "about 10" denotes the value range of 10+/−10×10%, i.e., 9 to 11.

DETAILED DESCRIPTION OF THE INVENTION

I. Introduction

Fecal microbiota transplantation (FMT) is effective for the treatment of recurrent *Clostridium difficile* infection (CDI). Studies have shown bacterial colonisation after FMT, but data on viral alterations in CDI are scarce. In this study, the present inventors investigated enteric virome alterations in CDI and the association between viral transfer and clinical outcome in patients with CDI. Design Ultra-deep metagenomic sequencing of virus-like particle preparations and bacterial 16S rRNA sequencing were performed on stool samples from 24 subjects with CDI and 20 healthy controls. The virome and bacterial microbiome changes were longitudinally assessed in nine CDI subjects treated with FMT and five treated with vancomycin. Enteric virome alterations were assessed in association with treatment response. Subjects with CDI demonstrated a significantly higher abundance of bacteriophage Caudovirales and a lower Caudovirales diversity, richness and evenness compared with healthy household controls. Significant correlations were observed between bacterial families Proteobacteria, Actinobacteria and Caudovirales taxa in CDI. FMT treatment resulted in a significant decrease in the abundance of Caudovirales in CDI. Cure after FMT was observed when donor-derived Caudovirales contigs occupied a larger fraction of the enteric virome in the recipients (p=0.024). In treatment responders, FMT was associated with alterations in the virome and the bacterial microbiome, while vancomycin treatment led to alterations in the bacterial community alone. Thus, this study shows that CDI is characterised by enteric virome dysbiosis. Treatment response in FMT was associated with a high colonization level of donor-derived Caudovirales taxa in the recipient. Caudovirales bacteriophages plays a role in the efficacy of FMT in CDI.

II. FMT Donors and Recipients

Patients suffering from CDI, especially recurring CDI, are often considered as recipients for FMT treatment. Aside from CDI, other diseases and conditions, including those of digestive system or nervous system such as inflammatory bowel disease, irritable bowel syndrome, diabetes, metabolic syndrome, obesity, multiple sclerosis, autism, graft-versus host disease, vancomycin- and clindamycin-resistant enterococci, and Parkinson's Disease, are also beginning to be considered for FMT treatment.

Fecal matter used in FMT is obtained from a healthy donor and then processed into appropriate form for the intended means of delivery in the upcoming FMT procedure. Up until now, the general criterion for an FMT donor is simply that the donor is a healthy individual without any known diseases or disorders especially in the digestive tract, although some preference is often given to the members of the same household as the recipient.

The present inventors have discovered in their studies that elevated level of bacteriophage species of the Caudovirales order is often seen in the stool of CDI patients, whereas Caudovirales diversity, richness, and evenness are typically lower in these patients. On the other hand, successful FMT has been observed as correlating with increased Caudovirales diversity, richness, and evenness in a recipient following the procedure, with more of the bacteriophage species derived from the donor. This revelation enables the initial screening of healthy individuals as appropriate FMT donors for successful FMT treatment: if a candidate donor's stool has less than a minimal level of Caudovirales richness and diversity, the candidate is deemed as unsuitable as an FMT donor, and his stool should not be taken or used in FMT; if a candidate's stool sample shows at least or more than a minimal level of Caudovirales richness and diversity, then the candidate is deemed an appropriate FMT donor and his fecal material can be immediately retrieved for processing and later used in FMT.

Various methods have been reported in the literature for determining the level of bacteriophage species in a sample, for example, metagenomic sequencing of virus-like particle preparations from samples. Furthermore, the level of any given viral species may be determined by amplification and sequencing of its consensus sequence. A richness and diversity value of bacteriophage species within the Caudovirales order is often used as a parameter to indicate the appropriateness of a potential donor for providing his fecal material to be used in FMT or how likely the FMT treatment will be successful.

III. Methods for Improving FMT Efficacy

The discovery by the present inventors revealing the direct correlation between Caudovirales diversity and efficacy of FMT treatment not only allows one to devise an initial screening process to identify appropriate donors for the FMT procedure, it also enables different methods for improving FMT efficacy by choosing donors with Caudovirales diversity above a minimal value prior to the start of FMT treatment.

As discussed in the above section, when a candidate donor's stool is tested and found to contain a level of Caudovirales richness and diversity below a designated minimal value, the candidate is deemed as unsuitable as an FMT donor, and his stool should not be taken for use in FMT as it is unlikely to result in a successful FMT treatment if used. Conversely, when a proposed FMT donor whose stool is tested and found to contain a level of Caudovirales richness and diversity no less than, preferably greater than, a predetermined minimal value, the donor is deemed as a suitable donor for FMT, and his stool should be immediately collected and processed for use in FMT in order to achieve a desirable outcome.

First, for a patient who has been considered for receiving FMT and has also been found to have an elevated level of bacteriophage within the order of Caudovirales and/or a lower Caudovirales diversity/richness in his stool sample, which may indicate a diminished chance of a successful FMT, measures can be taken to lower his overall level of Caudovirales and/or increase Caudovirales diversity/richness before FMT is commenced so that a much greater efficacy can be achieved for the FMT procedure. For instance, an antiviral agent capable of suppressing the growth or proliferation of the bacteriophages within the order of Caudovirales, especially those specific bacteriophage species significantly over-represented in all Caudovirales species so as to cause the suppression of the order, can be administered to the patient in an effective amount such that the level of at least some species of the Caudovirales order in the patient's digestive tract and in his feces is significantly reduced (e.g., leading to a reduction of the total amount of the Caudovirales bacteriophages and/or an alteration in the Caudovirales diversity/richness) prior to the start of the FMT procedure. In this case, the patient's Caudovirales bacteriophage level is to be determined twice: once at the initial screening stage, a second time after the initial level is deemed too high for an effective FMT and after an antiviral agent has been given to the patient. Once the Caudovirales bacteriophage level is confirmed as lowered to a percentage that would allow satisfactory FMT outcome, the patient is then ready to undergo FMT as a recipient.

Second, for a candidate who has been deemed improper to serve as an FMT donor due to a higher level of overall Caudovirales bacteriophage and/or a reduced level of Caudovirales diversity/richness in his stool, the expected undesirable FMT outcome can be remedied by treating the candidate donor with an effective amount of an antiviral agent capable of suppressing the growth or proliferation of bacteriophage of order of Caudovirales or an antiviral agent that specifically can be administered. Since the donor's body, especially the gastrointestinal tract, contains a vast collection of microorganisms many of which are important for the health of gut microflora and for the success of FMT, a useful antiviral agent for this purpose cannot be one with broad-spectrum antiviral toxicity. Rather, it should be an agent that narrowly and precisely targets the species within the order of Caudovirales, especially the species significantly over-represented, without significantly affecting other bacteriophage species, including those severely under-represented Caudovirales bacteriophages. Although the agent may be of any chemical compound in nature, small polynucleotides (e.g., siRNAs, miRNAs, miniRNAs, lncRNAs, or antisense DNAs/RNAs) and bacteria-mediated CRISPR immune system may be the most effective in achieving the specific task of disrupting the expression of one or more key genes in the life cycle of the targeted bacteriophage(s) so as to specifically inhibit the proliferation of the target species only without significant impact on other closely related bacteriophage species.

As a further possibility, fecal materials from multiple donors may be pooled before undergoing processing in preparation for use in FMT for the purpose of enhancing Caudovirales richness and generally better FMT efficacy. The suitability of such pooled or combined fecal materials for FMT and likelihood of successful FMT outcome can be enhanced, when among the multiple donors there is at least one (in some cases two or more) donor who has been tested and shown to exhibit a desirable Caudovirales bacteriophage profile in his stool sample (e.g., a relatively lower level of overall Caudovirales bacteriophage and/or a relatively higher level of Caudovirales bacteriophage richness or diversity, especially when compared with the corresponding levels in a stool sample obtained from a potential recipient or other potential donor or donors).

Immediately upon completion of FMT procedure, the recipient may be further monitored by undergoing continuous testing of the level of Caudovirales overall and/or Caudovirales diversity/richness in the stool samples on a daily basis for up to 5 days post-FMT and over longer time intervals (e.g., on a monthly, bimonthly, or quarterly testing schedule) for up to 6, 8, 12, 18, or 24 months, while the clinical symptoms of the condition being treated are also being monitored in order to assess FMT outcome and the corresponding Caudovirales diversity level in the recipient.

IV. Kits and Compositions for Improved FMT

The present invention also provides novel kits and compositions that can be used for improving FMT efficacy. For example, in a kit for treating a patient in need of FMT, a first composition intended for transplantation into a patient or FMT recipient and a second composition intended to be administered to the recipient for reducing the overall level of Caudovirales bacteriophages or specific Caudovirales bacteriophage species in the recipient. The first composition comprises a fecal material from a donor, which has been processed, formulated, and packaged to be in an appropriate form in accordance with the delivery means in the FMT procedure, which may be by direct deposit in the recipient's lower gastrointestinal tract (e.g., wet or semi-wet form) or by oral ingestion (e.g., frozen dried encapsulated). The second composition comprises an antiviral agent capable of suppressing the growth/proliferation of Caudovirales bacteriophages in general or specific Caudovirales bacteriophage species that are significantly over-represented, which may be a broad-spectrum antiviral agent or more preferably a specific inhibitor of certain targeted, over-represented Caudovirales species, and one or more pharmaceutically acceptable excipient. The composition is formulated for the intended delivery method of the antiviral agent, for example, by injection (intravenous, intraperitoneal, intramuscular, or subcutaneous injection) or by oral ingestion or by local deposit (e.g., suppositories). The first and second compositions are often kept separately in two different containers in the kit. Typically, the kit will further include printed material providing detailed instructions for users of the kit, such as providing information of the schedule and dosing arrangement for administering the first and second compositions to a recipient.

In another aspect of this invention, alternative compositions useful in FMT with improved efficacy may be devised to contain at least these two components: (1) a donor stool material containing live fecal microorganisms including Caudovirales bacteriophage species; and (2) an antiviral agent that specifically suppresses the growth or proliferation of Caudovirales bacteriophage in general and/or targeting certain species of over-represented Caudovirales bacteriophages specifically, but exhibits no such suppressive or inhibitory effect against other viral species. Component (2) preferably is not a broad-spectrum antiviral agent; rather, it should be a specific antiviral agent that specifically targets certain over-represented bacteriophage species within the order of Caudovirales. For example, it may be short polynucleotide in nature of, e.g., a small inhibitory RNA, microRNA, miniRNA, lncRNA, or an antisense oligonucleotide, that is capable of disrupting the expression of at least one key gene in the life cycle of the targeted species of Caudovirales bacteriophages, such that the agent is capable of specifically targeting the species only without significantly affecting other closely related viral species. Component (2) is particularly useful in the case of a donor's stool containing a level of Caudovirales too high and/or Caudovirales diversity/richness too low to permit a satisfactory FMT outcome, as it is capable of locally and specifically suppressing the proliferation of such over-represented bacteriophage species so as to ensure the success of FMT despite the less than desirable quality of the donor fecal material.

EXAMPLES

The following examples are provided by way of illustration only and not by way of limitation. Those of skill in the art will readily recognize a variety of non-critical parameters that could be changed or modified to yield essentially the same or similar results.

Example 1: Bacteriophage Transfer During Fecal Microbiota Transplantation in *Clostridium difficile* Infection is Associated with Treatment Outcome Introduction

*Clostridium difficile* infection (CDI) is a leading nosocomial infection affecting half a million people in the USA.[1][2] Antibiotic therapy is the first-line treatment, but up to one-third of patients do not achieve a durable response. Recently, fecal microbiota transplantation (FMT) with either fresh or frozen stool from healthy donor has been shown to be highly effective in patients with recurrent CDI with a cure rate of 85%-90%.[3-5] The efficacy of FMT is mostly based on restoration of the phylogenetic diversity and bacterial microbiota to resemble that of a 'healthy' individual.[6-8] However, the mechanism and long-term effects of FMT remain poorly understood.

Humans are also colonized by a large population of viruses, especially bacteriophages, that may play a pivotal role in microbiome ecology.[9-11] Limited studies have reported that bacteriophages can be transferred to recipients from the donor microbiota.[12-15] In a study of three patients with UC, transfer of multiple viral lineages through FMT was reported.[13] In a single case report of CDI, virome alterations over time after FMT largely consisted of Caudovirales.[12 16] Recently, a preliminary investigation of five patients with CDI showed that transfer of sterile fecal filtrates from donor stool was effective to eliminate symptoms.[15] Overall, these data suggest that other than bacterial components, bacteriophages or bacteriocins are likely contributing to the normal intestinal microenvironment in FMT. Besides, whether patients with CDI have alterations in the enteric virome and the extent of such changes have also not been studied. In this study, it is postulated that bacteriophages may interact with host microbes and influence the clinical outcome after FMT. ultra-deep virus-like particles' (VLPs') metagenomic sequencing and 16S rDNA sequencing was performed to determine enteric virome and bacteriophages-bacteria interactions in subjects with CDI compared with healthy controls. Changes in the virome post FMT were also serially assessed and examined whether bacteriophage transfer is associated with the clinical outcome of FMT. This pilot study is the first and largest to date to characterise the enteric virome alterations in CDI and to elucidate changes in viral communities after FMT and its relatedness with treatment outcome.

Results

Virome Alterations in CDI Compared with Controls

Figure 7C:
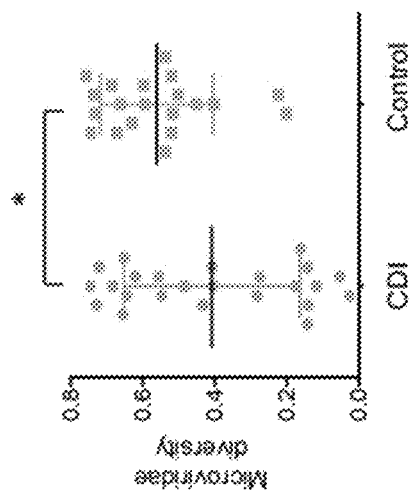
FIGS. 7A-7C Dysbiosis of the enteric virome in CDI (FIG. 7A) Comparison of Caudovirales diversity at the contig level in CDI and controls. Statistical significance was determined by Mann-Whitney test. *P<0.05.
Figure 7B:
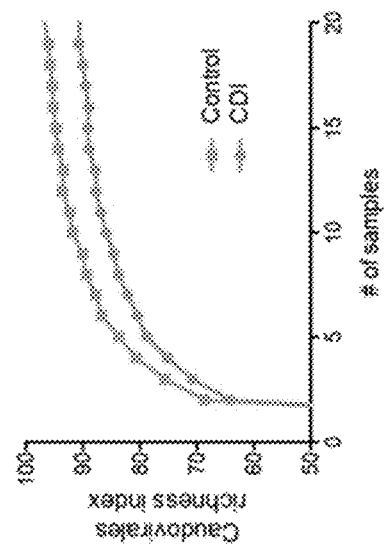
Figure 7A:
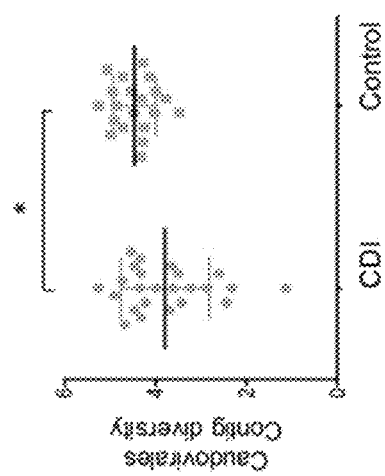

The present inventors first compared the fecal virome composition in subjects with CDI with that of healthy household controls. On average, 21 202 400±5 385 756 clean paired-end reads were obtained from the enriched fecal VLP preparations. Among the common viral orders detected, the most abundant in both CDI and healthy household controls was Caudovirales, one taxon of a consortium of temperate double-stranded DNA (dsDNA) bacteriophages. Compared with healthy individuals, CDI subjects had a significantly higher abundance of Caudovirales (FIG. 1A), but a decreased diversity of Caudovirales at the species level (FIG. 1B) and at the contig level (FIG. 7A). There was also a significant decrease in the richness and evenness of Caudovirales in CDI compared with healthy controls (FIG. 1C, D). In line with that, the rate of acquisition of new Caudovirales taxa in control samples rapidly outpaced new taxa acquisition in CDI samples, further demonstrating a lower Caudovirales richness in CDI than in controls (FIG. 7B). At the family level, CDI showed a decreased abundance of Microviridae compared with that of controls (FIG. 1E), as well as a decrease in Microviridae diversity (FIG. 7C). In contrast, the abundance of Anelloviridae was increased in CDI compared with controls (FIG. 1E). Using linear regression test, no significant correlation was found between the diversity or richness of Caudovirales and age, gender, household relationship or time of sample collection (Table 2). After adjusting for multiple comparisons, no significant correlation was shown by MaAsLin between viral abundances and age, gender or time of sample collection. There was however a correlation between viral abundances and household relationship (False Discovery Rate (FDR) multiple comparison adjusted q<0.05), which suggests a household effect on the gut virome structure. In healthy controls, there was a significant inverse correlation between Caudovirales and Microviridae, Caudovirales and Anelloviridae, which was not seen in CDI (FIG. 1F). Overall, these findings indicate dysbiosis of the enteric virome in patients with CDI.

Figure 8A:
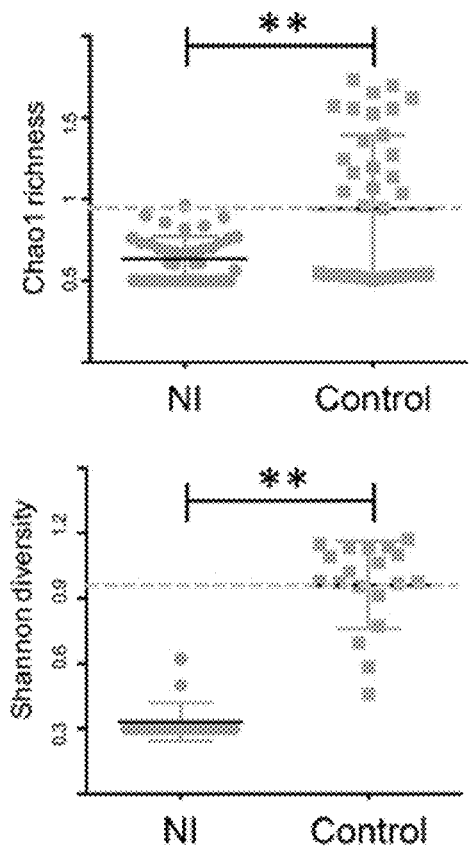
FIGS. 8A-8B Dysbiosis of the enteric virome in NI (FIG. 8A) Comparison of Caudovirales diversity and richness between Norovirus (NI) subjects and healthy controls at the species level.
Figure 8B:
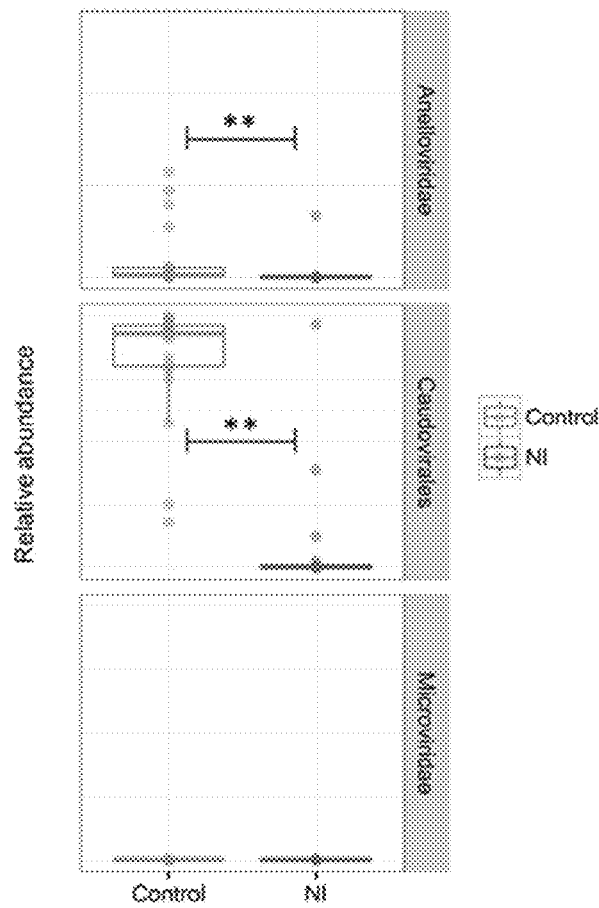

It was next assessed whether virome dysbiosis was specific to CDI diarrhoea by including an additional cohort of subjects with norovirus-associated infectious diarrhoea. It was found that there was a significant decrease in both the richness and diversity of Caudovirales in subjects with norovirus infection compared with healthy controls (FIG. 8A), suggesting that altered virome richness and diversity may reflect a generic pathogen-driven event in subjects with acute infectious diarrhoea illness. However, norovirus subjects had a significantly lower abundance of Caudovirales and Anelloviridae (both p<0.05) compared with healthy controls, while no marked difference was observed in the relative abundance of Microviridae between norovirus subjects and controls (FIG. 8B). These data indicate that enteric virome dysbiosis in CDI is likely to be disease-specific.

Enteric Virome Alterations in Patients with CDI after FMT

Figure 2A:
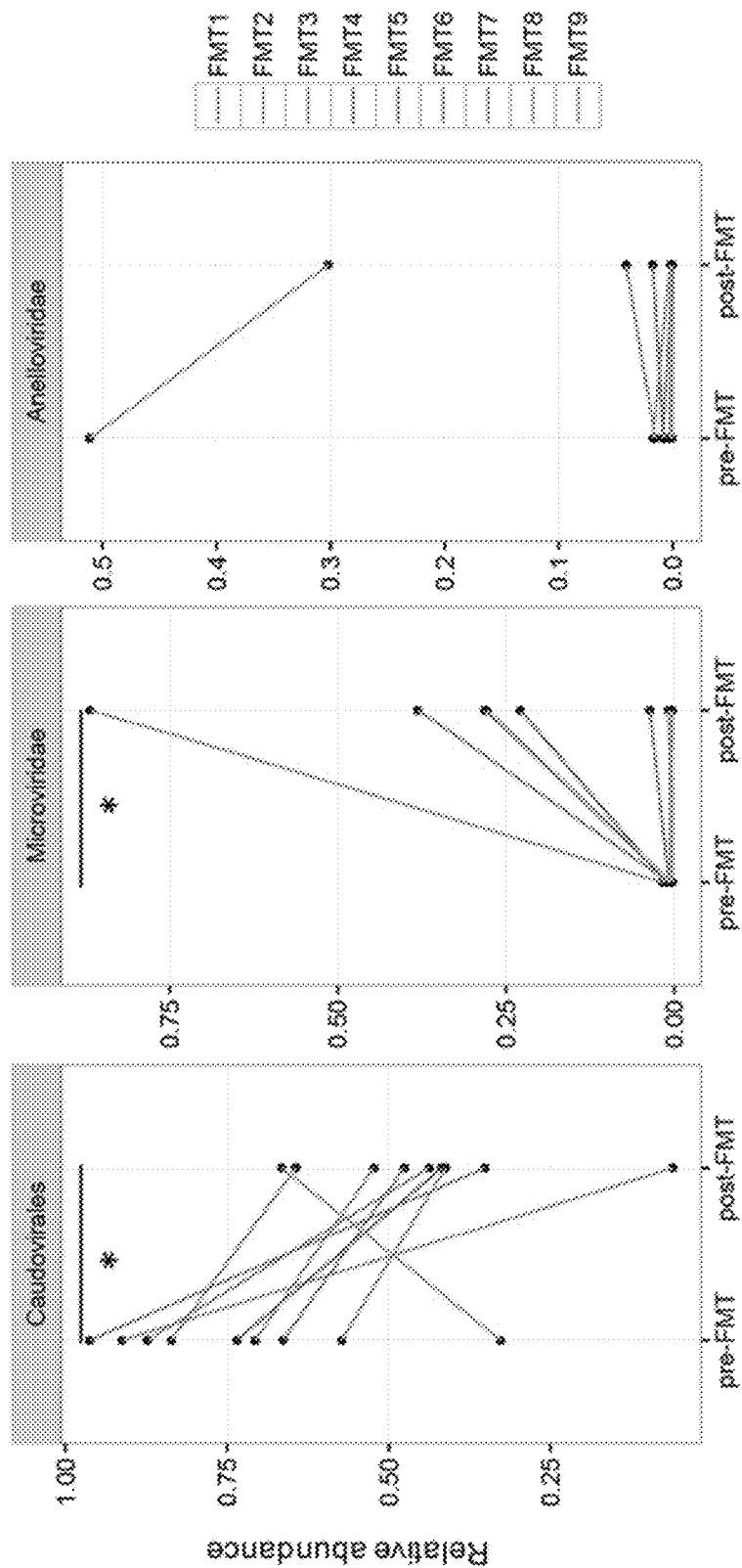
FIGS. 2A-2B Alterations in the enteric virome after fecal microbiota transplantation (FMT).
Figure 2B:
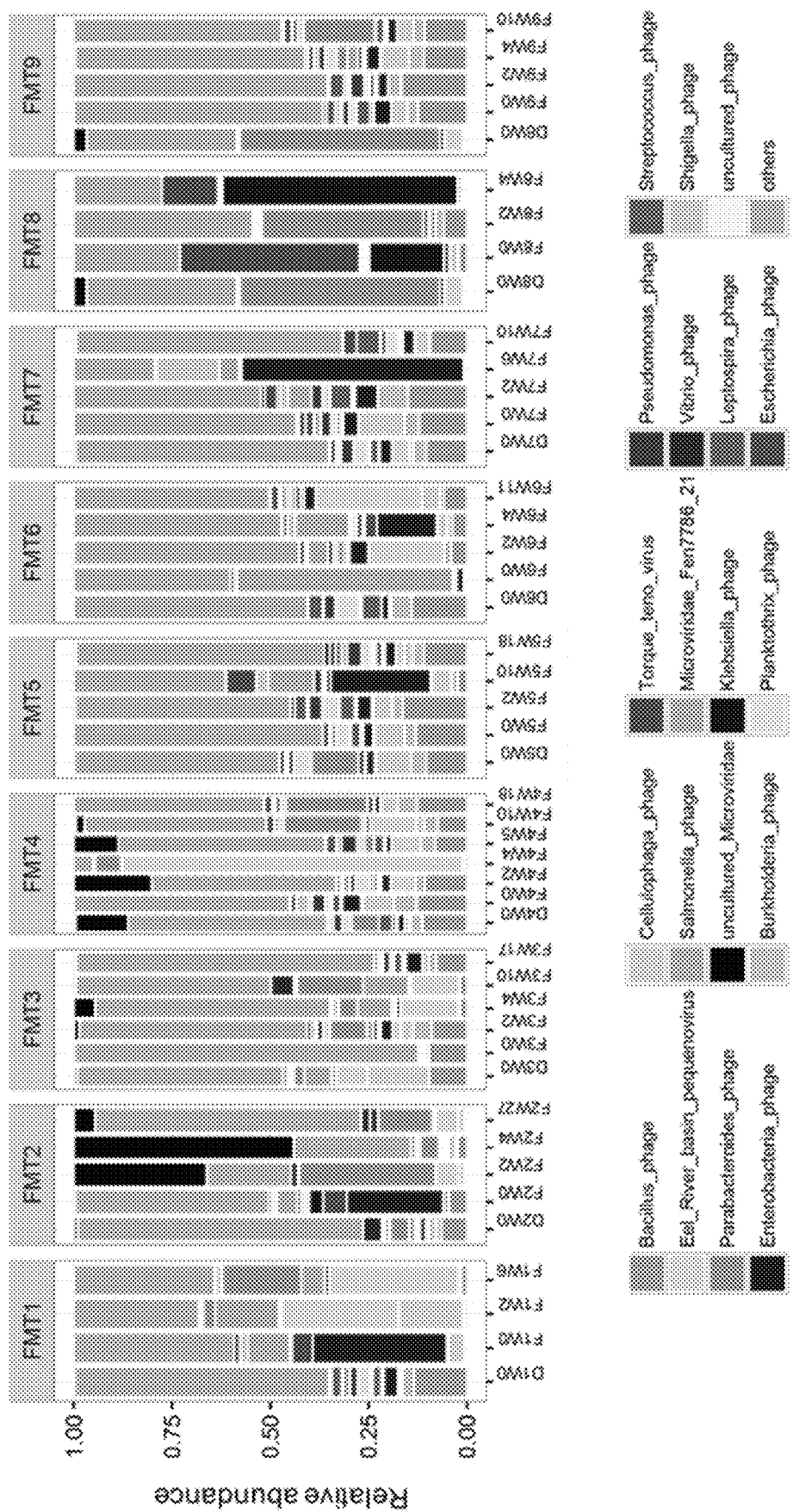
Figure 6:
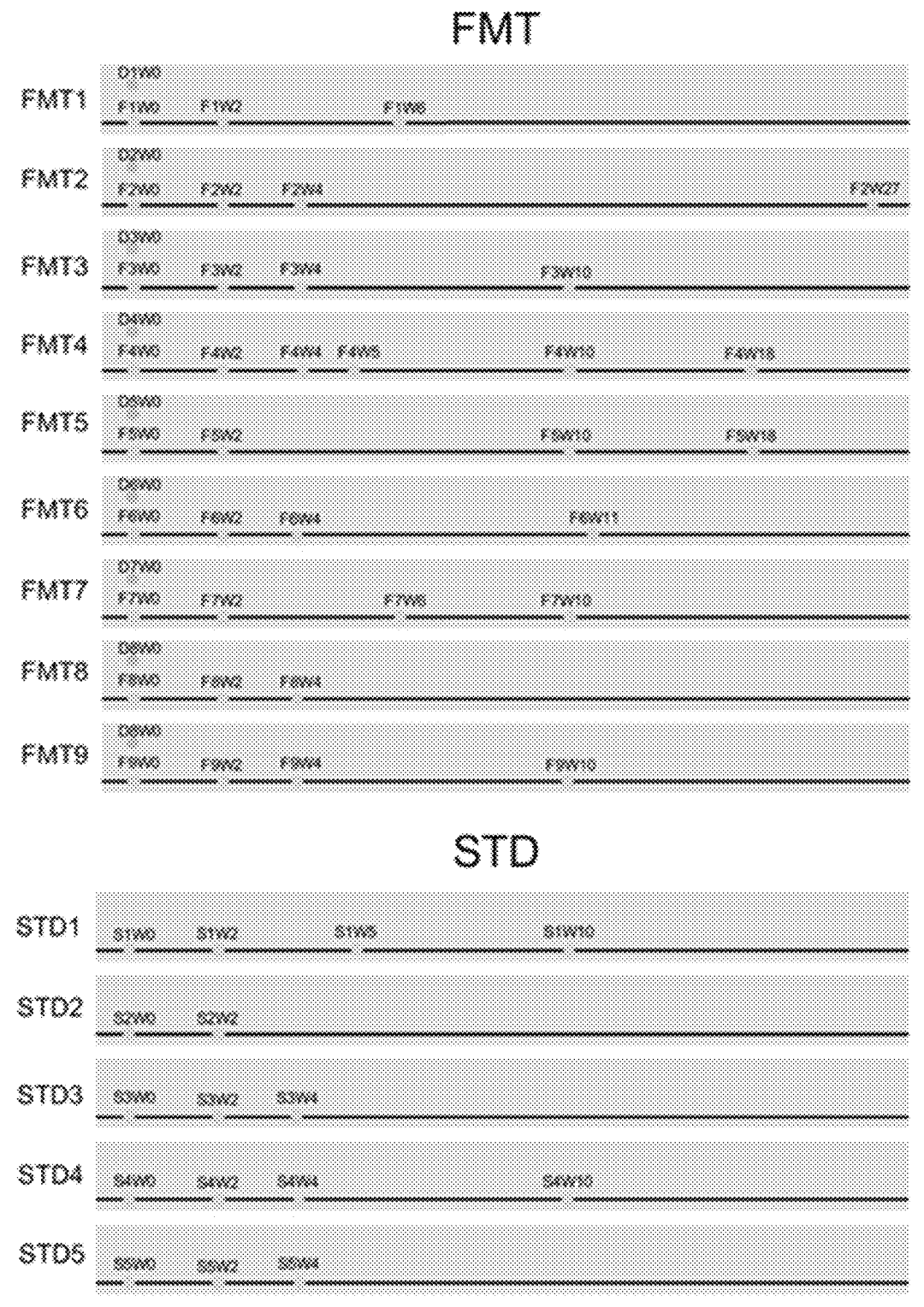

It was next investigated whether the enteric virome changes after FMT. Nine CDI subjects who received FMT were followed up longitudinally at different time points (FIG. 6). CDI subjects showed a decrease in Caudovirales abundance and an increase in Microviridae abundance after FMT (paired Wilcoxon sign permutation test, p<0.05) (FIG. 2A). There were profound differences in the virome composition between the nine FMT subjects (FIG. 2B). Similar virome configurations were observed between donor baseline stool sample, recipient baseline stool sample and the follow-up stool samples of the recipient. As the donor and recipient shared the same family origin, except for FMT9, this observation, confirmed also by MaAsLin, further illustrated a significant household effect on the virome structure.

Figure 9:
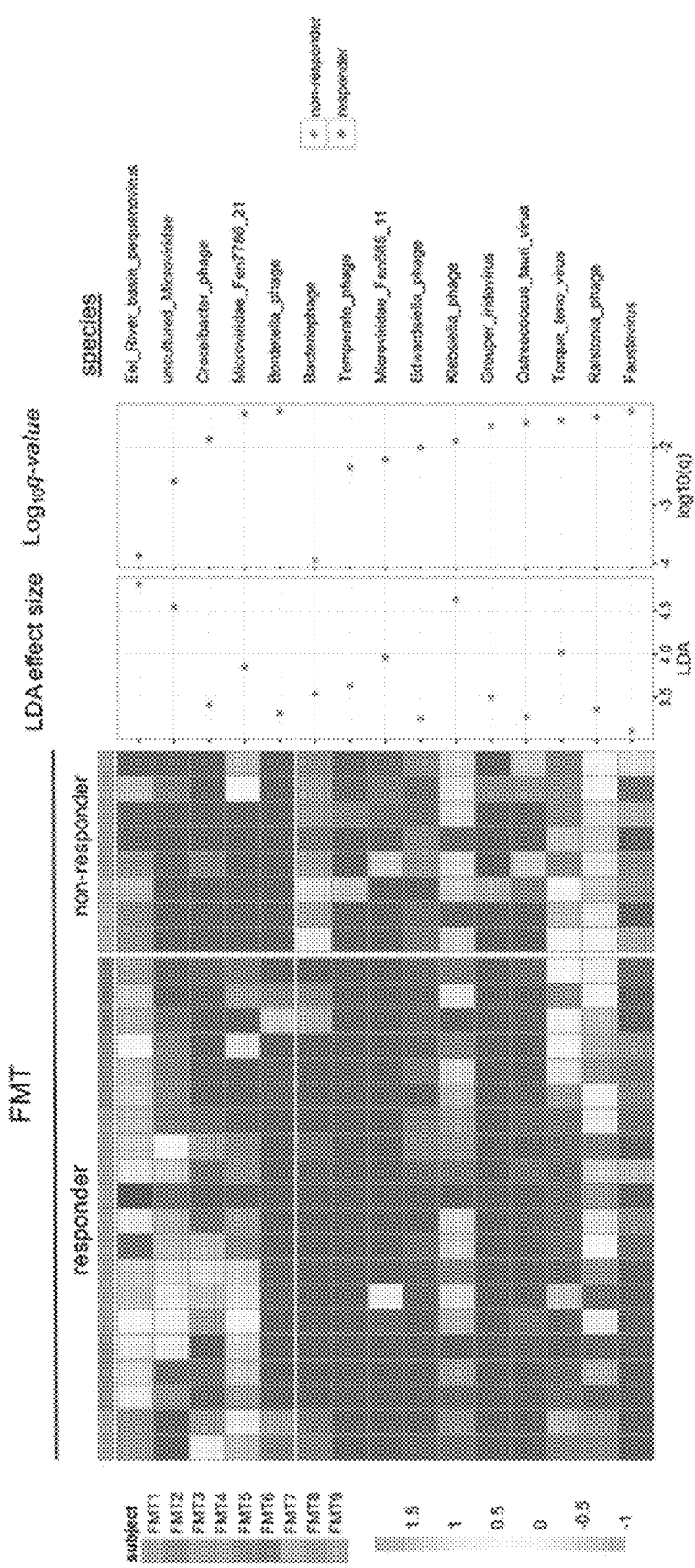
FIG. 9 Differentially enriched viral species across post-FMT samples of FMT responders versus non-responders. Statistical significance level was determined by lefSe analysis with FDR correction. LDA effect size, q value and species annotation are shown. Green dots indicate species enriched in responders, while red dots indicate species enriched in non-responders.

In the nine CDI subjects who received FMT treatment, six subjects remained symptom-free with a negative stool *C. difficile* toxin at the last follow-up (responders, FMT1-FMT6), while three developed recurrence of CDI (non-responders, FMT7-FMT9) (Table 1). 15 species were identified differentially enriched between FMT responders and non-responders via LEfSe analysis (FIG. 9). Among them, Eel River basin pequenovirus, a recently identified sister clade to the enterobacteria microviruses, which may prey on Proteobacteria,[19] was the most abundant and significant species harboured in the post-FMT stools of the responders.

Donor Caudovirales Richness and Treatment Response

Figures 3A, 3B:
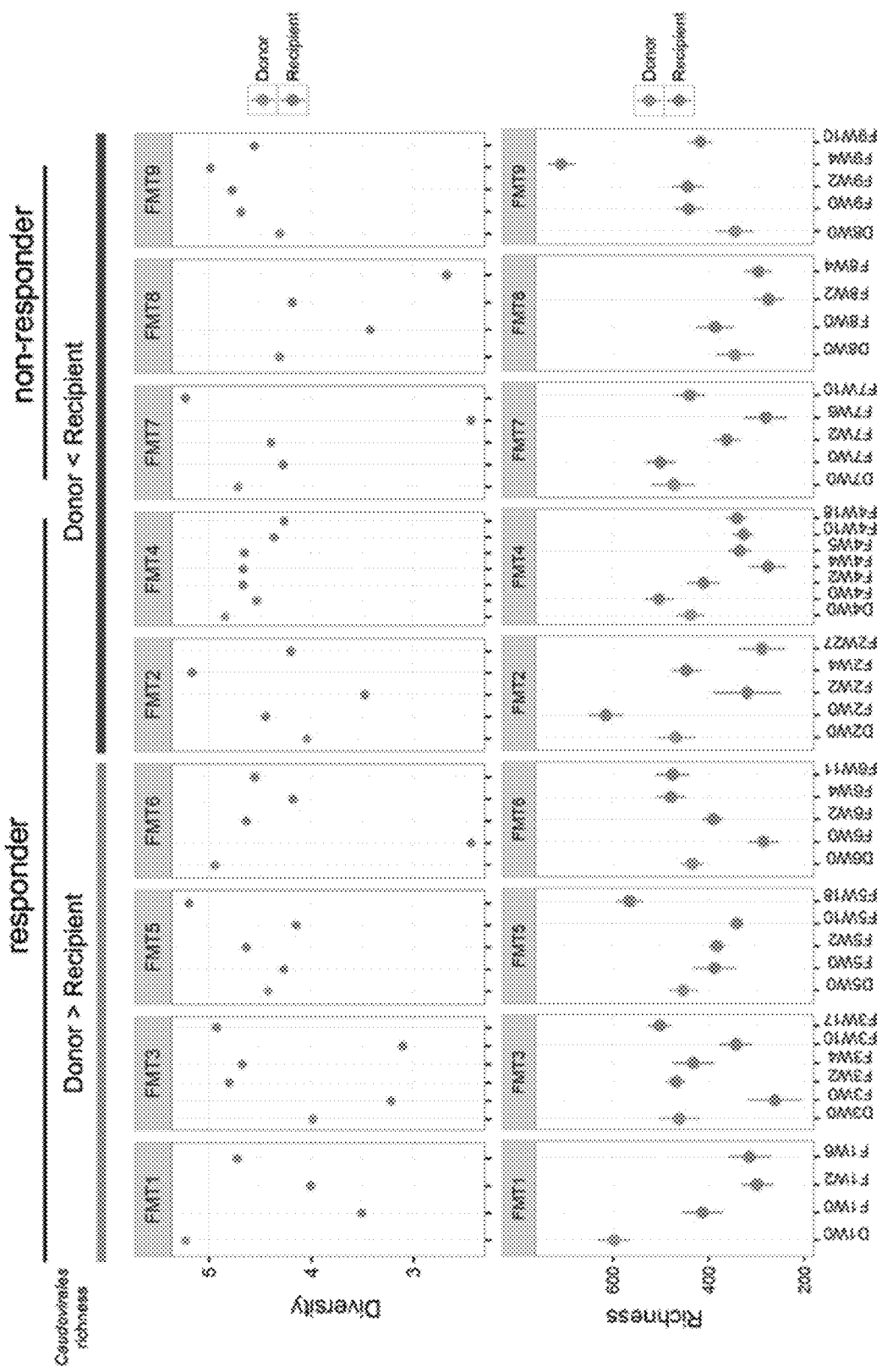
FIGS. 3A-3C Alterations of Caudovirales diversity and richness after fecal microbiota transplantation (FMT). Changes in the Caudovirales diversity (FIG. 3A) and Caudovirales richness (FIG. 3B) of the stool samples of donor and *Clostridium difficile* infection (CDI) subjects after FMT at different time points until the last follow-up.
Figure 3C:
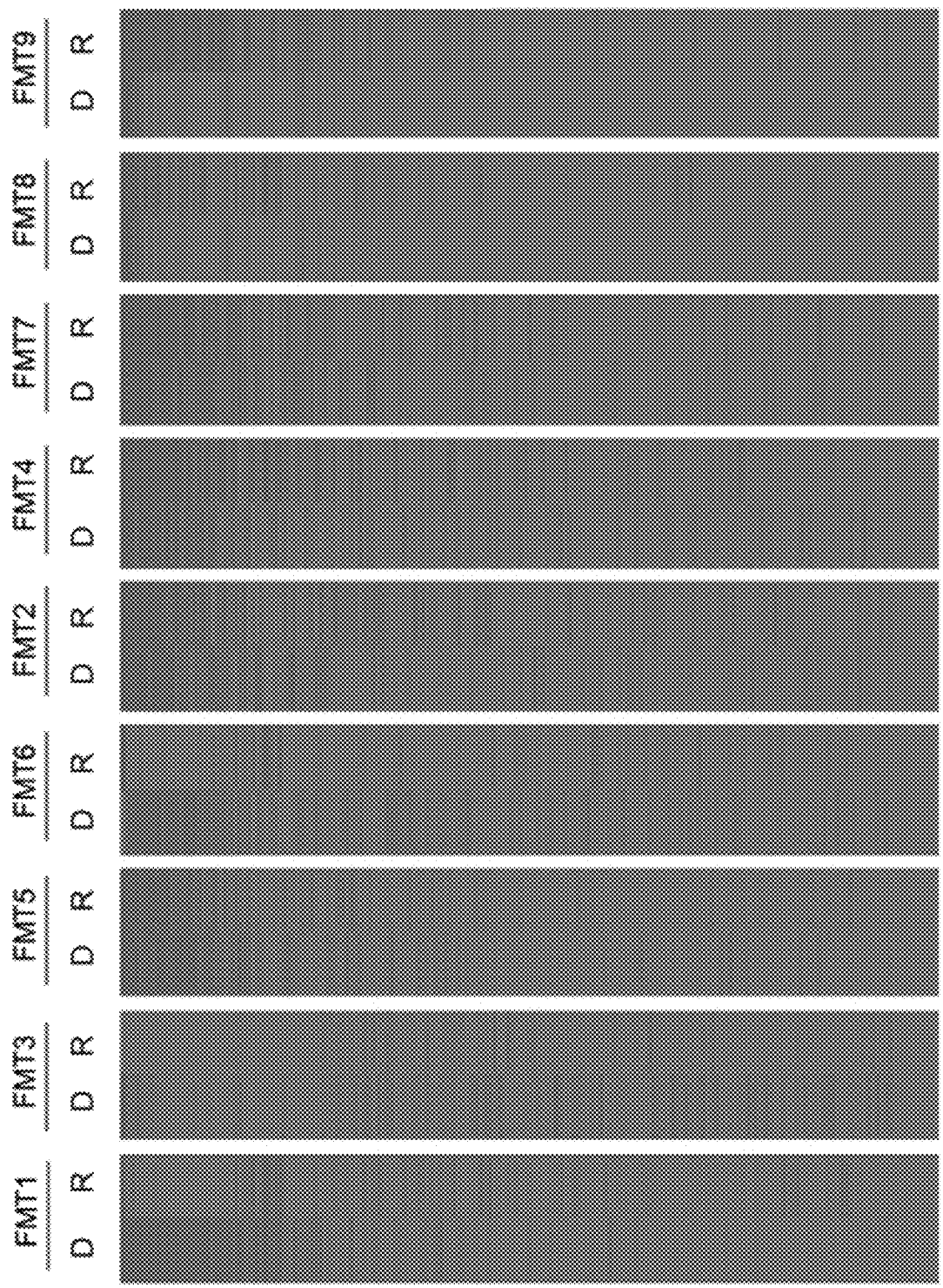

Given that Caudovirales was the most abundant and significantly changed viral taxon in patients with CDI, the inventors focused on Caudovirales hereafter and studied the effect of donor Caudovirales richness on treatment response. In subjects FMT1, FMT3, FMT5 and FMT6, whereby the Caudovirales richness of the donor was higher than that of the recipient (FIG. 3A), all recipients were cured. These recipients also showed an increase in the diversity of Caudovirales after FMT, though it is not consistent in the richness change post FMT (FIG. 3A, B). In these four CDI subjects who responded to FMT, the Caudovirales contigs found in the donor baseline sample outnumbered that of the contigs in the recipient baseline stool sample (FIG. 3C), further substantiating that donor Caudovirales richness was higher than that of the recipient. In contrast, when the Caudovirales richness of the donor was lower than that of the recipient (FMT2, FMT4, FMT7, FMT8 and FMT9), the treatment outcome was not consistent across the recipients. FMT2 and FMT4 responded to treatment, but FMT7, FMT8 and FMT9 did not. The Caudovirales diversity and richness alterations post FMT were inconsistent among these subjects. The simultaneous treatment failure in subjects FMT8 and FMT9, where they shared the same donor, provided a valuable piece of evidence for a donor effect with regard to virome on FMT efficacy. Overall, it was found that when the Caudovirales richness of the donor was higher than that of the recipient, all the CDI subjects achieved a response to FMT.

Figure 4A:
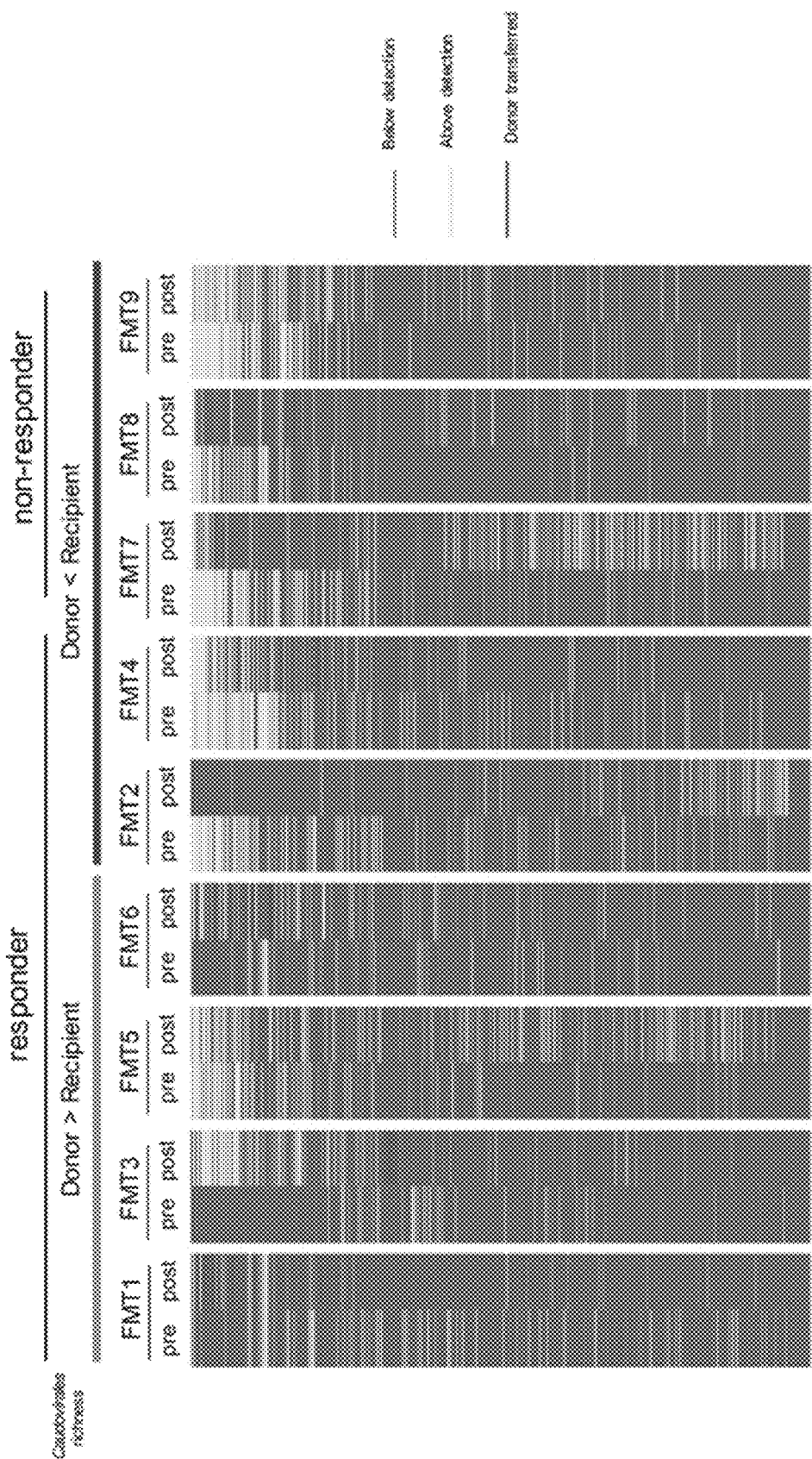
FIGS. 4A-4E Transfer of Caudovirales bacteriophages and fecal microbiota transplantation (FMT) treatment outcome.
Figure 4B:
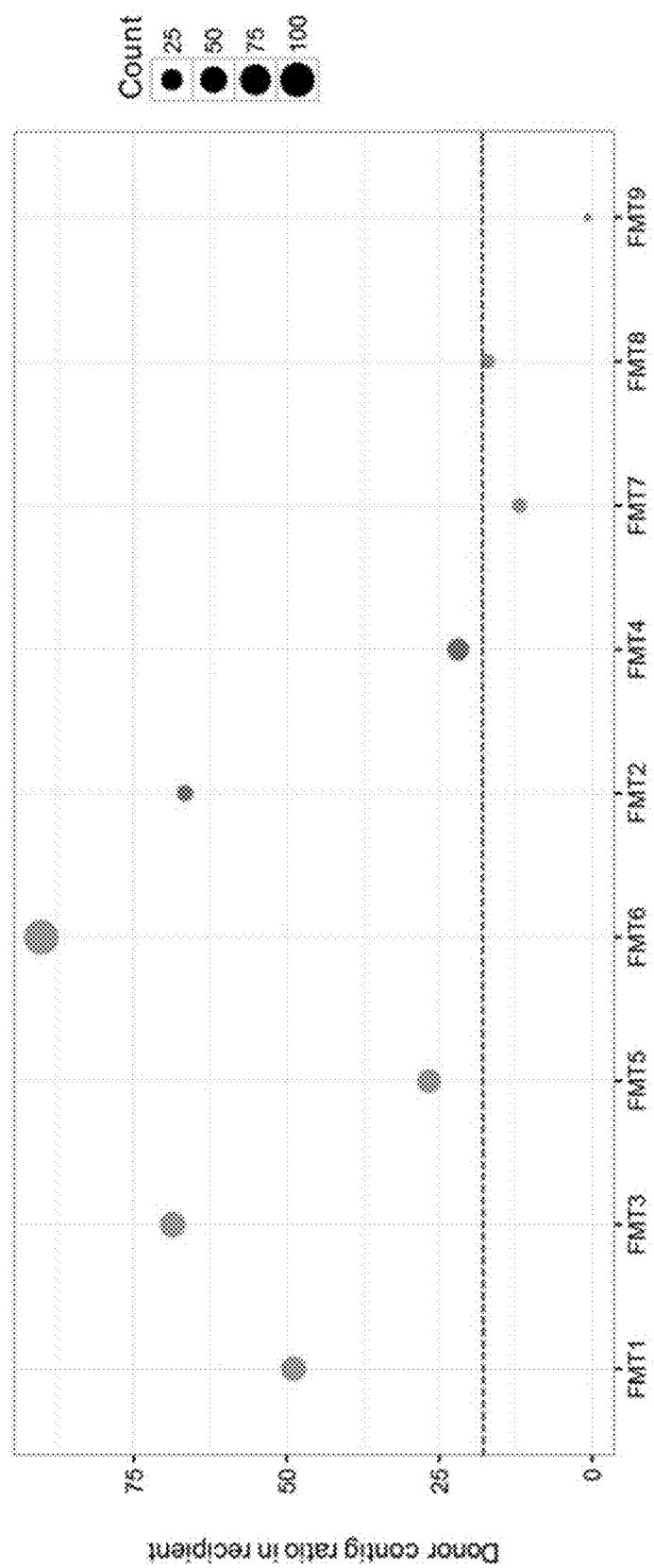
Figure 4C:
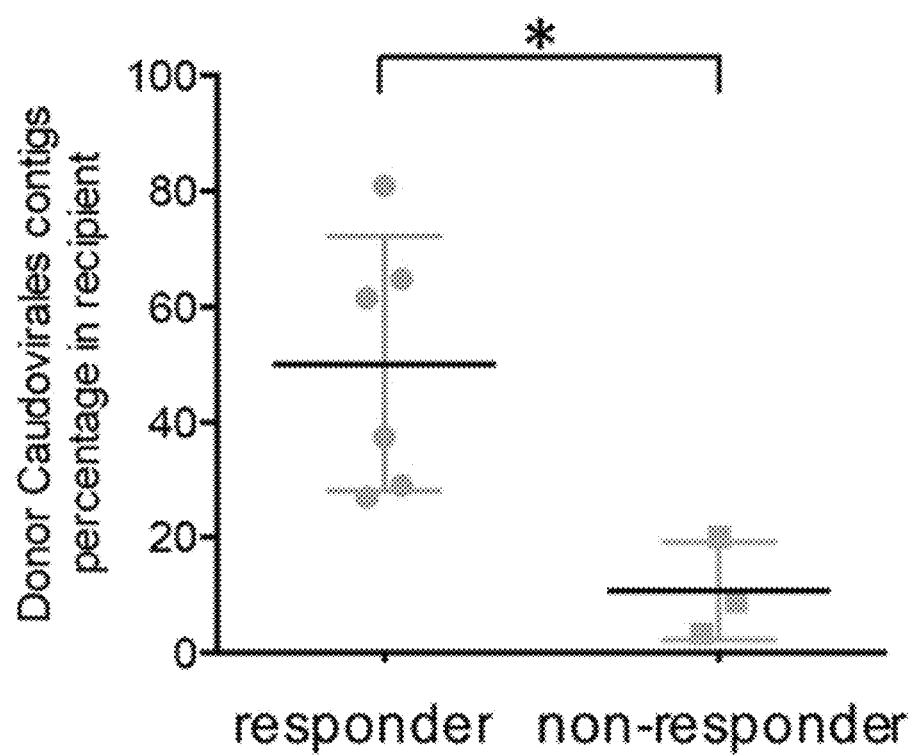
Figure 10A:
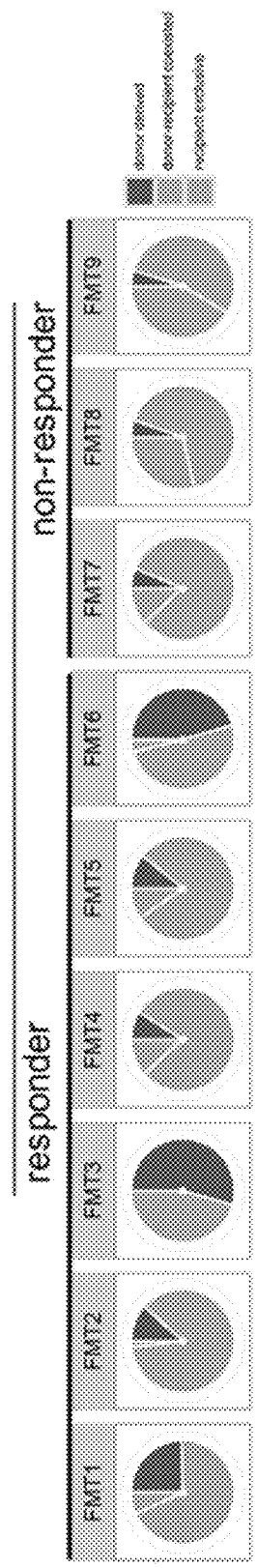
FIGS. 10A-10B Present ratio of donor transferred Caudovirales bacteriophages in recipients after FMT (FIG. 10A) Proportion of Caudovirales species present in CDI subjects after FMT in the last follow-up samples. Comparison of the frequency of donor derived Caudovirales species in FMT responders and non-responders was determined by Mann-Whitney test. *P<0.05.
Figure 10B:
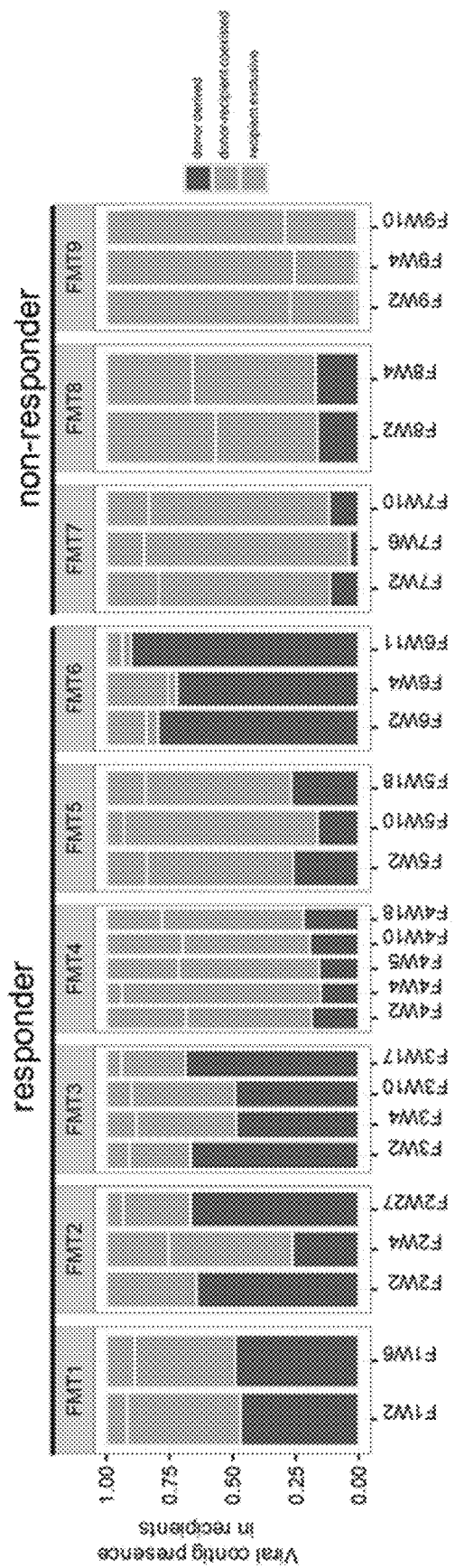

Transfer of Caudovirales Bacteriophages from Donor to Recipient and Treatment Response It was next assessed the presence of donor-derived Caudovirales in relation to treatment response. A larger proportion of Caudovirales contigs was transferred from the donor to the recipient detected at the last follow-up stool in FMT responders than in FMT non-responders (FIG. 4A, B). Donor-derived Caudovirales occupied a significantly larger fraction (>20%) of the virome in the FMT responders than in the non-responders (<20%) (FIG. 4B,C, Mann-Whitney test, p<0.05). A similar and consistent pattern was also observed at the species level (FIG. 10A). Moreover, the presence of donor-derived Caudovirales contigs in the recipients remained sustainable over time after FMT. FMT responders consistently exhibited higher levels of donor-derived Caudovirales contig colonisation throughout the follow-up period when compared with FMT non-responders (FIG. 10B). Thus, the quantity and final proportion of donor-derived Caudovirales in the recipient appeared to be associated with treatment outcome of FMT.

Figure 4D:
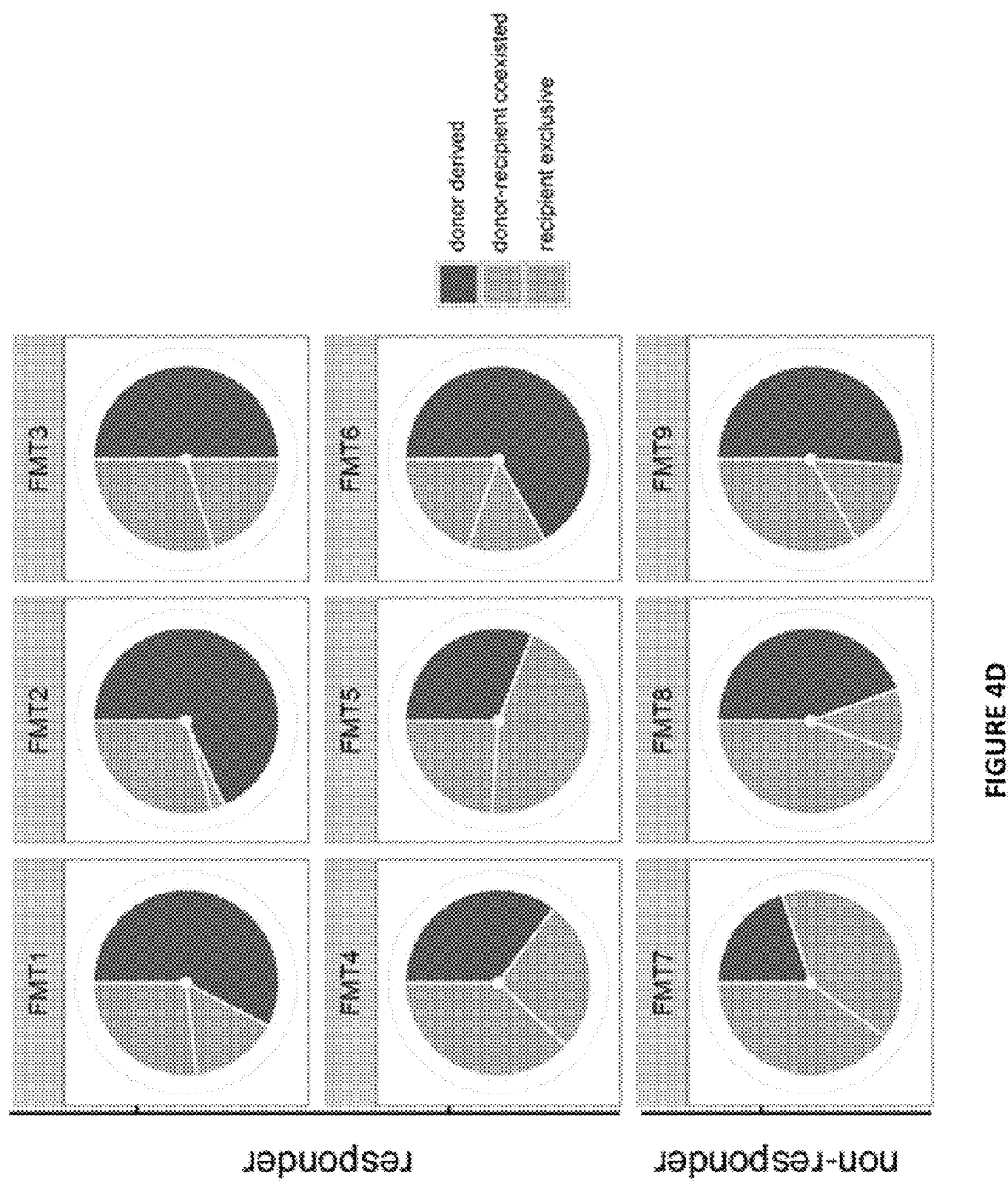
Figure 4E:
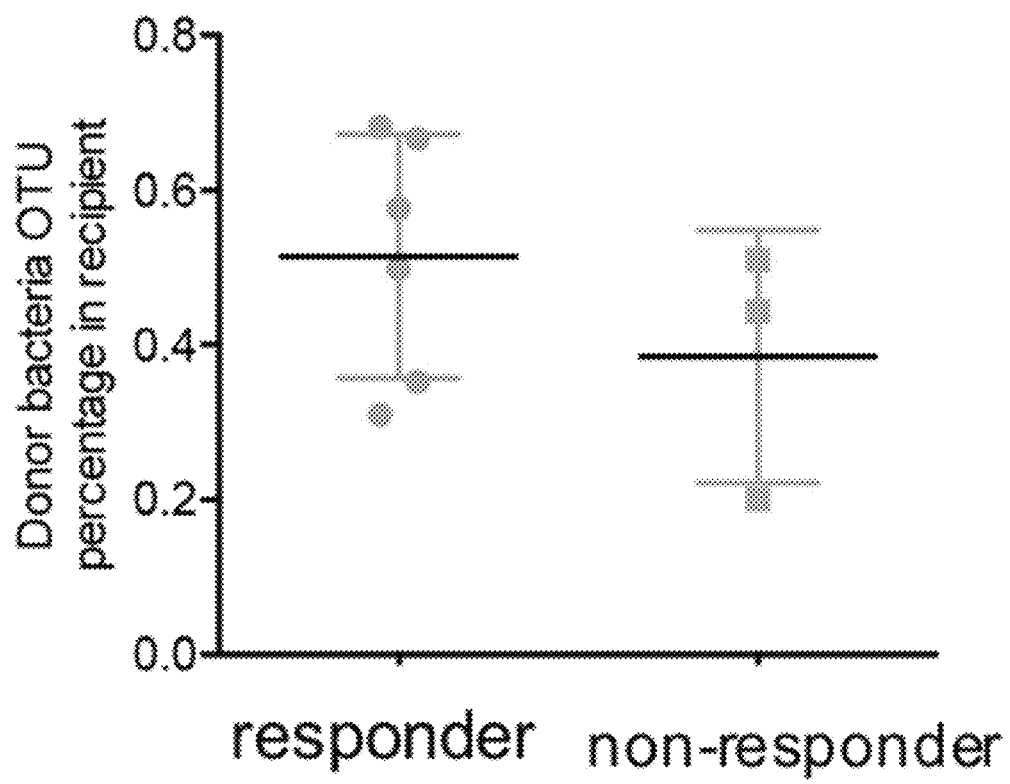
Figure 11A:
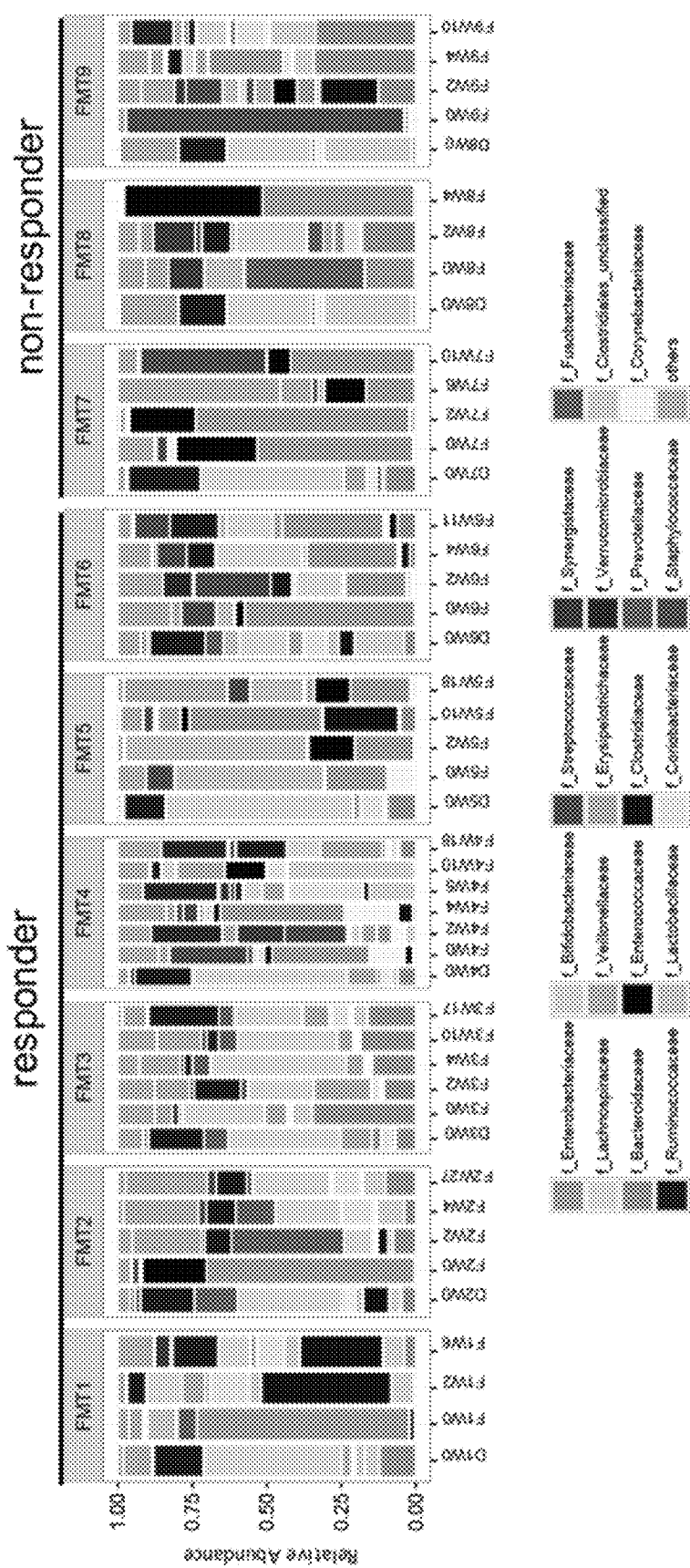
FIGS. 11A-11C Alterations in the bacterial microbiome over the course of post-FMT follow-up (FIG. 11A) Changes of the relative abundance of top19 bacterial families in the follow-up stool samples of FMT recipients. "F" indicates FMT recipient. "D" indicates FMT donor. "W" indicates weeks post treatment.
Figure 11B:
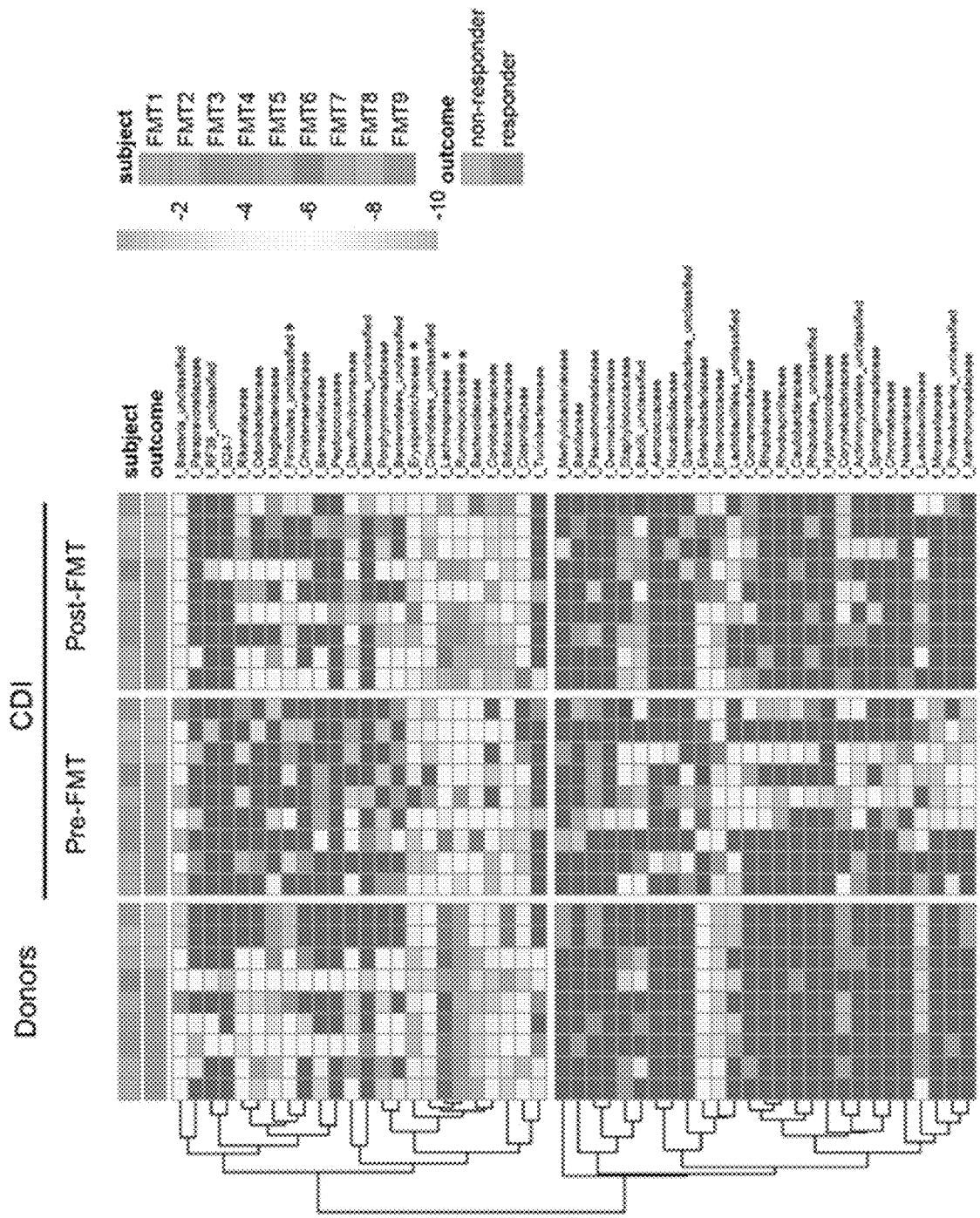
Figure 11C:
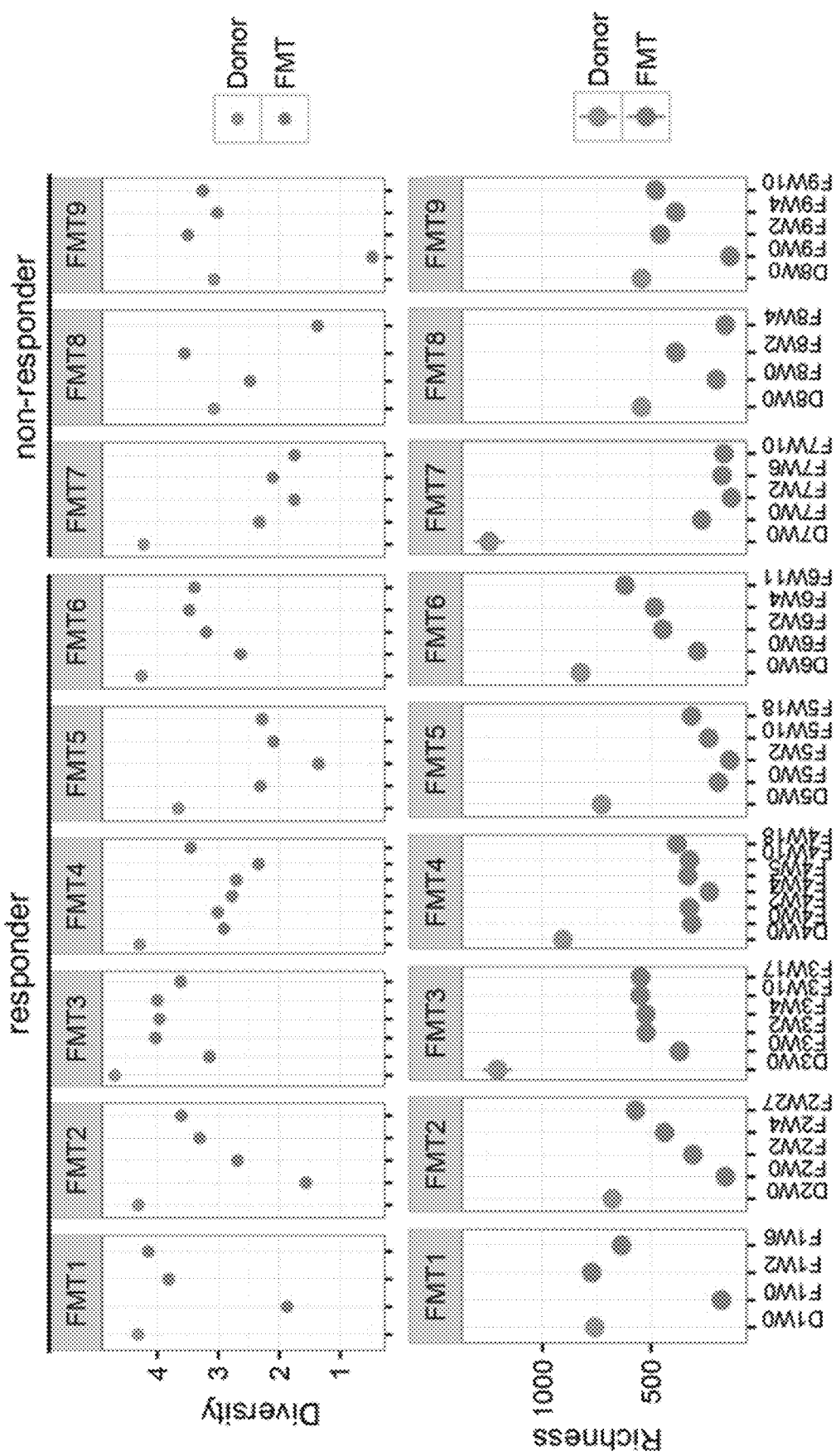

Bacterial transfer after FMT was also investigated and correlated with treatment outcome. Increased frequency of bacterial families was found in the stool of CDI subjects after FMT, which included Lachnospiraceae and Ruminococcaceae (FIG. 11A, B). However, there was no significant difference in the frequency of donor-transferred bacterial OTUs between FMT responders and FMT non-responders (FIG. 4D, E). In two subjects who had early CDI recurrence (FMT7 and FMT8), a lower abundance of donor-transferred bacteria and a lack of increase in the bacterial diversity and richness were observed after FMT (FIG. 11B, C). These two subjects also had a low Caudovirales colonisation. Hence, early disease recurrence in FMT7 and FMT8 after FMT might be related to a lack of colonisation of both bacteria and viruses. Subject FMT9 experienced disease recurrence at week 28. This subject had low levels of Caudovirales taxa colonisation throughout the post-FMT follow-up stool samples even though there was an increase in bacterial diversity and richness and substantial bacteria colonisation after FMT (FIG. 11B, C). Overall, FMT responders had a lower colonisation of Caudovirales bacteriophages than non-responders. These data suggest a role of bacteriophages in the efficacy of long-term FMT outcomes.

Figure 12A:
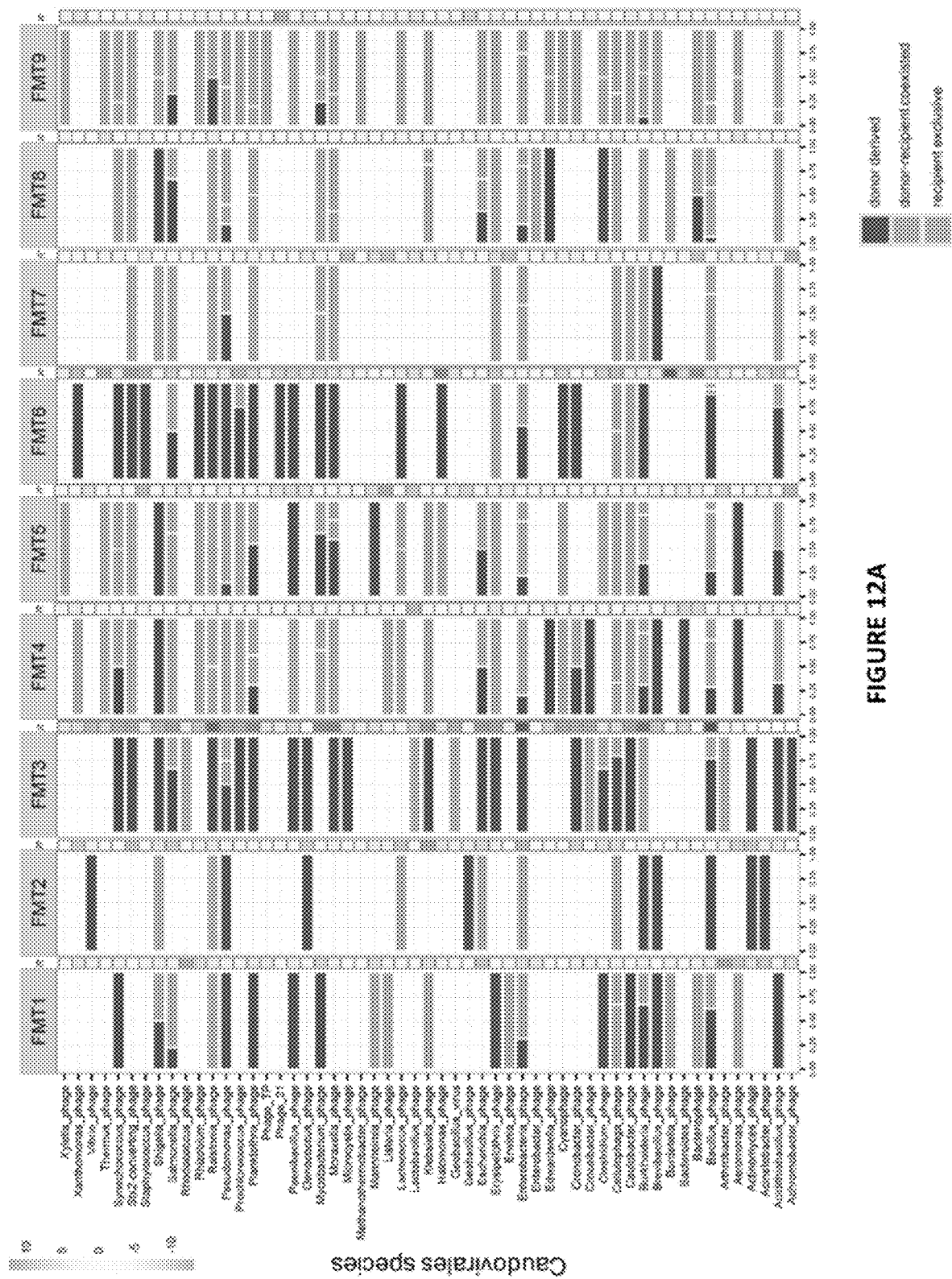
FIGS. 12A-12B Transfer of donor contigs with respect to each Caudovirales species and its relationship with post-FMT abundance alterations and donor species abundances (FIG. 12A) Proportion of presence of contigs within each Caudovirales species in the last follow-up samples after FMT, as depicted in the horizontal bars, and heatmap of the post FMT alterations of Caudovirales species abundance, as depicted in the vertical bars. "fc" stands for log 2 transformed fold change post FMT. The color of the bar indicates the origin of the Caudovirales contigs. Purple indicates donor-derived contigs colonized in the recipient, orange indicates contigs exclusively present in the recipient but not in the donor, while green indicates contigs present both in donor and in recipient.
Figure 12B:
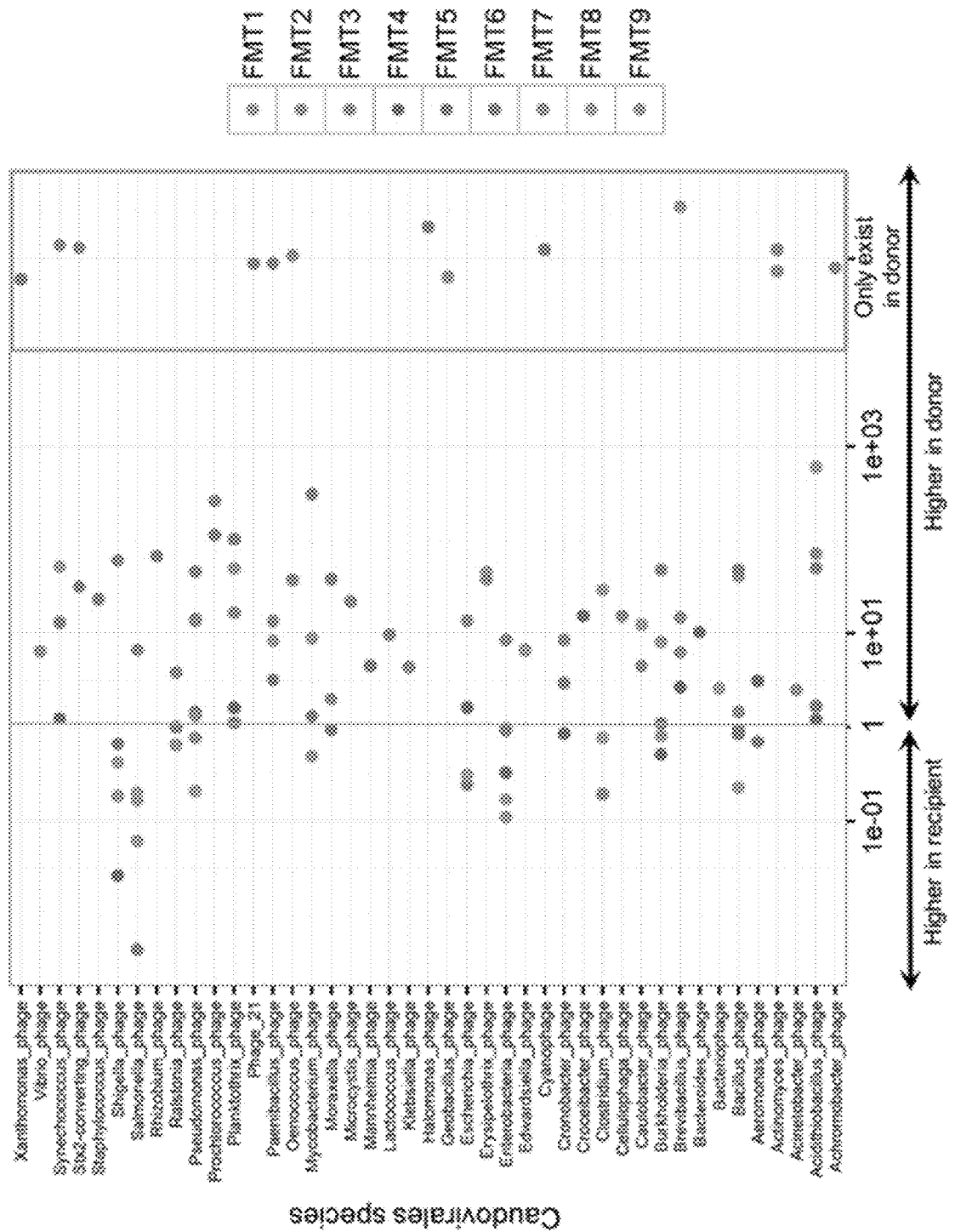

The presence of donor-derived contigs within each Caudovirales species was further assessed along with the change in the abundance of these species after FMT. FMT responders acquired more donor-derived contigs within the Caudovirales species when compared with non-responders (FIG. 12A). Not all the relative abundance of Caudovirales species was significantly enhanced with the colonisation of corresponding Caudovirales contigs from the donor (FIG. 12A), which indicates that the newly formed Caudovirales ecosystem post FMT was based on a more intricate interaction network. Furthermore, not all transfer of Caudovirales contigs from donor was dependent on a high donor-to-recipient ratio of abundance of species (FIG. 12B).

Virome Alterations in Patients with CDI after Vancomycin Treatment

Figure 1C:
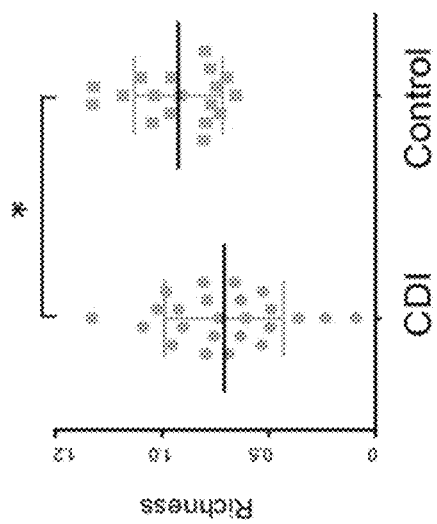
Figure 1B:
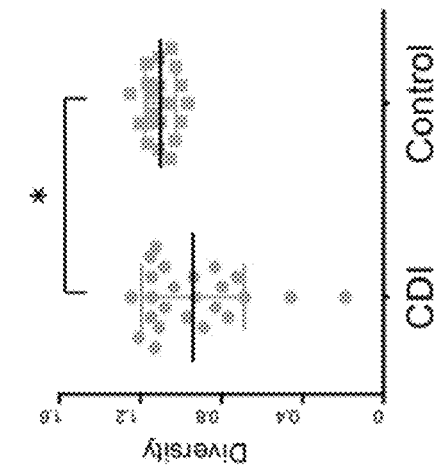
Figure 1E:
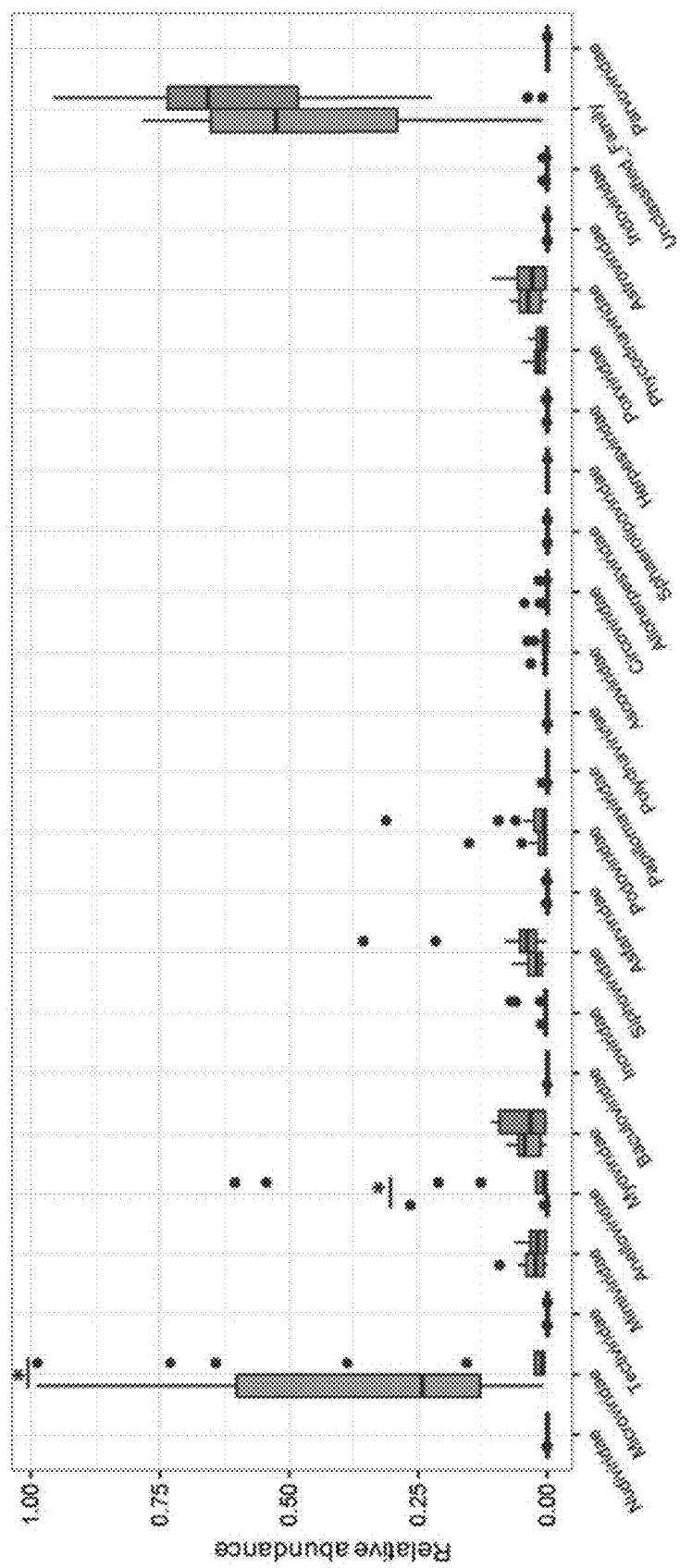
Figure 1F:
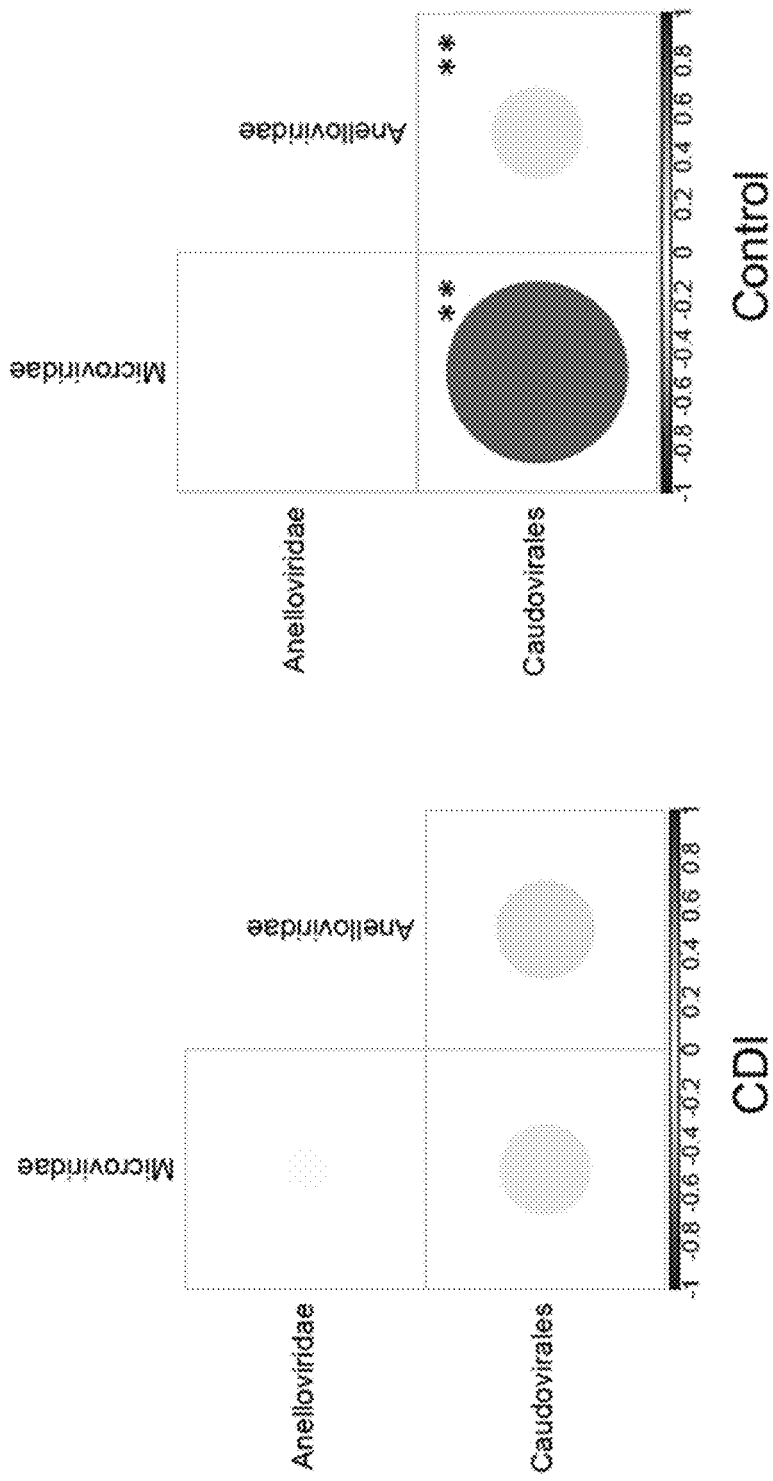
Figure 13A:
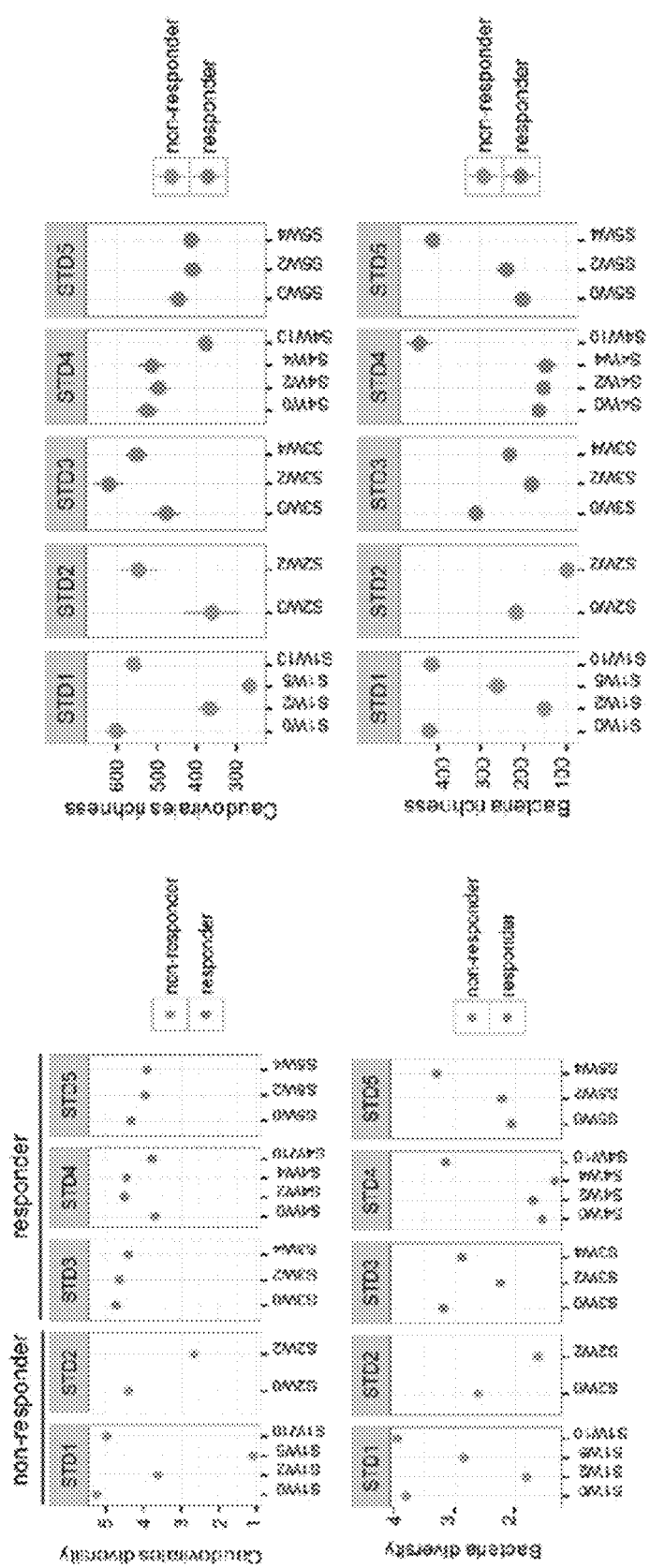
FIGS. 13A-13D Alterations in the diversity and richness of Caudovirales virome and bacterial microbiome in patients treated with vancomycin.
Figure 13B:
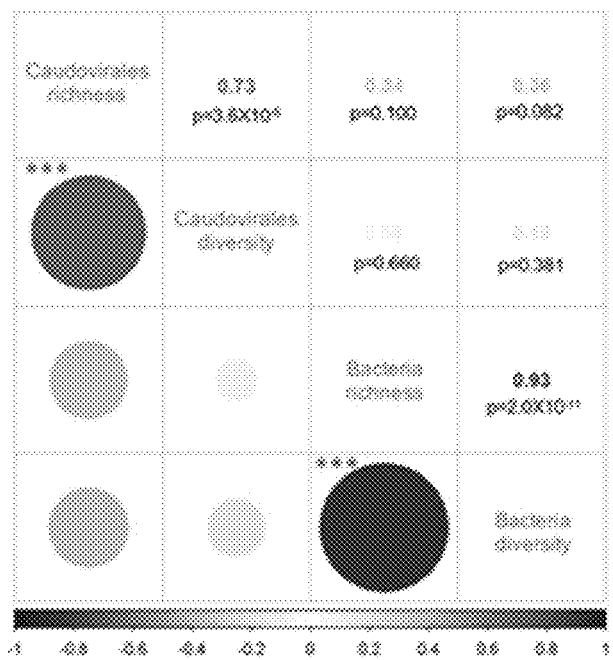
Figure 13B:
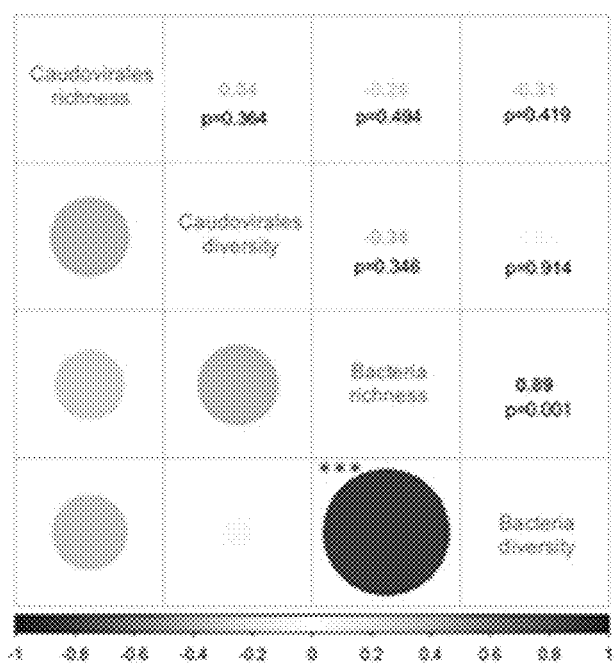
Figure 13C:
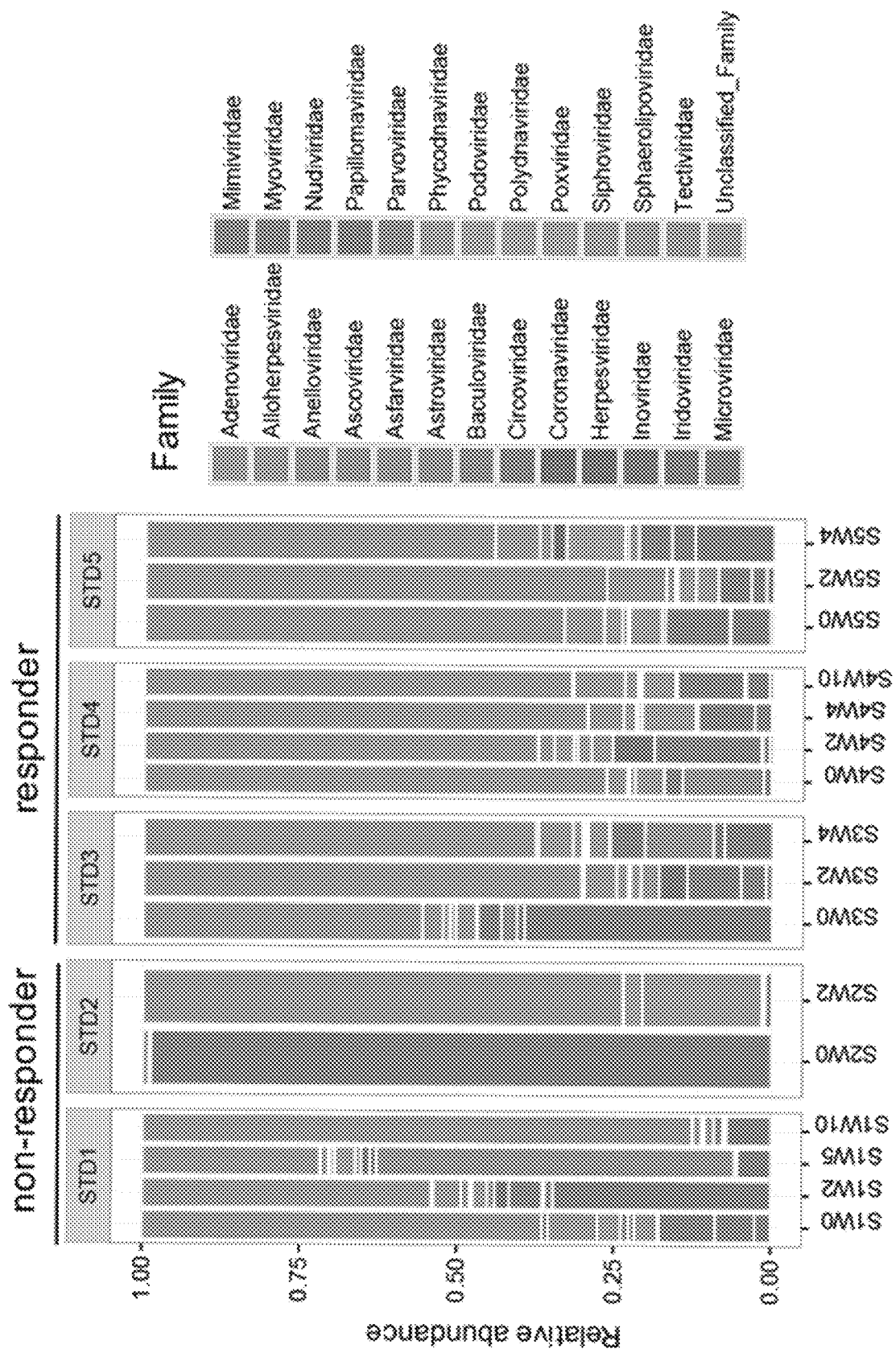
Figure 13D:
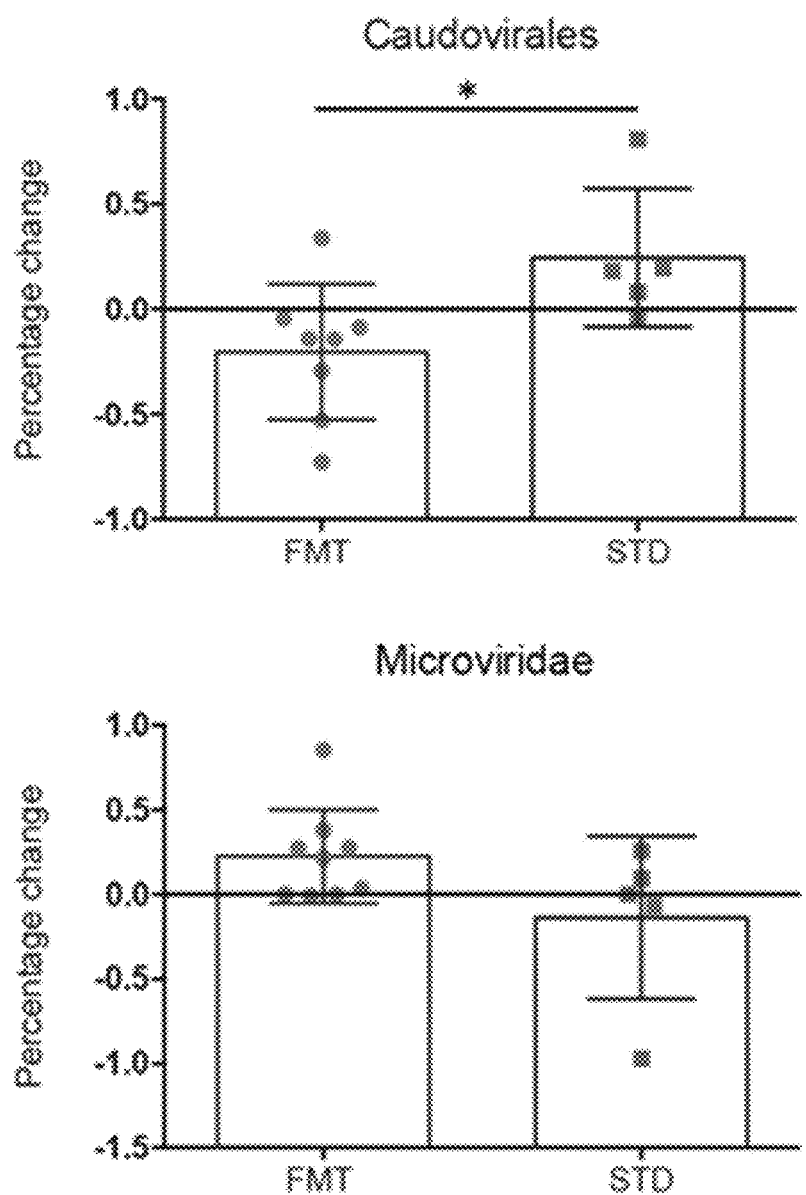
Figure 14:
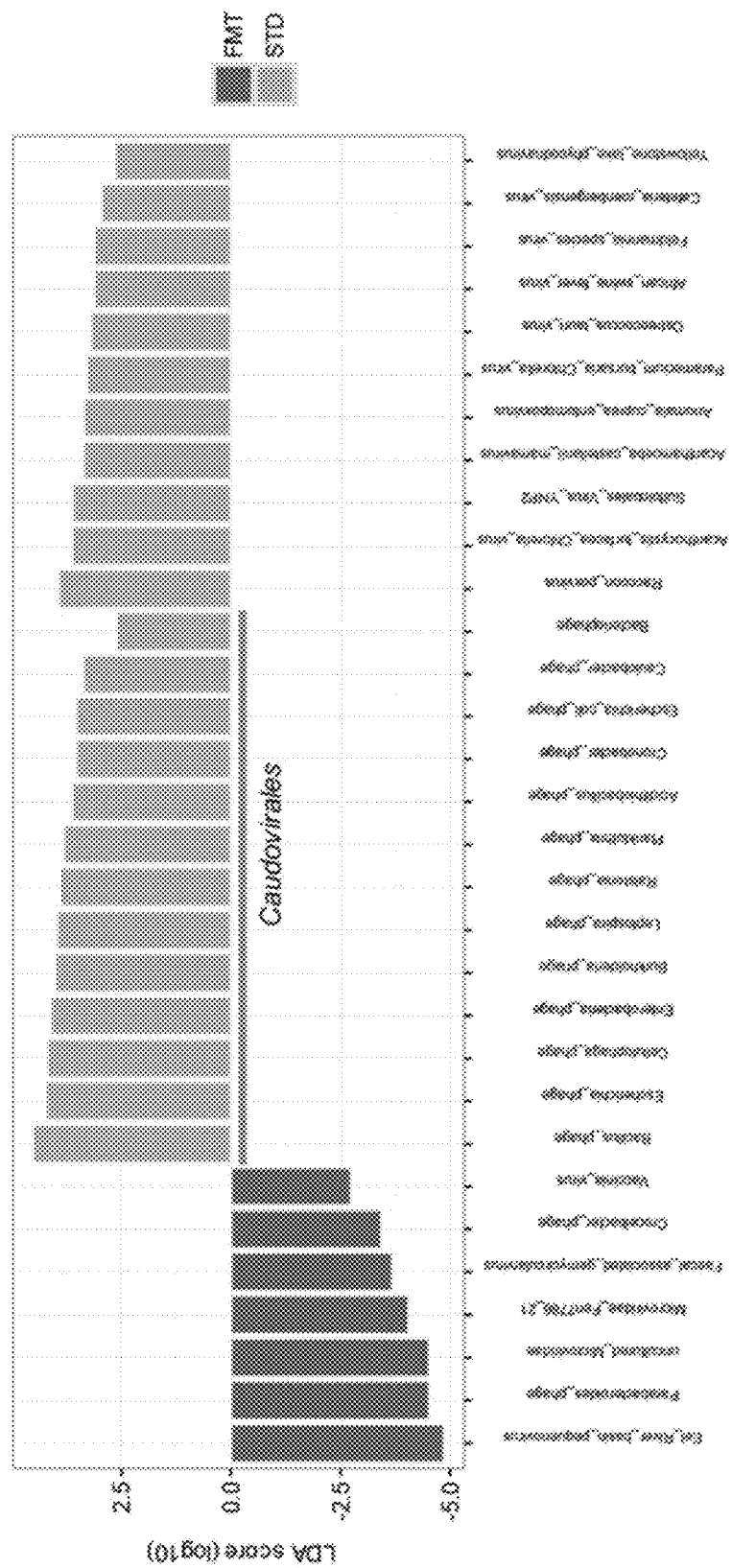
FIG. 14 Differentially enriched viral species in FMT and STD treated patients after treatment. Patients with treatment responses were compared by LefSe analysis across all the corresponding follow-up samples between FMT responders and STD responders. Only taxa with LDA score >2 and q value <0.05 are shown.

The impact of vancomycin treatment (STD) on the virome and bacterial microbiome was assessed in five patients with CDI (FIG. 1A, Table 1). In subjects who responded to vancomycin (STD3, STD4, STD5), there was no significant change in the Caudovirales diversity or richness (FIG. 13A), suggesting that antibiotics may have minimal effect on Caudovirales community. In subjects who did not respond to vancomycin (STD1 and STD2), there was substantial fluctuation in Caudovirales diversity and richness as well as bacterial diversity and richness over the course of vancomycin treatment. A significant correlation between bacterial diversity and richness was observed in vancomycin responders. In FMT responders, a correlation was found between Caudovirales diversity and richness as well as a correlation between bacterial diversity and richness (FIG. 13B). Moreover, marginally significant inverse correlations were observed between Caudovirales richness and bacterial diversity, and between Caudovirales richness and bacterial richness in patients after FMT but not after vancomycin treatment. These data indicate that FMT has a synergistic effect on both the bacterial and viral component of the gut microbiome whereas vancomycin may predominantly affect the bacterial microbiome. Taxonomical analysis was performed to further elaborate the effects of vancomycin on the virome community. In CDI subjects who responded to vancomycin, the virome structure was not significantly altered over time, whereas marked oscillation of the virome was seen in subjects who did not respond to vancomycin (FIG. 13C). Moreover, Caudovirales abundance was increased after vancomycin treatment, but decreased after FMT (FIG. 13D). To define the differentially enriched viral species between FMT and vancomycin responders, a LEfSe analysis was implemented across all the follow-up samples of treatment responders. A multitude of overpresented viral species was observed in the vancomycin samples, and nearly half of them belonged to Caudovirales (FIG. 14).

Figure 5A:
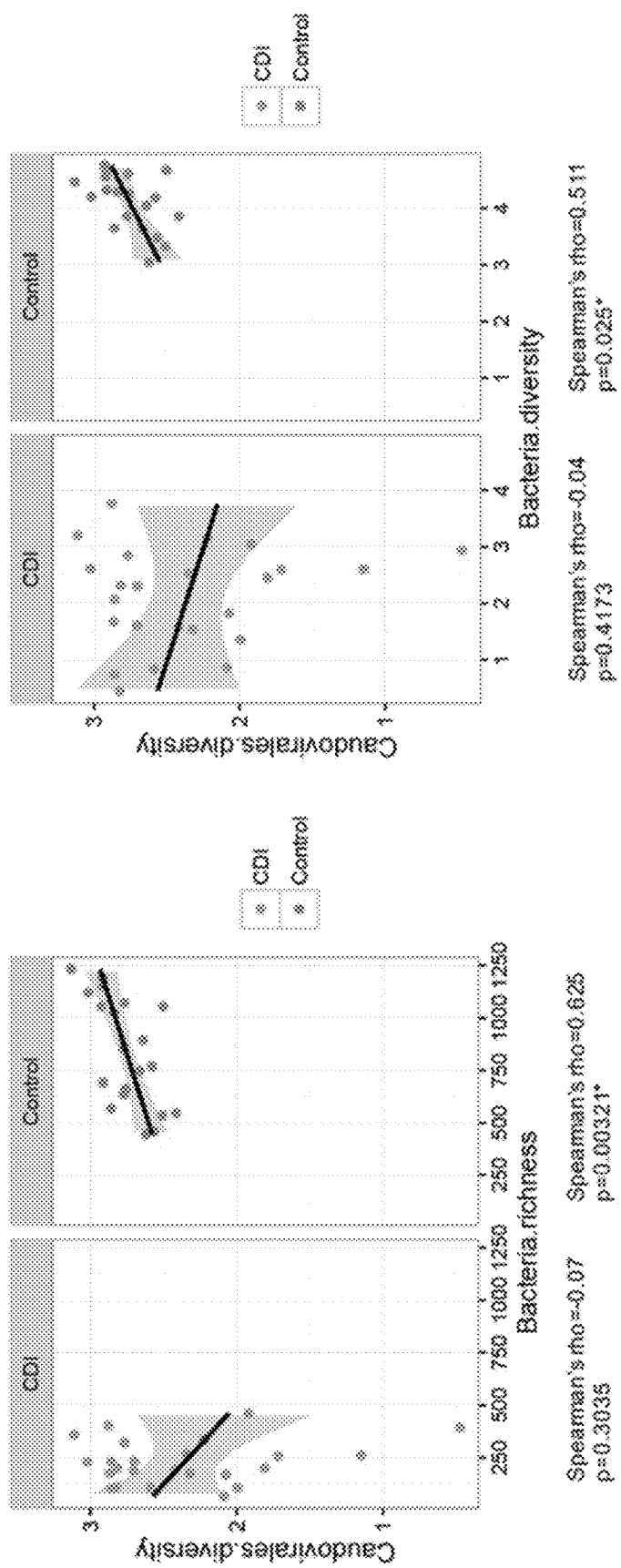
FIGS. 5A-5C Bacteria-Caudovirales relationship pattern (FIG. 5A) The correlation of bacteria richness with Caudovirales diversity and bacteria diversity with Caudovirales diversity in Clostridium difficile infection (CDI) and controls, respectively. Linear regression ±95% CI, Spearman correlation coefficient and p value are shown.
Figure 5B:
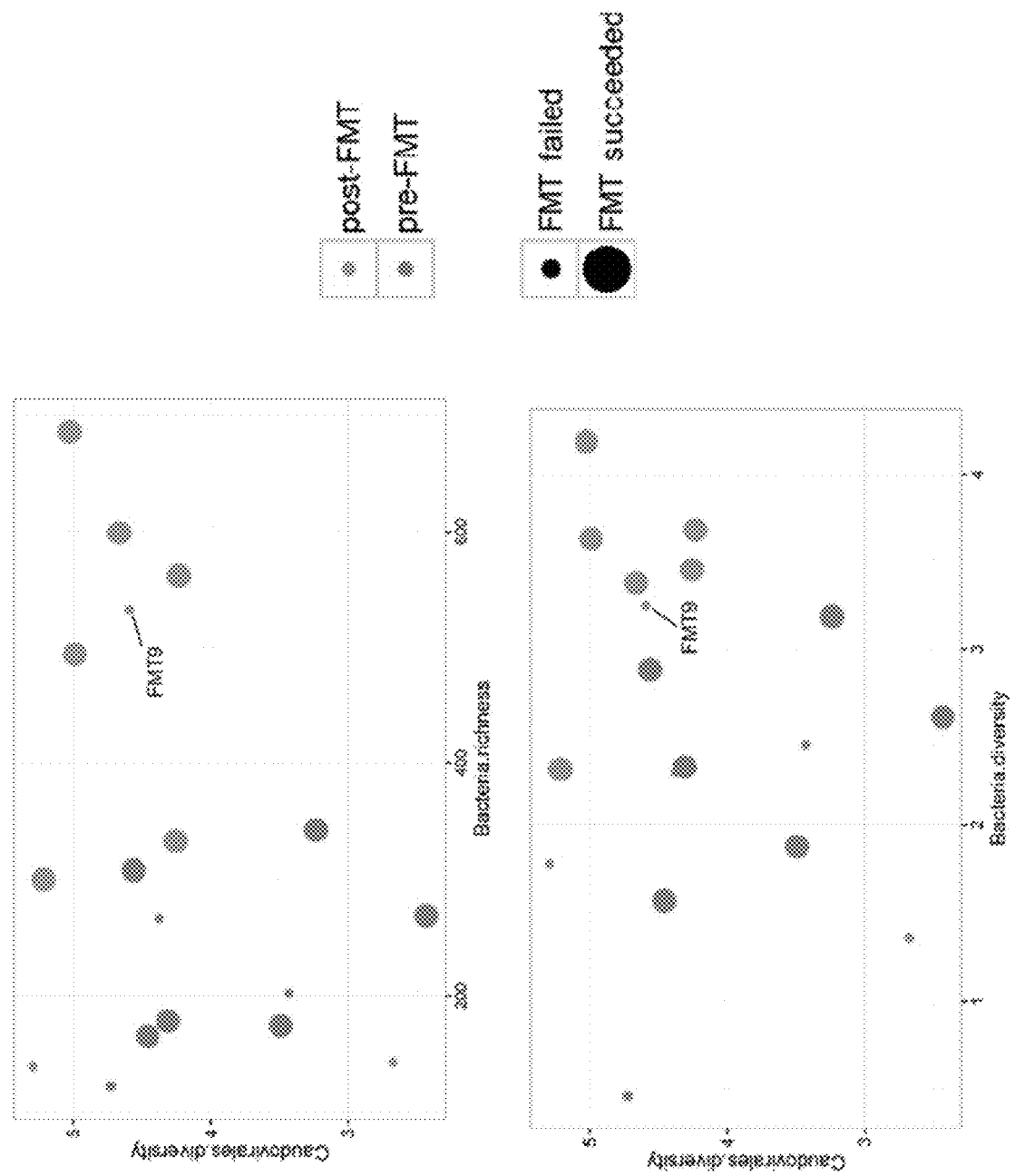
Figure 15:
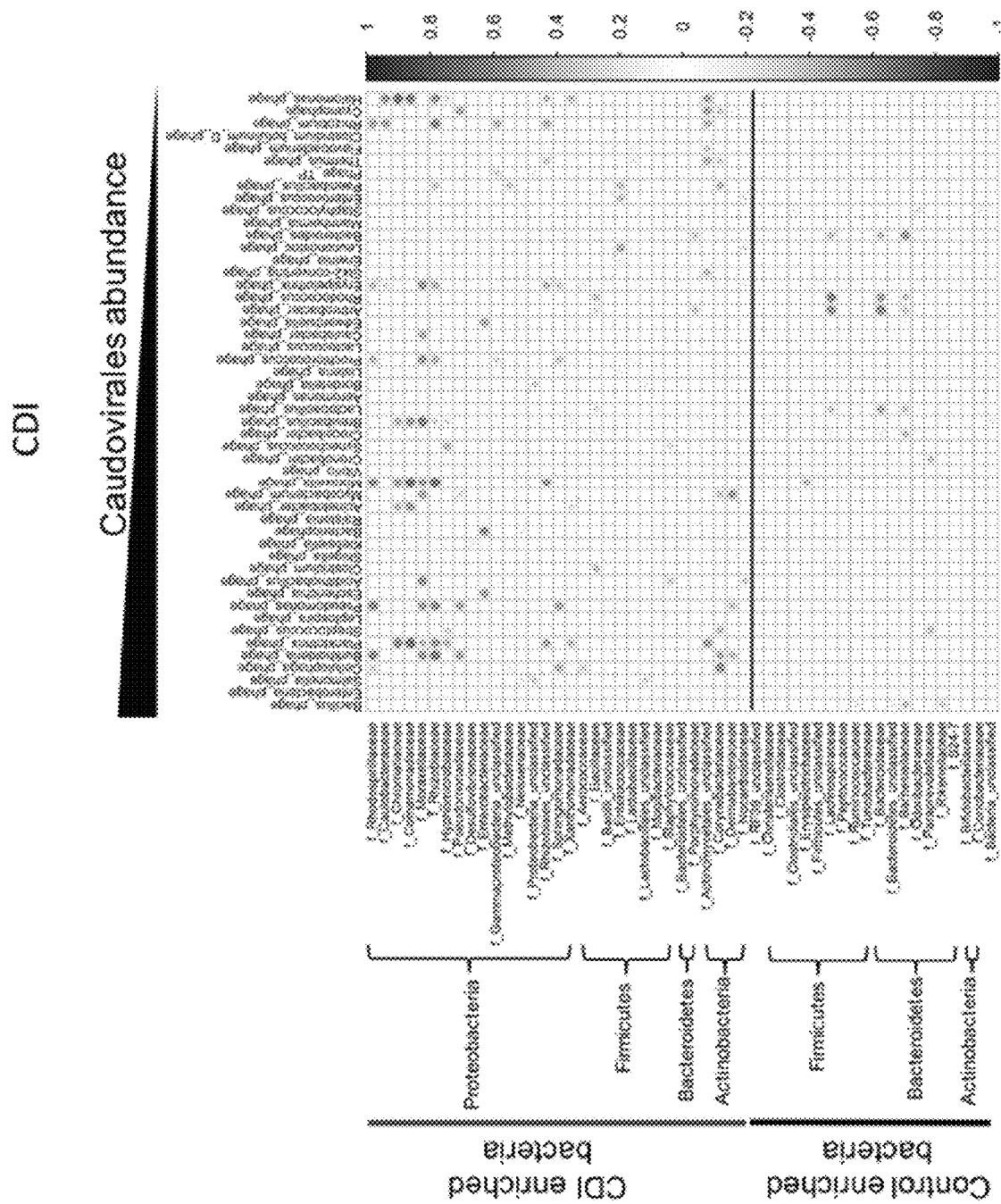
FIG. 15 Spearman correlation plots of the relative abundances of Caudovirales species and bacterial families identified to be significantly associated with CDI and controls. Statistical significance was determined for all pairwise comparisons; only significant correlations (p value <0.05) are displayed. Statistical significance was determined for all pairwise comparisons; significant correlations (p value <0.05) are displayed with asterisk. Blue circles and positive values indicate positive correlations, red circles and negative values indicate inverse correlations. The size and shading indicate the magnitude of the correlation where darker shades are more correlated than lighter ones.
Figure 15:
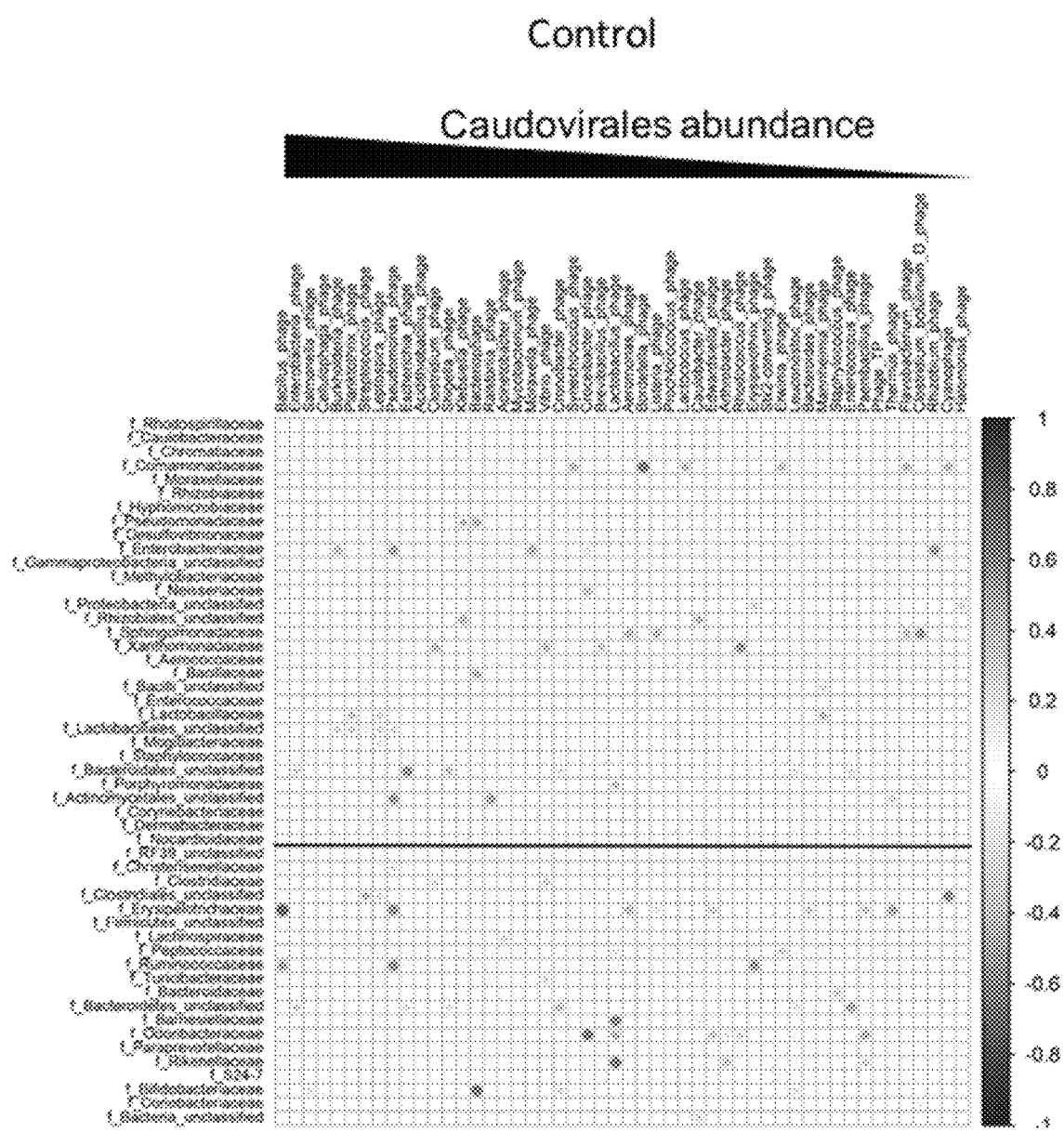

Virome and Bacterial Microbiome Interactions in Patients with CDI Before and after FMT To characterise the relationship between the configuration of virome and that of the bacterial microbiome, the correlation of the diversity and richness of Caudovirales with that of bacterial communities was evaluated in household controls and in patients with CDI. In controls, there was a significant correlation between Caudovirales diversity and bacterial diversity (Spearman's $\rho=0.511$, $p<0.05$), and between Caudovirales diversity and bacterial richness (Spearman's $\rho=0.625$, $p<0.05$) (FIG. 5A). However, these correlations were distorted in CDI. After FMT, a shift of the microbiome community from a low to high bacterial richness and diversity was demonstrated, and from a low to a high Caudovirales diversity (FIG. 5B). The microbiome of FMT non-responders changed less when compared with FMT responders. The temporal restoration of bacterial structure over the period of follow-up in subject FMT9 indicated bacterial reset, but disease recurrence at week 28 may be associated with unaltered virome structure after FMT. The correlation of Caudovirales species with bacterial families was further assessed in CDI subjects and controls. More positive correlations, particularly of bacterial families Proteobacteria and Actinobacteria with Caudovirales species, were found in CDI than in controls (FIG. 15). This corresponded with an increase in the relative abundance of these bacterial taxa in patients with CDI together with an overpresentation of Caudovirales taxa compared with controls. Among the Caudovirales taxa positively related to Proteobacteria, predominant bacteriophage species comprise *Burkholderia phage, Planktothrix phage, Pseudomonas phage, Moraxella phage* and *Halomonas phage*.

Figure 5C:
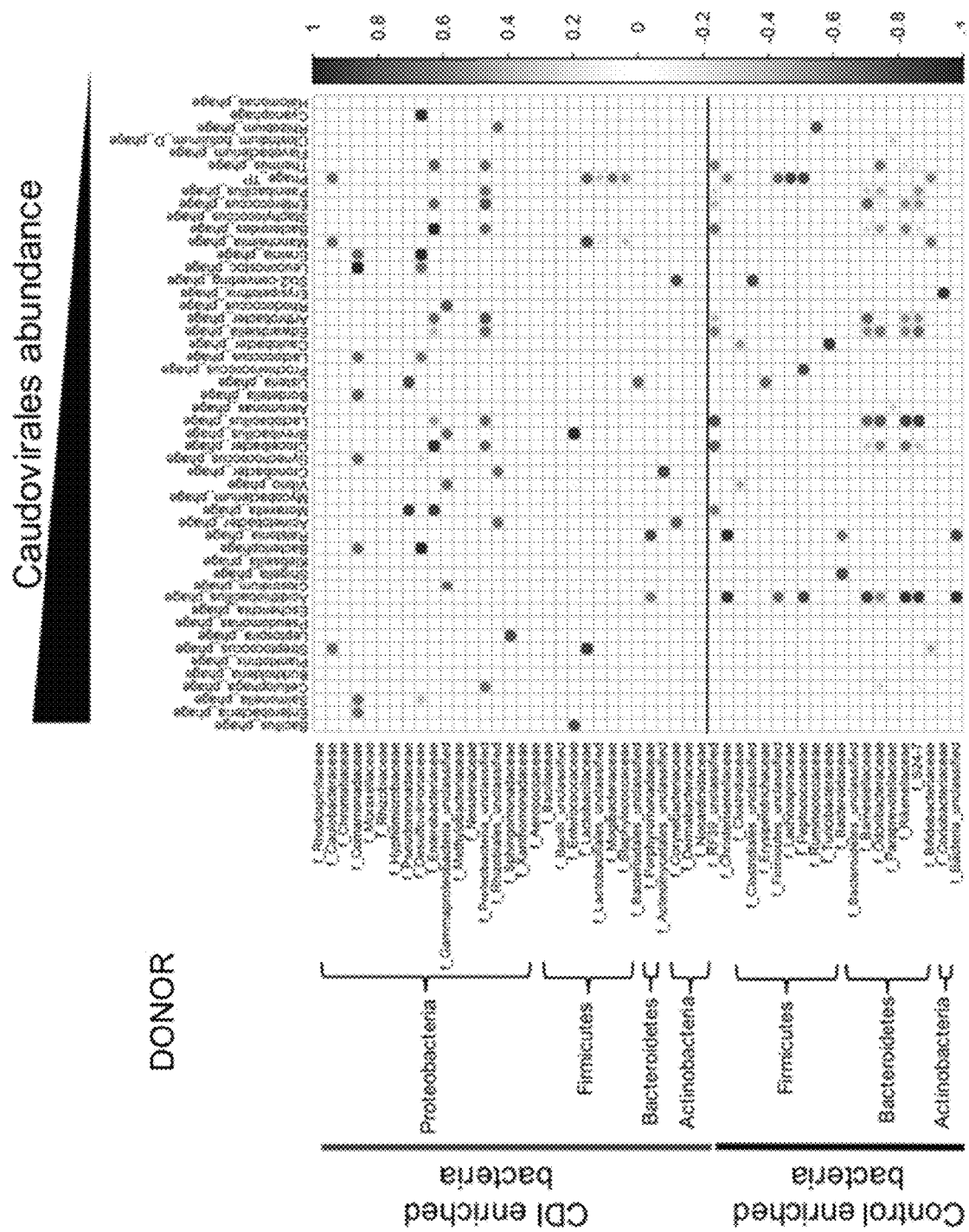
Figure 5C:
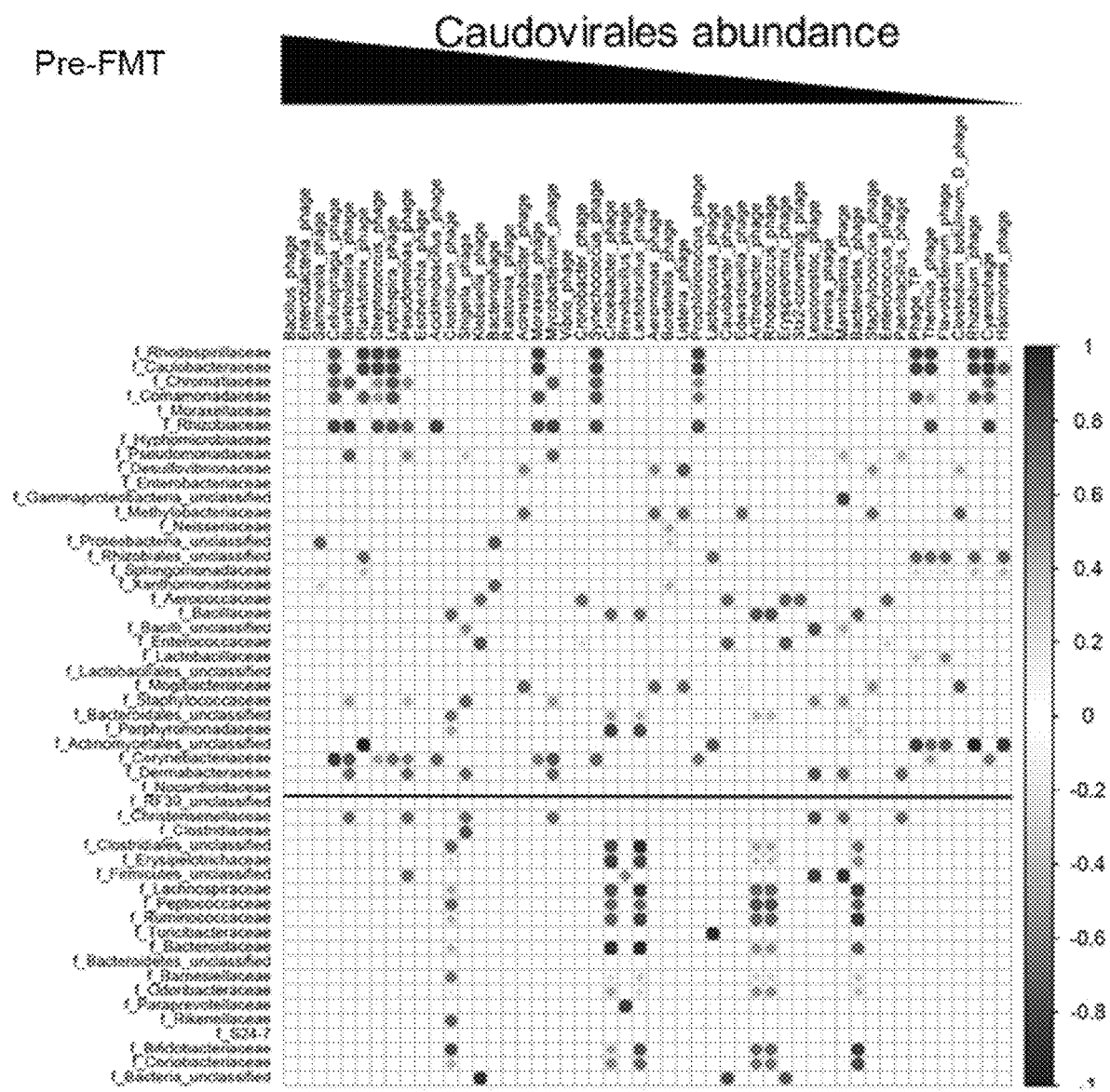
Figure 5C:
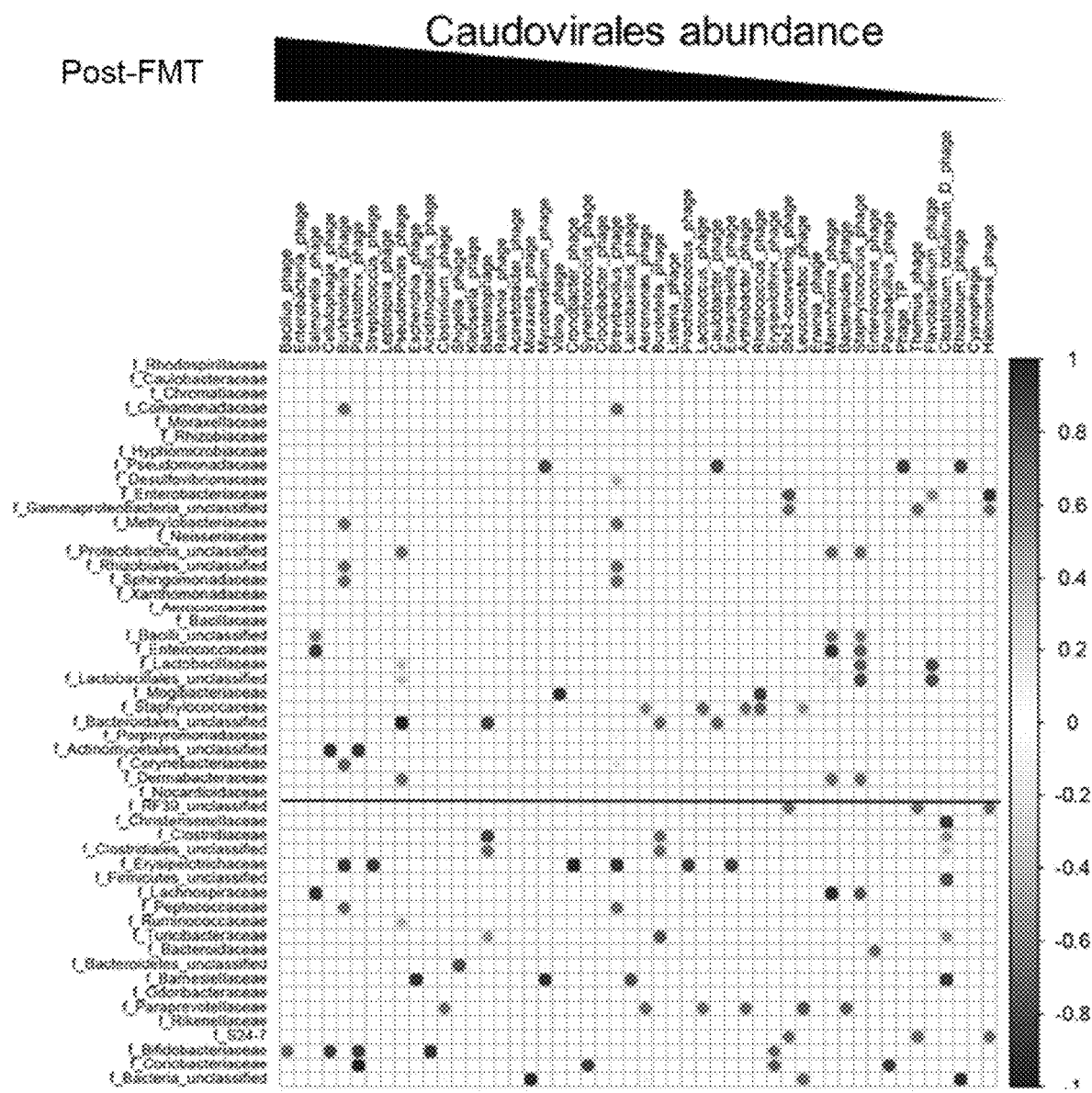

Alterations in the bacteria-Caudovirales relationship was lastly investigated in FMT responders. Pre-FMT samples showed a mutualistic relationship, particularly of Proteobacteria-Caudovirales and Actinobacteria-Caudovirales (FIG. 5C). However, a contraction of the number of significant correlations after FMT was observed between CDI-enriched bacteria and Caudovirales taxa. Interestingly, a few inverse correlations emerged after FMT, further implicating the importance of a 'favourable' virome-bacterial microbiome relationship. These results suggest a distinct virome-bacterial microbiome relationship before and after FMT treatment.

Discussion

To date, this study represents the most in-depth human gut virome study of FMT. In this pilot observational study, the present inventors showed that patients with CDI exhibited a state of enteric virome dysbiosis, characterised by an increased Caudovirales abundance and a decreased Caudovirales diversity, richness and evenness. The mechanism underlying the efficacy of FMT has been attributed to improved microbial diversity with re-establishment of a 'normal' bacterial microbiota as a host defence against *C. difficile*.[2,3] Recently, Ott and colleagues showed that sterile faecal filtrate transfer was effective in treating five subjects with CDI, which highlights the therapeutic potential of other components including bacteriophages within the fecal matters other than bacteria.[15] In this preliminary study, the observation that disease cure was associated with Caudovirales bacteriophage colonisation and donor Caudovirales richness provides new insights into the potential importance of virome derived from donor that may influence treatment outcome. These data further highlight a new concept to FMT in that bacteriophages may be critical components of FMT. Bacteriophages have the potential to alter the composition and function of host microbiota and influence treatment outcomes. In particular, correlations between specific bacteriophages and bacteria shown in this study appeared to be associated with the outcome of FMT in CDI.

Among the enteric virome, Caudovirales is the most abundant taxon.[17,20] Studies have shown that enteric Caudovirales were associated with intestinal inflammation although the underlying mechanisms remain largely unknown.[17,21] Patients with IBD have been shown to have a significantly higher Caudovirales richness than healthy household controls,[17] which is in contrast with the decreased Caudovirales richness observed in CDI subjects. Virome dysbiosis seen in CDI appeared to be disease specific and was not observed in stool of subjects with norovirus-associated diarrhoea. Unlike the high cure rate of FMT in CDI, only up to a quarter of patients with UC, a subtype of IBD, achieved a sustained response with FMT.[22-24] One plausible hypothesis is that a higher Caudovirales richness in donor than diseased recipient is important for FMT efficacy. In line with this hypothesis, it was found that when donor Caudovirales richness was higher than that of the recipient, all the recipients responded to FMT, while more than half of the recipients whose Caudovirales richness was higher than that of the donor (three out of the five) experienced disease recurrence after FMT treatment. This finding suggests a donor effect of FMT efficacy and highlights that future FMT therapy should take into consideration detailed characterisation of donor and recipient fecal virome, although these findings need to be confirmed in a larger cohort. As this study has a modest sample size, and causation between donor Caudovirales richness, transfer of bacteriophages and FMT treatment outcome was not completely proven, it remains unclear whether altered bacteriophages represent a primary or secondary phenomenon. Understanding how Caudovirales bacteriophage transfer and donor virome richness affect FMT responses in CDI could help illustrate their effects for treatments of other human diseases.

Activated phages can drive disease by reducing bacterial diversity and spreading virulence factors and antibiotic resistance.[25] The expansion of Caudovirales abundance in CDI could arise from the induction of prophage from commensal microbes, according to the 'predator-prey' model by Lotka-Volterra in which bacterial *phage* prey on bacteria resulting in the release of bacteriophages after bacteria enter into the lytic cycle.[26,27] Disparately expanded Caudovirales taxa may lead to decreased diversity and evenness in CDI compared with that in controls. Correlation of CDI-enriched bacteria with Caudovirales species in CDI and a reset of correlation after FMT indicate a 'kill-the-winner' dynamics, where upregulated Caudovirales bacteriophages were observed with the overpresentation of certain bacterial taxa enriched in CDI.[28] The data showed that restoration of a balanced relationship between bacterial microbiome and virome is important after FMT. It is notable that virome alterations in concert with bacterial changes after FMT may influence the efficacy of FMT in CDI.

Many patients with CDI often undergo multiple rounds of antibiotic therapy before undergoing FMT. This may lead to *phage* activation and act as a confounder. However, this scenario is unlikely as subjects on vancomycin were included as a control group and the virome showed little variation over the course of treatment in subjects who responded to vancomycin.

This observational study had a modest sample size. Nonetheless, it represents the largest study to date that comprehensively followed CDI subjects after FMT and assessed in-depth virome alterations in association with clinical outcome. Importantly, this study provides detailed insight into the dynamics of interactions between viruses and bacteria in the intestine during FMT therapy. Sustained intestinal viral dysbiosis after FMT, due to limited amount of Caudovirales transfer from the donor, could be a potential factor that predisposes patients towards disease recurrence. These findings contribute to knowledge in the field on 'optimal' donor selection and highlight that future FMT therapy may consider detailed characterisation of donor and recipient fecal virome.

In conclusion, this pilot study showed that treatment response in FMT was associated with a high colonisation level of donor derived Caudovirales taxa in the recipient, especially when Caudovirales richness in the donor was higher than that of the recipient. The data suggest that establishing a bacteria and virome structure that more closely resembles that of healthy controls through FMT may be important to eradicate CDI.

Methods

Study Subjects and Treatment Outcome

The current study was a substudy from a randomised controlled trial (RCT) of FMT versus vancomycin for patients with CDI. Consecutive CDI subjects enrolled into this RCT were invited to participate in a substudy of assessment of fecal microbiota. Patients were included if they had three or more loose or watery stools per day for at least two consecutive days, or eight or more soft or loose stools in 48 hours, and a positive stool test for *C. difficile* based on a two-step testing algorithm in the hospital, a positive GDH (glutamate dehydrogenase) screening test followed by a positive PCR test of *C. difficile*. A total of 24 subjects with CDI and 20 healthy household controls were recruited, and stool samples at baseline were obtained for analyses of virome and bacterial microbiome. Among them, 14 CDI subjects consented to have stool samples collected serially after treatment for microbiome analysis. Nine CDI subjects were treated with FMT and five were treated with vancomycin, and they were followed up at baseline and weeks 2, 4, 10 and 16 after treatment (FIG. 6). One patient FMT6 had recurrent CDI. This patient had five previous episodes of CDI prior to FMT. Subjects in the FMT group received 5 days of vancomycin followed by donor-infused stool via nasojejunal route, and those who had standard therapy (STD) received oral vancomycin 500 mg four times per day for 10 days. A computer-generated randomisation schedule was used to assign patients to the treatment sequences. All patients kept a stool diary and were questioned about stool frequency and consistency and medication use.

Treatment response was defined as an absence of diarrhoea or persistent diarrhoea that could be explained by other causes with a negative stool test for *C. difficile* toxin, while relapse was defined as diarrhoea with a positive stool test for *C. difficile* toxin. Treatment cure is defined as symptom resolution and a negative *Clostridium difficile* toxin in stool until the last follow-up (last follow-up was referred to as the last stool collection time point, as shown in FIG. 6). Six of the nine subjects who had FMT (FMT1-FMT6) and three of the five patients (STD3-STD5) who had vancomycin were cured of CDI (termed responders, Table 1) at a median follow-up of 16 weeks. CDI recipients FMT8 and FMT9 shared the same donor, and this donor was termed 'D8'. Clinical data of the subjects and collected stool samples are shown in table 2. None of the patients had received antibiotics or proton pump inhibitors after FMT.

VLPs Enrichment and Sequencing

VLPs were enriched from pulverised human stool, using a protocol according to previously described methods.[11,17] VLP DNAs were quantified (NanoDrop), and 1 μg of DNA was randomly fragmented by ultrasonication (Covaris) followed by library construction. The qualified libraries were amplified on cBot to generate the cluster on the flow cell (TruSeq PE Cluster Kit V3-cBot-HS, Illumina). The amplified libraries were sequenced paired end on the HiSeq 2000 System (TruSeq SBS KIT-HS V3, Illumina) (BGI, Shenzhen, China; standard 2×150 bp run), generating 20-60 million raw sequences (5-8 G raw data) per sample (sequence statistics in Table 3). Sequence processing and quality control, de novo contig assembly and taxonomy annotation were performed.

Virome Data Analysis

To estimate contig abundance and calculate sequence diversity, all reads were aligned to the resulting contigs using Bowtie2 (V. 2.2.9).[18] The mapped sequence counts, contig lengths and total sequence counts were used to normalise the sequence counts and represent the RPKM (reads per kilobase per million) of each sample to the contigs. These values were used to generate an operational taxonomic unit (OTU) relative abundance table, which was annotated with the taxonomy described above. The virome abundance data were imported into R 3.2.3. Richness, diversity and rarefaction calculation were performed using the estimated richness function of the phyloseq package. Diversity and richness plots were generated in GraphPad Prism (V. 6.0). Spearman correlations and their significance were calculated using the cor and cor.test functions in R, respectively. For the Caudovirales-bacterial taxa comparisons, Spearman correlations were calculated for the relative abundance of the 50 most abundant Caudovirales and the bacterial families determined to be significantly associated with disease by LEfSe analysis. Correlation plots were generated using the corrplot R package. Heat maps were generated using the pheatmap R package. LEfSe linear discriminant analysis and multivariate analysis were performed.

Species and Contig Presence

To establish the presence of a species or a contig within a sample, the RPKM of a contig or a species is set to be >2 (a stringent criteria), so as to rule out the false-positive finding) for the contig or the species to be assured as present within a sample. In samples after FMT, if a contig or a species was not present in the recipient baseline sample but present in the corresponding donor baseline sample and in the recipient post-FMT sample, the contig or species was defined as 'donor-derived'; if a contig or a species was not present in the corresponding donor baseline sample but detected both in the recipient baseline sample and in the recipient post-FMT sample, the contig or the species was defined as 'recipient-exclusive', if a contig or a species was present across the recipient baseline sample, the recipient post-FMT sample and the corresponding donor baseline sample, the contig or the species was defined as 'donor recipient coexisted.' To determine the abundance alteration of Caudovirales species after FMT, the species' relative abundance (RA) fold change was defined as fc=log 2(post-FMT last follow-up RA/pre-FMT baseline RA).

Study Design

Patient Inclusion Criteria:

1. *C. difficile* infection was defined as diarrhea (≥3 soft, loose or watery stools per day for at least 2 consecutive days or ≥8 soft or loose stools in 48 hours) and a positive stool test for *C. difficile* toxin; and 2. Age ≥18; and 3. Written informed consent obtained Patient Exclusion Criteria:

1. The presence of human immunodeficiency virus (HIV) infection with a CD4 count of less than 240

2. Pregnancy

3. GI Bleeding

4. Acute coronary syndrome

Donor Screening:

Donors included individuals who are spouses or partners, first-degree relatives, other relatives, friends, and individuals unknown to the patient. They were screened with a questionnaire and excluded if they had taken antibiotics within the preceding 3 months; were on major immunosuppressive agents, including chemotherapeutic agents; had known or recent exposure to HIV, hepatitis B or C; had a current communicable disease; participated in high-risk sexual behaviors; used illicit drugs; traveled within 6 months to areas with endemic diarrheal illnesses; or had history of inflammatory bowel disease, irritable bowel syndrome or chronic diarrhea, gastrointestinal malignancy or polyposis. In addition, donor was screened for HBsurface Ag, Anti-HBc, Anti-HCV, Anti-HIV, Syphilis EIA, stool microscopy, culture and sensitivity, stool cyst, ova, parasite, norovirus and *C. difficile* (cytotoxin and PCR assay). All subjects and collected stool samples are listed in Table 2.

The donors for the FMT group were healthy household controls and the donor stool samples analyzed were the same samples used for FMT. All subjects provided written informed consent. The study was approved by The Joint Chinese University of Hong Kong, New Territories East Cluster Clinical Research Ethics Committee (The Joint CUHK-NTEC CREC, CREC Ref. No.: 2014.183-T; Clinical Trial registry, NCT02570477).

Family members provided donor stool for subjects randomised to FMT arm. Cure after FMT or vancomycin therapy was defined as symptom resolution and negative *Clostridium difficile* toxin in stool at last follow-up by PCR assay. Relapse was defined as diarrhea with a positive stool test for *C. difficile* toxin.

There is no pre-specified effective sample size for virome analysis. However, studies with as minimum as 4 twin pairs [20, 29] were able to define longitudinal changes in virome, therefore for this study nine subjects in the FMT arm and five in the standard antibiotic treatment (vancomycin) group respectively were expected to be sufficient.

This was a randomised but not blinded study. However for virome and bacterial microbiome analyses on stool samples, metagenomics assessments were initially performed by analysts who were blinded to the clinical outcome of the studied subjects. When the profiled virome and bacterial microbiome data were available for each individual subject, correlation was then made to associate microbiome profiles with treatment outcomes of subjects.

Infusion of Donor Stool

In subjects who received FMT, a nasoduodenal tube was inserted with radiology guidance. Donor feces was diluted with 500 ml of sterile saline (0.9%), blended and the supernatant was strained with filter paper and poured in a sterile bottle. Within 6 hours after collection of feces by the donor, the solution was infused through a nasoduodenal tube (2 to 3 minutes per 50 ml). The tube was removed 30 minutes after the infusion, and patients were monitored for 2 hours. In subjects with received FMT, a minimum of 50 g of donor stool was collected on the same day of infusion and used within 6 hours of collection.

Subjects with Norovirus Infection and Fecal Viral Metagenomic 66 Sequence Data 17 patients with acute infectious diarrhea from confirmed norovirus infection (NI) [Median age, 69 years, IQR, 42-83) and a similar number of age- and gender-matched healthy controls were included. Stool samples were collected for Virus-like Particles (VLPs) enrichment and metagenomic sequencing. All subjects provided written informed consent. The study was approved by The Joint Chinese University of Hong Kong, New Territories East Cluster Clinical Research Ethics Committee (The Joint CUHK-NTEC CREC, CREC Ref. No.: CREC-2016.445).

Virus-Like Particles (VLPs) Enrichment

Approximately 200 mg of stool was suspended in 400 µl saline-magnesium buffer (0.1 M NaCl, 0.008 M $MgSO_4$-$7H_2O$, 0.002% gelatin, 0.05 M Tris pH7.5) by vortexing for 10 min. Stool suspensions were then cleared by centrifugation at 2,000×g to remove debris and cells. Clarified suspensions were passed through one 0.45 mm followed by two 0.22 mm filters to remove residual host and bacterial cells. Samples were treated with lysozyme (1 mg/ml at 37° C. for 30 min) followed by chloroform (0.2× volume at RT for 10 min) to degrade any remaining bacterial and host cell membranes. Non-virus protected DNA was degraded by treatment with a DNase cocktail (10 U Turbo DNaseI (Ambion), 1 U Baseline zero DNase (Epicenter)) followed by heat inactivation of DNases at 65° C. for 10 min. VLPs were lysed (4% SDS plus 38 mg/ml Proteinase 86 K at 56° C. for 20 min), treated with CTAB (2.5% CTAB plus 0.5 M NaCl at 65° C. for 10 min), and nucleic acid was extracted with phenol:chloroform pH 8.0 (Invitrogen). The aqueous fraction was washed once with an equal volume of chloroform, purified and concentrated on a column (DNA Clean & Concentrator™-5, Zymo Research). VLP DNA was amplified for 2 hr using Phi29 polymerase (GenomiPhi V2 kit, GE Healthcare) prior to sequencing. To reduce amplification bias, four independent reactions were performed for each sample and pooled together afterwards.

Sequence Processing and Quality Control

Raw reads were filtered by SOAPnuke (v 1.5.3) (web site: soap.genomics.org.cn/) developed by BGI as follows: (i) adaptors removed, (ii) read removed if N base is more than 3% of the read, (iii) read removed if bases with quality low than 20 were more than 40% of read, (iv) all duplicates removed. Human sequences were removed from the quality-trimmed dataset by DeconSeq (v 0.4.3) with default parameters and the 100 human reference GRCh38 [30].

De Novo Contig Assembly and Taxonomy Annotation

Contigs were assembled using the IDBA (v 1.1.1) [31], using maximum kmer length 120, with a minimum contig length of 1,000 bp. The assembled contigs were clustered at a 95% identity level using CD-HIT [32] to generate a unique contig consortium. Open Reading Frame (ORF) were predicted and extracted from contigs using the Glimmer3 toolkit (v 3.02) [33] and a minimum length threshold of 100 amino acids. The translated amino acid sequences of predicted ORFs from the VLP contigs were matched against the standard subset of the standalone entire UniProt TrEMBL database as of Jun. 5, 2016, that contained only virus and phage reference proteins, using blastx (e<10-5) as described previously [34]. Each contig was assigned taxonomy based on the most abundant taxa contained within that contig using a voting system as described previously for virus taxonomic assignment at different taxon levels [34, 35]. The voting system first annotated each ORF of a contig of interest with the best-hit virus taxonomy. It then compared all of the taxonomic assignments of the ORFs within the contig of interest, and annotated the contig with the majority ORF assignment. Contigs with less than one ORF per 10 kb were not assigned taxonomy as this suggests a contig of only limited similarity [35]. Contigs without a majority ORF taxonomic assignment due to ties of multiple major taxa were assigned as having multiple possible taxonomic annotations. Because some contigs shared the same taxonomic identities, the contig table was collapsed by taxonomic identity, meaning the contig relative abundances were summed if they shared identity. Taxa with relative abundance under 0.01% were disregarded for the purpose of further analyses. Richness and diversity calculation were performed using the estimate_richness function of the phyloseq package and plotted in GraphPad Prism (v 6.0) at the species and contig levels.

LEfSe Linear Discriminant Analysis and Multivariate Analysis

To compare differences in the configurations of virome and bacterial microbiomes between CDI patients and healthy household controls, between FMT responders and non-responders, between FMT responders and vancomycin responders, Lefse analyses were performed on the Huttenhower lab Galaxy server (web site: huttenhower.sph.harvard.edu/galaxy/) by importing the viral and bacterial relative abundance values and associated sample metadata, with FDR adjusted p value <0.05 considered significant and effect size calculated. MaAsLin (Multivariate Analysis by Linear Models) was implemented to identify associations between clinical metadata (age, sex, family ID, time samples were collected) and viral community abundance matrix on the Huttenhower lab Galaxy server (web site: huttenhower.sph.harvard.edu/galaxy/).

Stool Bacterial DNA Extraction

Stool bacterial DNA was extracted from aliquots of human stool sample using ZR Fecal DNA miniPrep kit (Zymo Research, Orange, Calif.) according to the protocal. Briefly, 150 mg of fecal sample was added to the Bashing-BeadLysis Tube with 750 µl Lysis solution, and then processed at maximum speed for ≥5 minutes. The lysates were centrifuged at ≥10,000×g for 1 minute. The supernatant was transferred to a Zymo-Spin™ IV Spin Filter in a collection tube and centrifuged at 7,000×g for 1 minute. About 1,200 µl of fecal DNA binding buffer was added to the filtrate in the collection tube, followed by concentration and purification in a new filter tube. Finally, a total of 50 µl eluted DNA with a concentration at 20-100 ng/µl was prepared for each sample.

16S rRNA Sequencing and Quality Control

The final fecal DNA samples were sequenced on the Illumina MiSeq platform (V4 region, 2×250 bp), 112,482±66,095 (number ±SD) sequences obtained on average (sequence statistics in Table 4). Quality control and data analysis were implemented in mothur (v 1.38.0) as previously described [36]. Any sequences with ambiguous bases and anything longer than 275 bp were removed, and aligned against the non-redundant Greengenes database (v 13.8) [37] using the NAST algorithm. Any sequences that failed to align with the V3-4 region were discarded. The remaining sequences were trimmed to the same alignment coordinates over which they fully overlapped, followed by removal of homopolymers and detection for the presence of chimeras by UChime.

16s rRNA Sequencing Data Analysis

The resulting sequences were classified against the Greengenes database and annotated with deepest level taxa represented by pseudo-bootstrap confidence scores of at least 80% averaged over 1,000 iterations of the naive Bayesian classifier. Any sequences that were classified as either being originated from archaea, eukarya, chloroplasts, mitochondria, or unknown kingdoms, were removed. The annotated sequences were assigned to phylotypes according to their consensus taxonomy with which at least 80% of the sequences agreed. Closed reference operational taxonomic units (OTUs) sharing 97% identity were clustered as well and assigned taxonomy according to the Greengenes database. Lefse analysis was performed to define bacterial taxa associated with CDI and healthy controls. The relative abundance of these abundance-differential taxa identified by Lefse in pre-FMT baseline samples and post-FMT last follow-up samples were plotted using pheatmap R package.

Example 2: Fecal Viral Preparation is Effective in Treating CDI in Mice

Methods

Fecal Viral Preparation (FVP)

Fecal viral preparation was prepared from pulverized human stool. Approximately 5 g of stool was suspended in 1 ml PBS buffer by vortexing for 5 min. Stool suspensions were then cleared by centrifugation at 1,500×g for 3 min to remove debris and cells. Clarified suspensions were sequentially passed through 100 µm, 0.45 µm and 0.22 µm filters to remove residual host and bacterial cells.

Animal Experiment

Studies were conducted on 4- to 6-week old female C57BL/6 that were reared in groups of 9. Individual mice were randomized after arrival. Mice were given an antibiotic cocktail of kanamycin (0.4 mg/mL), gentamicin (0.035 mg/mL), colistin (850 U/mL), metronidazole (0.215 mg/mL), and vancomycin (0.045 mg/mL) (all antibiotics were purchased from Sigma-Aldrich, St. Louis, Mo.) in their drinking water for 3 days. Mice were then given 2 days of recovery before administration of $10^7$ spores of C. difficile in PBS via oral gavage. On day 2 post C. difficile challenge, human fecal viral preparation was infused into CDI recipient mice through oral gavage. C. difficile load was monitored for the following one month by quantitative PCR on the toxin A gene of C. difficile.

Results

Figure 16:
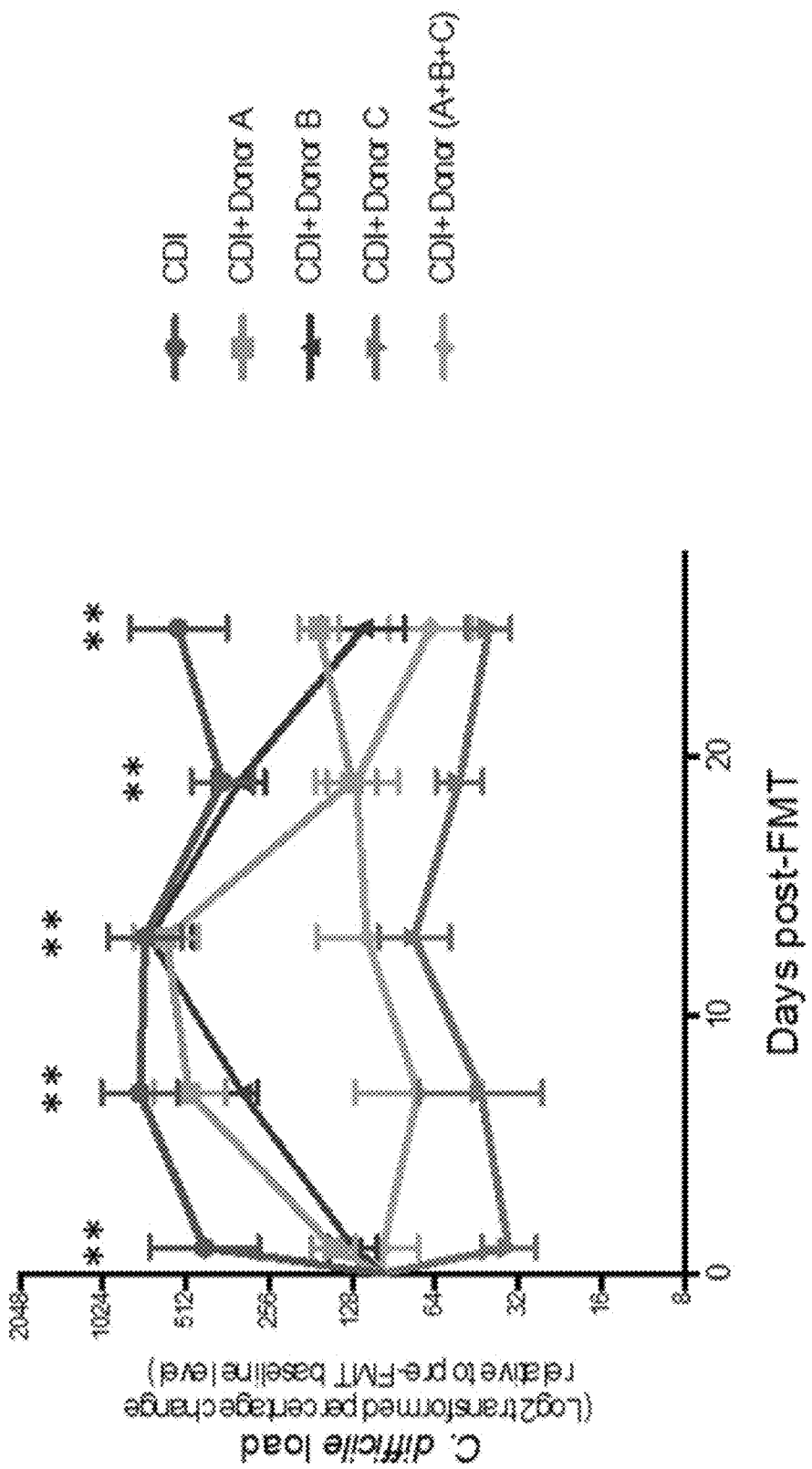
FIG. 16 *C. difficile* load alterations after FMT. *C. difficile* load was determined by quantitative PCR on the toxin A gene of *C. difficile*. *C. difficile* load was compared between CDI group and each donor FVP infusion group at each time point. **p<0.01, Mann-whitney test.

All donor FVPs including that from individual donors, donor A, B, C and pooled donor FVP, showed prompt C. difficile decreases on Day 1 post FMT, indicating Fecal viral preparation was effective in eliminating C. difficile. Mice infused with FVPs from Donor C and pooled donors (Donor A+B+C) showed persist low levels of C. difficile load after FMT, indicating a pooled donor FVP (higher Caudovirales richness than that of individual donor) was more likely to be superior than individual donors, A and B, in treating CDI (FIG. 16).

All patents, patent applications, and other publications, including GenBank Accession Numbers, cited in this application are incorporated by reference in the entirety for all purposes.

TABLE 1

Clinical characteristics and outcomes of subjects who received FMT or vancomycin For *Clostridium difficile* infections

| Subject | Sex | Age | Smoking | Severe/moderate | Duration of follow-up (weeks) | Outcome (till last follow-up) |
|---|---|---|---|---|---|---|
| FMT1 | M | 80 | Ex-smoker | Moderate | 16 | Cured |
| FMT2 | M | 52 | No | Severe | 27 | Cured |
| FMT3 | M | 38 | No | Moderate | 17 | Cured |
| FMT4 | F | 76 | No | Moderate | 18 | Cured |
| FMT5 | M | 63 | No | Severe | 18 | Cured |
| FMT6 | M | 88 | No | Severe | 23 | Cured |
| FMT7 | M | 45 | Ex-smoker | Severe | 20 | Recurrence at week 19 |
| FMT8 | F | 89 | No | Moderate | 11 | Recurrence at week 5 |
| FMT9 | F | 38 | No | Severe | 28 | Recurrence at week 28 |
| STD1 | M | 88 | Ex-smoker | Severe | 20 | Recurrence at week 12 |
| STD2 | M | 93 | No | Moderate | 7 | Recurrence at week 7 |
| STD3 | F | 78 | Smoker | Severe | 14 | Cured |
| STD4 | F | 83 | No | Severe | 17 | Cured |
| STD5 | F | 99 | No | Moderate | 26 | Cured |

FMT, faecal microbiota transplantation;
STD, standard therapy (vancomycin).

Results

TABLE 2

Summary of study subjects and samples

| sample# | sample_NAME | Sample_collection | time_point_post_FMT (week) | time_point_post_standard_therapy (week) | baseline_comparasion | FMT_number | LABEL | Time of sample collection | Household (famiy_ID) | Age | Sex |
|---|---|---|---|---|---|---|---|---|---|---|---|
| 1 | C1W0 | cross-sectional | NA | NA | CDI | NA | A0198ST1 | 19-Jan-15 | A | 86 | F |
| 2 | N1W0 | cross-sectional | NA | NA | Control | NA | A0222ST1 | 04-Mar-15 | A | | |
| 3 | C2W0 | cross-sectional | NA | NA | CDI | NA | A0393ST2 | 26-Nov-15 | C | | |
| 4 | N2W0 | cross-sectional | NA | NA | Control | NA | A0417ST1 | 11-Dec-15 | C | | |
| 5 | C3W0 | cross-sectional | NA | NA | CDI | NA | A0300ST1 | 24-Jul-15 | J | 80 | F |
| 6 | N3W0 | cross-sectional | NA | NA | Control | NA | A0297ST1 | 21-Jul-15 | J | 55 | F |
| 7 | C4W0 | cross-sectional | NA | NA | CDI | NA | A0345ST1 | 31-Aug-15 | M | 66 | F |
| 8 | N4W0 | cross-sectional | NA | NA | Control | NA | A0339ST1 | 26-Aug-15 | M | 41 | M |
| 9 | F10W0 | longitudinal | NA | NA | CDI | NA | A0347ST1 | 07-Sep-15 | O | 84 | M |
| 10 | D10W0 | cross-sectional | NA | NA | Control | NA | A0348ST1 | 08-Sep-15 | O | 42 | M |
| 11 | C6W0 | cross-sectional | NA | NA | CDI | NA | A0374ST1 | 08-Oct-15 | S | 76 | M |
| 12 | C5W0 | cross-sectional | NA | NA | CDI | NA | A0419ST1 | 11-Dec-15 | U | 25 | F |
| 13 | N5W0 | cross-sectional | NA | NA | Control | NA | A0424ST1 | 24-Dec-15 | U | 33 | M |
| 14 | N6W0 | cross-sectional | NA | NA | Control | NA | A0407ST1 | 26-Jan-16 | V | 45 | F |
| 15 | N7W0 | cross-sectional | NA | NA | Control | NA | A0189ST1 | 23-Dec-15 | W | 56 | F |
| 16 | N8W0 | cross-sectional | NA | NA | Control | NA | A0436ST1 | 08-Jan-16 | X | 36 | F |
| 17 | N9W0 | cross-sectional | NA | NA | Control | NA | A00448ST1 | 22-Jan-16 | Y | 43 | F |
| 18 | N10W0 | cross-sectional | NA | NA | Control | NA | A0454ST1 | 27-Jan-16 | Z | 85 | F |
| 19 | C7W0 | cross-sectional | NA | NA | CDI | NA | A0435ST1 | 07-Jan-16 | AA | 81 | M |
| 20 | C8W0 | cross-sectional | NA | NA | CDI | NA | A0438ST1 | 15-Jan-16 | Y | 99 | M |
| 21 | C9W0 | cross-sectional | NA | NA | CDI | NA | A0445ST1 | 21-Jan-16 | Z | | |
| 22 | N11W0 | cross-sectional | NA | NA | Control | NA | A0408ST1 | 26-Jan-16 | AB | 45 | F |

TABLE 2-continued

Summary of study subjects and samples

| sample# | sample_NAME | Sample_collection | time_point_post_FMT (week) | time_point_post_standard_therapy (week) | baseline_comparasion | FMT_number | LABEL | Time of sample collection | Household (famiy_ID) | Age | Sex |
|---|---|---|---|---|---|---|---|---|---|---|---|
| 23 | F1W0 | longitudinal | 0 | NA | CDI | FMT1 | A0394ST1 | 27-Oct-15 | B | | |
| 24 | F1W2 | longitudinal | 2 | NA | NA | FMT1 | A0394ST2 | 16-Nov-15 | B | | |
| 25 | F1W6 | longitudinal | 6 | NA | NA | FMT1 | A0394ST3 | 14-Dec-15 | B | | |
| 26 | D1W0 | cross-sectional | 0 | NA | Control | Donor 1 | A0392ST1 | 27-Oct-15 | B | | |
| 27 | F2W0 | longitudinal | 0 | NA | CDI | FMT2 | A0214ST1 | 13-Feb-15 | D | 52 | M |
| 28 | F2W2 | longitudinal | 2 | NA | NA | FMT2 | A0214ST2 | 06-Mar-15 | D | 52 | M |
| 29 | F2W4 | longitudinal | 4 | NA | NA | FMT2 | A0214ST5 | 20-Mar-15 | D | 52 | M |
| 30 | F2W27 | longitudinal | 27 | NA | NA | FMT2 | A0214ST7 | 28-Aug-15 | D | 52 | M |
| 31 | D2W0 | cross-sectional | 0 | NA | Control | Donor 2 | A0213ST1 | 12-Feb-15 | D | 51 | F |
| 32 | F3W0 | longitudinal | 0 | NA | CDI | FMT3 | A0228ST1 | 20-Mar-15 | F | 38 | F |
| 33 | F3W2 | longitudinal | 2 | NA | NA | FMT3 | A0228ST2 | 14-Apr-15 | F | 38 | F |
| 34 | F3W4 | longitudinal | 4 | NA | NA | FMT3 | A0228ST3 | 28-Apr-15 | F | 38 | F |
| 35 | F3W10 | longitudinal | 10 | NA | NA | FMT3 | A0228ST4 | 02-Jun-15 | F | 38 | F |
| 36 | F3W17 | longitudinal | 17 | NA | NA | FMT3 | A0228ST6 | 28-Jul-15 | F | 38 | F |
| 37 | D3W0 | cross-sectional | 0 | NA | Control | Donor 3 | A0229ST1 | 20-Mar-15 | F | 73 | M |
| 38 | F4W0 | longitudinal | 0 | NA | CDI | FMT4 | A0271ST1 | 03-Jun-15 | H | 76 | F |
| 39 | F4W2 | longitudinal | 2 | NA | NA | FMT4 | A0271ST2 | 29-Jun-15 | H | 76 | F |
| 40 | F4W4 | longitudinal | 4 | NA | NA | FMT4 | A0271ST3 | 06-Jul-15 | H | 76 | F |
| 41 | F4W5 | longitudinal | 5 | NA | NA | FMT4 | A0271ST4 | 13-Jul-15 | H | 76 | F |
| 42 | F4W10 | longitudinal | 10 | NA | NA | FMT4 | A0271ST6 | 20-Aug-15 | H | 76 | F |
| 43 | F4W18 | longitudinal | 18 | NA | NA | FMT4 | A0271ST7 | 16-Oct-15 | H | 76 | F |
| 44 | D4W0 | cross-sectional | 0 | NA | Control | Donor 4 | A0265ST1 | 01-Jun-15 | H | 53 | F |
| 45 | F5W0 | longitudinal | 0 | NA | CDI | FMT5 | A0310ST1 | 30-Jul-15 | K | 63 | M |
| 46 | F5W2 | longitudinal | 2 | NA | NA | FMT5 | A0310ST2 | 18-Aug-15 | K | 63 | M |
| 47 | F5W10 | longitudinal | 10 | NA | NA | FMT5 | A0310ST3 | 19-Oct-15 | K | 63 | M |
| 48 | F5W18 | longitudinal | 18 | NA | NA | FMT5 | A0310ST4 | 14-Dec-15 | K | 63 | M |
| 49 | D5W0 | cross-sectional | 0 | NA | Control | Donor 5 | A0313ST1 | 31-Jul-15 | K | 36 | F |
| 50 | F6W0 | longitudinal | 0 | NA | CDI | FMT6 | A0326ST1 | 21-Aug-15 | L | 88 | M |
| 51 | F6W2 | longitudinal | 2 | NA | NA | FMT6 | A0326ST2 | 17-Sep-15 | L | 88 | M |
| 52 | F6W4 | longitudinal | 4 | NA | NA | FMT6 | A0326ST3 | 01-Oct-15 | L | 88 | M |
| 53 | F6W11 | longitudinal | 11 | NA | NA | FMT6 | A0326ST4 | 20-Nov-15 | L | 88 | M |
| 54 | D6W0 | cross-sectional | 0 | NA | Control | Donor 6 | A0336ST1 | 24-Aug-15 | L | 41 | M |
| 55 | F7W0 | longitudinal | 0 | NA | CDI | FMT7 | A0340ST1 | 26-Aug-15 | N | 45 | M |
| 56 | F7W2 | longitudinal | 2 | NA | NA | FMT7 | A0340ST2 | 22-Sep-15 | N | 45 | M |
| 57 | F7W6 | longitudinal | 6 | NA | NA | FMT7 | A0340ST3 | 22-Oct-15 | N | 45 | M |
| 58 | F7W10 | longitudinal | 10 | NA | NA | FMT7 | A0340ST4 | 18-Nov-15 | N | 45 | M |
| 59 | D7W0 | cross-sectional | 0 | NA | Control | Donor 7 | A0346ST1 | 02-Sep-15 | N | 21 | M |

TABLE 2-continued

Summary of study subjects and samples

| sample# | sample_NAME | Sample_collection | time_point_post_FMT (week) | time_point_post_standard_therapy (week) | FMT_number | LABEL | Time of sample collection | Household (famiy_ID) | Age | Sex |
|---|---|---|---|---|---|---|---|---|---|---|
| 60 | F8W0 | longitudinal | 0 | NA | FMT8 | A0373ST1 | 30-Sep-15 | Q | 83 | F |
| 61 | F8W2 | longitudinal | 2 | NA | FMT8 | A0373ST2 | 18-Oct-15 | Q | 83 | F |
| 62 | F8W4 | longitudinal | 4 | NA | FMT8 | A0373ST3 | 04-Nov-15 | Q | 83 | F |
| 63 | D8W0 | cross-sectional | 0 | NA | Donor 8 | A0370ST1 | 25-Sep-15 | Q | 57 | M |
| 64 | F9W0 | longitudinal | 0 | NA | FMT9 | A0371ST1 | 24-Sep-15 | R | 38 | F |
| 65 | F9W2 | longitudinal | 2 | NA | FMT9 | A0371ST2 | 19-Oct-15 | R | 38 | F |
| 66 | F9W4 | longitudinal | 4 | NA | FMT9 | A0371ST3 | 05-Nov-15 | R | 38 | F |
| 67 | F9W10 | longitudinal | 10 | NA | FMT9 | A0371ST4 | 28-Dec-15 | R | 38 | F |
| 68 | S1W0 | longitudinal | NA | 0 | ST1 | A0223ST1 | 06-Mar-15 | E | 88 | M |
| 69 | S1W2 | longitudinal | NA | 2 | ST1 | A0223ST2 | 18-Mar-15 | E | 88 | M |
| 70 | S1W5 | longitudinal | NA | 5 | ST1 | A0223ST3 | 11-Apr-15 | E | 88 | M |
| 71 | S1W10 | longitudinal | NA | 10 | ST1 | A0223ST4 | 05-May-15 | E | 88 | M |
| 72 | S2W0 | longitudinal | NA | 0 | ST2 | A0256ST1 | 07-May-15 | G | 93 | M |
| 73 | S2W2 | longitudinal | NA | 2 | ST2 | A0256ST2 | 22-May-15 | G | 94 | F |
| 74 | S3W0 | longitudinal | NA | 0 | ST3 | A0293ST1 | 14-Jul-15 | I | 78 | F |
| 75 | S3W2 | longitudinal | NA | 2 | ST3 | A0293ST2 | 24-Jul-15 | I | 78 | F |
| 76 | S3W4 | longitudinal | NA | 4 | ST3 | A0293ST3 | 10-Aug-15 | I | 78 | F |
| 77 | S4W0 | longitudinal | NA | 0 | ST4 | A0369ST1 | 24-Sep-15 | P | 83 | F |
| 78 | S4W2 | longitudinal | NA | 2 | ST4 | A0369ST2 | 05-Oct-15 | P | 84 | F |
| 79 | S4W4 | longitudinal | NA | 4 | ST4 | A0369ST3 | 19-Oct-15 | P | 85 | F |
| 80 | S4W10 | longitudinal | NA | 10 | ST4 | A0369ST4 | 30-Nov-15 | P | 86 | F |
| 81 | S5W0 | longitudinal | NA | 0 | ST5 | A0376ST1 | 20-Oct-15 | T | 99 | F |
| 82 | S5W2 | longitudinal | NA | 2 | ST5 | A0376ST2 | 02-Nov-15 | T | 99 | F |
| 83 | S5W4 | longitudinal | NA | 4 | ST5 | A0376ST3 | 16-Nov-15 | T | 99 | F | baseline_comparasion column:
60: CDI, 61: NA, 62: NA, 63: Control, 64: CDI, 65: NA, 66: NA, 67: NA, 68: CDI, 69: NA, 70: NA, 71: CDI, 72: NA, 73: NA, 74: CDI, 75: NA, 76: NA, 77: CDI, 78: NA, 79: NA, 80: NA, 81: CDI, 82: NA, 83: NA

TABLE 3

Read Statistics for VLPs metagenomic sequencing data

| sample_number | stratege | Clean Reads (with duplicates) | Raw Data (bp) | Clean Data (bp) | Clean Data/Raw Data (%) | Q20 (%) |
|---|---|---|---|---|---|---|
| C1W0 | PE | 62775238 | 9991197000 | 9416285700 | 94.25 | 97.68 |
| N1W0 | PE | 61051824 | 9771340800 | 9157773600 | 93.72 | 97.66 |
| F1W0 | PE | 72908524 | 11628734400 | 10936278600 | 94.05 | 97.73 |
| F1W2 | PE | 61452336 | 9879645900 | 9217850400 | 93.30 | 97.64 |
| F1W6 | PE | 61937734 | 9901291200 | 9290660100 | 93.83 | 97.47 |
| D1W0 | PE | 71971260 | 11632557300 | 10795689000 | 92.81 | 97.56 |
| C2W0 | PE | 54404614 | 8603408400 | 8160692100 | 94.85 | 97.78 |
| N2W0 | PE | 58876302 | 9679518800 | 8831445300 | 91.24 | 96.99 |
| F2W0 | PE | 63222294 | 9483344100 | 9483344100 | 93.22 | 97.24 |
| F2W2 | PE | 57069572 | 9181378500 | 8560435800 | 93.24 | 97.44 |
| F2W4 | PE | 56474014 | 9258392400 | 8471102100 | 91.50 | 97.35 |
| F2W27 | PE | 62855360 | 9951258600 | 9428304000 | 94.74 | 97.58 |
| D2W0 | PE | 65188562 | 10492993800 | 9778284300 | 93.19 | 97.50 |
| S1W0 | PE | 78560738 | 12704849100 | 11784110700 | 92.75 | 96.61 |
| F3W0 | PE | 63633346 | 10132440000 | 9545001900 | 94.20 | 97.70 |
| F3W2 | PE | 67863116 | 11041764600 | 10179467400 | 92.19 | 97.17 |
| F3W4 | PE | 54546192 | 8841385200 | 8181928800 | 92.54 | 97.62 |
| F3W10 | PE | 56402642 | 9026390400 | 8460396300 | 93.73 | 97.51 |
| F3W17 | PE | 57655702 | 9308481600 | 8648355300 | 92.91 | 97.28 |
| D3W0 | PE | 60398538 | 9677539500 | 9059780700 | 93.62 | 97.57 |
| S2W0 | PE | 62029898 | 9921949800 | 9304484700 | 93.78 | 97.22 |
| F4W0 | PE | 70249768 | 11417761500 | 10537465200 | 92.29 | 97.19 |
| F4W2 | PE | 72291124 | 11593675200 | 10843668600 | 93.53 | 97.28 |
| F4W4 | PE | 55309580 | 9022624200 | 8296437000 | 92.78 | 97.05 |
| F4W5 | PE | 56341336 | 9447712200 | 8451200400 | 89.45 | 96.52 |
| F4W10 | PE | 67820766 | 10802030400 | 10173114900 | 94.18 | 97.26 |
| F4W18 | PE | 62542160 | 10187530200 | 9381324000 | 92.91 | 97.21 |
| D4W0 | PE | 65414574 | 10647087300 | 9812186100 | 92.98 | 97.22 |
| S3W0 | PE | 49856060 | 8095937400 | 7478409000 | 93.20 | 97.34 |
| C3W0 | PE | 52795414 | 8536192800 | 7919312100 | 93.60 | 97.61 |
| N3W0 | PE | 67781664 | 10971849600 | 10167249600 | 92.67 | 96.97 |
| F5W0 | PE | 59464284 | 9818251800 | 8919642600 | 91.67 | 96.84 |
| F5W2 | PE | 58990474 | 9742672200 | 8848571100 | 91.64 | 96.78 |
| F5W10 | PE | 70767788 | 11524117200 | 10615168200 | 92.94 | 97.47 |
| F5W18 | PE | 56344752 | 9110928000 | 8451712800 | 92.76 | 97.39 |
| D5W0 | PE | 56276446 | 9212273400 | 8441466900 | 92.45 | 97.21 |
| F6W0 | PE | 66880946 | 10848952800 | 10032141900 | 92.47 | 97.62 |
| F6W2 | PE | 49343280 | 8023825500 | 7401492000 | 93.08 | 97.27 |
| F6W4 | PE | 68396004 | 11080149600 | 10259400600 | 92.59 | 97.62 |
| F6W11 | PE | 59587740 | 9505559700 | 8938161000 | 94.03 | 97.56 |
| D6W0 | PE | 71249914 | 11956911900 | 10687487100 | 89.38 | 96.18 |
| C4W0 | PE | 64764190 | 10604839500 | 9714628500 | 92.42 | 96.93 |
| N4W0 | PE | 68626222 | 10919059800 | 10293933200 | 94.27 | 97.78 |
| F7W0 | PE | 60637808 | 10019179800 | 9095671200 | 90.78 | 96.77 |
| F7W2 | PE | 53007420 | 8590338300 | 7951113000 | 92.56 | 97.27 |
| F7W6 | PE | 60265864 | 9626333100 | 9039879600 | 93.91 | 97.88 |
| F7W10 | PE | 55566500 | 8885519700 | 8334975000 | 93.80 | 97.60 |
| D7W0 | PE | 63959224 | 10260963600 | 9593883600 | 93.50 | 97.43 |
| F8W0 | PE | 60709794 | 9837748800 | 9106469100 | 92.57 | 96.88 |
| F8W10 | PE | 67005004 | 10768592400 | 10050750600 | 93.33 | 97.41 |
| D8W0 | PE | 54733124 | 8822077200 | 8209968600 | 93.06 | 97.39 |
| S4W0 | PE | 52048562 | 8311757400 | 7807284300 | 93.93 | 97.48 |
| F8W0 | PE | 55373256 | 8896104000 | 8305988400 | 93.37 | 97.58 |
| F8W2 | PE | 52773494 | 8419165500 | 7916024100 | 94.02 | 97.62 |
| F8W4 | PE | 62692276 | 10020003000 | 9403841400 | 93.85 | 97.37 |
| D8W0 | PE | 54325118 | 8650715100 | 8148767700 | 94.20 | 97.68 |
| F9W0 | PE | 57743068 | 9351227700 | 8661460200 | 92.62 | 97.17 |
| F9W2 | PE | 62521482 | 10080941400 | 9378222300 | 93.03 | 97.51 |
| F9W4 | PE | 55870900 | 9226278600 | 8380635000 | 90.83 | 95.38 |
| F9W10 | PE | 55794488 | 9027887700 | 8369173200 | 92.70 | 97.11 |
| C6W0 | PE | 50764752 | 8176121400 | 7614712800 | 93.13 | 97.38 |
| S5W0 | PE | 59301276 | 9633133200 | 8895191400 | 92.34 | 97.12 |
| C5W0 | PE | 67889284 | 10923227100 | 10183392600 | 93.23 | 97.56 |
| N5W0 | PE | 59708564 | 9509021700 | 8956284600 | 94.19 | 97.63 |

TABLE 3-continued

Read Statistics for VLPs metagenomic sequencing data

| | | | | | | |
|---|---|---|---|---|---|---|
| N6W0 | PE | 62723994 | 10067253900 | 9408599100 | 93.46 | 97.62 |
| N7W0 | PE | 59306006 | 9430123200 | 8895900900 | 94.33 | 97.58 |
| N8W0 | PE | 65684456 | 10506488100 | 9852668400 | 93.78 | 97.81 |
| N9W0 | PE | 63649198 | 10202578800 | 9547379700 | 93.58 | 97.39 |
| N10W0 | PE | 50235066 | 8120349600 | 7535259900 | 92.79 | 97.37 |
| C7W0 | PE | 66179220 | 10552657800 | 9926883000 | 94.07 | 97.45 |
| C8W0 | PE | 64891662 | 10394203500 | 9733749300 | 93.65 | 97.57 |
| C9W0 | PE | 58954002 | 9377404800 | 8843100300 | 94.30 | 97.37 |
| N11W0 | PE | 62169334 | 10005166200 | 9325400100 | 93.21 | 97.46 |

| sample_number | Insert Size | Read Length (bp) | Clean Reads (deduplicates) | Clean Data (bp) | dehuman contamination clean reads |
|---|---|---|---|---|---|
| C1W0 | 270 | 150 | 35310274 | 5296541100 | 35259895 |
| N1W0 | 270 | 150 | 35174258 | 5276138700 | 35138622 |
| F1W0 | 270 | 150 | 49258666 | 7388799900 | 49214972 |
| F1W2 | 270 | 150 | 37950160 | 5692524000 | 37877002 |
| F1W6 | 270 | 150 | 36773522 | 5516028300 | 36694663 |
| D1W0 | 270 | 150 | 60530028 | 9079504200 | 60156905 |
| C2W0 | 270 | 150 | 30454726 | 4568208900 | 30429234 |
| N2W0 | 270 | 150 | 47090320 | 7063548000 | 46270650 |
| F2W0 | 270 | 150 | 47609728 | 7141459200 | 47383851 |
| F2W2 | 270 | 150 | 26486692 | 3973003800 | 26460992 |
| F2W4 | 270 | 150 | 31534626 | 4730193900 | 31385993 |
| F2W27 | 270 | 150 | 40976008 | 6146401200 | 40920048 |
| D2W0 | 270 | 150 | 47035814 | 7055372100 | 46771547 |
| S1W0 | 270 | 150 | 69986282 | 10497942300 | 61254628 |
| F3W0 | 270 | 150 | 44325384 | 6648807600 | 44226661 |
| F3W2 | 270 | 150 | 55736426 | 8360463900 | 55003416 |
| F3W4 | 270 | 150 | 19938070 | 2990710500 | 19912084 |
| F3W10 | 270 | 150 | 32904412 | 4935661800 | 32858523 |
| F3W17 | 270 | 150 | 51164390 | 7674658500 | 50799218 |
| D3W0 | 270 | 150 | 43593004 | 6538950600 | 43551379 |
| S2W0 | 270 | 150 | 19587122 | 2938068300 | 19481164 |
| F4W0 | 270 | 150 | 58701008 | 8805151200 | 53599900 |
| F4W2 | 270 | 150 | 42625764 | 6393864600 | 42189098 |
| F4W4 | 270 | 150 | 22071026 | 3310653900 | 21947324 |
| F4W5 | 270 | 150 | 37547642 | 5632146300 | 34620382 |
| F4W10 | 270 | 150 | 50790294 | 7618544100 | 49718303 |
| F4W18 | 270 | 150 | 52058076 | 7808711400 | 51790343 |
| D4W0 | 270 | 150 | 45517454 | 6827618100 | 45407834 |
| S3W0 | 270 | 150 | 27871988 | 4180798200 | 27649327 |
| C3W0 | 270 | 150 | 19745338 | 2961800700 | 19717506 |
| N3W0 | 270 | 150 | 48616360 | 7292454000 | 44963381 |
| F5W0 | 270 | 150 | 53191940 | 7978791000 | 50866340 |
| F5W2 | 270 | 150 | 52190752 | 7828612800 | 51029410 |
| F5W10 | 270 | 150 | 48194014 | 7229102100 | 48131665 |
| F5W18 | 270 | 150 | 48746752 | 7312012800 | 45555999 |
| D5W0 | 270 | 150 | 49072324 | 7360848600 | 48408340 |
| F6W0 | 270 | 150 | 33865442 | 5079816300 | 33828462 |
| F6W2 | 270 | 150 | 34613026 | 5191953900 | 34531700 |
| F6W4 | 270 | 150 | 50626182 | 7593927300 | 50483578 |
| F6W11 | 270 | 150 | 40184974 | 6027746100 | 39896849 |
| D6W0 | 270 | 150 | 63489090 | 9523363500 | 54552750 |
| C4W0 | 270 | 150 | 56952558 | 8542883700 | 56071573 |
| N4W0 | 270 | 150 | 45536348 | 6830452200 | 45429927 |
| F7W0 | 270 | 150 | 52360482 | 7854072300 | 51171286 |
| F7W2 | 270 | 150 | 45056108 | 6758416200 | 44968493 |
| F7W6 | 270 | 150 | 28086594 | 4212989100 | 28056380 |
| F7W10 | 270 | 150 | 32341864 | 4851279600 | 30309892 |
| D7W0 | 270 | 150 | 55051970 | 8257795500 | 54945617 |
| F8W0 | 270 | 150 | 52220104 | 7833015600 | 50666863 |
| F8W10 | 270 | 150 | 56329118 | 8449367700 | 56065034 |
| D8W0 | 270 | 150 | 43918160 | 6587724000 | 43793944 |
| S4W0 | 270 | 150 | 39097068 | 5864560200 | 38954427 |
| F8W0 | 270 | 150 | 36786824 | 5518023600 | 36710287 |
| F8W2 | 270 | 150 | 26959886 | 4043982900 | 26919104 |
| F8W4 | 270 | 150 | 34653832 | 5198074800 | 34607286 |
| D8W0 | 270 | 150 | 15930846 | 2389626900 | 15911391 |
| F9W0 | 270 | 150 | 50944548 | 7641682200 | 50758607 |
| F9W2 | 270 | 150 | 54102762 | 8115414300 | 53911905 |
| F9W4 | 270 | 150 | 51415752 | 7712362800 | 51140562 |
| F9W10 | 270 | 150 | 48465562 | 7269834300 | 48322767 |

TABLE 3-continued

| | | | | | |
|---|---|---|---|---|---|
| \multicolumn{6}{c}{Read Statistics for VLPs metagenomic sequencing data} |
| C6W0 | 270 | 150 | 32306284 | 4845942600 | 32272121 |
| S5W0 | 270 | 150 | 51022936 | 7653440400 | 50655870 |
| C5W0 | 270 | 150 | 57358300 | 8603745000 | 56812376 |
| N5W0 | 270 | 150 | 24030544 | 3604581600 | 23970287 |
| N6W0 | 270 | 150 | 54089868 | 8113480200 | 53257937 |
| N7W0 | 270 | 150 | 45422294 | 6813344100 | 45222130 |
| N8W0 | 270 | 150 | 28838700 | 4325805000 | 28687505 |
| N9W0 | 270 | 150 | 41104988 | 6165748200 | 39227638 |
| N10W0 | 270 | 150 | 33913816 | 5087072400 | 33631989 |
| C7W0 | 270 | 150 | 43113060 | 6466959000 | 31933029 |
| C8W0 | 270 | 150 | 48024320 | 7203648000 | 47357742 |
| C9W0 | 270 | 150 | 43761166 | 6564174900 | 43535848 |
| N11W0 | 270 | 150 | 33477790 | 5021668500 | 32776670 |

TABLE 4

Read Statistics for 16S rRNA sequencing data

| sample_number | length | raw_reads | raw_data (bp) | Raw_Q20 | Raw_Q30 | clean_data/raw_data | clean_reads | clean_data (bp) | Clean_Q20 | Clean_Q30 | GC_rate | GC(AT)_separation_rate |
|---|---|---|---|---|---|---|---|---|---|---|---|---|
| C1W0 | 250 | 93298 | 23324500 | 96.10; 92.98 | 93.82; 89.12 | 29.23 | 27272 | 6818000 | 90.95; 86.26 | 85.95; 79.43 | 54.54 | 18.93 |
| N1W0 | 250 | 127534 | 31883500 | 96.30; 90.93 | 94.05; 85.88 | 52.3 | 66694 | 16673500 | 94.68; 88.01 | 91.53; 81.50 | 55.41 | 19.19 |
| F1W0 | 250 | 139020 | 34755000 | 95.79; 90.83 | 93.15; 85.69 | 36.41 | 50614 | 12653500 | 91.85; 85.01 | 87.02; 76.95 | 54.77 | 17.07 |
| F1W2 | 250 | 453216 | 113304000 | 95.27; 90.75 | 92.40; 85.70 | 49.63 | 224930 | 56232500 | 92.95; 87.45 | 88.68; 80.73 | 55.19 | 18.81 |
| F1W6 | 250 | 210766 | 52691500 | 95.52; 90.53 | 92.45; 85.53 | 54.7 | 115298 | 28824500 | 93.84; 88.21 | 90.17; 81.93 | 54.43 | 18.58 |
| D1W0 | 250 | 197162 | 49290500 | 95.44; 90.44 | 92.62; 85.30 | 56.09 | 110582 | 27645500 | 93.87; 88.04 | 90.13; 81.74 | 53.81 | 17.97 |
| C2W0 | 250 | 115544 | 28886000 | 95.12; 84.81 | 91.98; 77.68 | 47.42 | 54786 | 13696500 | 93.25; 86.61 | 89.04; 79.19 | 55.67 | 18.71 |
| N2W0 | 250 | 192726 | 48181500 | 95.22; 86.64 | 92.12; 80.11 | 49.58 | 95562 | 23890500 | 93.50; 87.60 | 89.36; 80.64 | 55.47 | 18.54 |
| F2W0 | 250 | 145174 | 36293500 | 96.29; 91.93 | 93.94; 85.80 | 36.12 | 52432 | 13108000 | 92.64; 84.95 | 88.18; 76.72 | 56.19 | 17.67 |
| F2W2 | 250 | 165058 | 41264500 | 94.71; 92.06 | 91.46; 87.64 | 39.87 | 65806 | 16451500 | 91.65; 88.07 | 86.57; 81.70 | 53.31 | 16.39 |
| F2W4 | 250 | 157286 | 39321500 | 93.74; 89.94 | 89.79; 84.38 | 51.06 | 80306 | 20076500 | 92.01; 87.03 | 86.90; 79.90 | 55.57 | 17.8 |
| F2W27 | 250 | 166280 | 41570000 | 92.96; 89.93 | 88.53; 84.40 | 54.03 | 89846 | 22461500 | 91.33; 87.54 | 85.83; 80.71 | 55.26 | 17.98 |
| D2W0 | 250 | 178348 | 44587000 | 96.09; 91.21 | 93.73; 86.43 | 53.95 | 96226 | 24056500 | 94.52; 88.60 | 91.28; 82.59 | 53.59 | 17.7 |
| S1W0 | 250 | 144110 | 36027500 | 95.66; 89.74 | 92.89; 84.18 | 50.6 | 72918 | 18229500 | 93.52; 87.20 | 89.48; 80.29 | 54.66 | 18 |
| F3W0 | 250 | 392454 | 98113500 | 95.24; 90.96 | 92.45; 86.49 | 37.82 | 148440 | 37110000 | 91.53; 86.47 | 86.87; 79.95 | 51.66 | 17.84 |
| F3W2 | 250 | 230982 | 57745500 | 94.93; 91.76 | 91.83; 87.24 | 44.39 | 102532 | 25633000 | 92.27; 88.60 | 87.55; 82.49 | 54.01 | 17.61 |
| F3W4 | 250 | 112378 | 28094500 | 95.35; 91.60 | 92.47; 87.16 | 47.17 | 53006 | 13251500 | 93.19; 88.74 | 88.96; 82.86 | 53.36 | 18.24 |
| F3W10 | 250 | 230772 | 57693000 | 95.05; 91.29 | 93.05; 86.79 | 44.67 | 103090 | 25772500 | 92.61; 88.66 | 88.16; 82.79 | 52.81 | 17.76 |
| F3W17 | 250 | 311224 | 77806000 | 95.80; 90.74 | 93.16; 85.68 | 44.88 | 139674 | 34918500 | 93.46; 86.87 | 89.48; 79.89 | 54.17 | 17.5 |
| D3W0 | 250 | 523854 | 130963500 | 95.96; 91.67 | 93.55; 87.14 | 48.24 | 252724 | 63181000 | 93.84; 88.65 | 90.26; 82.68 | 53.82 | 17.61 |
| S2W0 | 250 | 141758 | 35439500 | 96.21; 91.31 | 93.89; 86.53 | 41.43 | 58734 | 14683500 | 93.30; 86.56 | 89.34; 79.61 | 54.25 | 17.83 |
| F4W0 | 250 | 174036 | 43509000 | 94.98; 91.93 | 91.98; 87.39 | 41.06 | 71452 | 17863000 | 91.59; 87.69 | 86.66; 81.07 | 54.33 | 17.79 |
| F4W2 | 250 | 220990 | 55247500 | 95.67; 90.72 | 92.87; 85.31 | 43.23 | 95524 | 23881000 | 92.80; 86.49 | 88.26; 78.96 | 55.18 | 17.57 |
| F4W4 | 250 | 241624 | 60406000 | 96.06; 92.31 | 93.65; 87.95 | 36.16 | 87376 | 21844000 | 92.41; 86.99 | 87.93; 80.09 | 55.01 | 17.9 |
| F4W5 | 250 | 180292 | 45073000 | 96.00; 88.58 | 93.18; 81.91 | 47.99 | 86526 | 21631500 | 93.76; 84.66 | 89.47; 75.90 | 58.15 | 18.24 |
| F4W10 | 250 | 170844 | 42711000 | 95.79; 89.19 | 93.05; 83.09 | 45.49 | 77718 | 19429500 | 93.10; 85.08 | 88.76; 76.93 | 56.41 | 19.63 |
| F4W18 | 250 | 201408 | 50352000 | 95.22; 90.83 | 92.19; 85.76 | 43.77 | 88154 | 22038500 | 91.86; 87.35 | 86.86; 80.61 | 54.42 | 17.76 |
| D4W0 | 250 | 421468 | 105367000 | 95.48; 91.52 | 92.80; 86.95 | 49.82 | 209980 | 52495000 | 93.28; 88.61 | 89.38; 82.63 | 53.83 | 18.38 |
| S3W0 | 250 | 127724 | 31931000 | 95.51; 90.51 | 92.80; 85.42 | 48.49 | 61934 | 15483500 | 93.12; 87.26 | 89.11; 80.65 | 53.3 | 18.06 |
| C3W0 | 250 | 186468 | 46617000 | 95.95; 91.35 | 93.48; 86.45 | 39.94 | 74474 | 18618500 | 92.77; 86.52 | 88.54; 79.29 | 54.38 | 18.5 |
| N3W0 | 250 | 253674 | 63418500 | 95.90; 90.49 | 93.47; 85.75 | 46.68 | 118412 | 29603000 | 93.54; 86.99 | 89.85; 80.72 | 51.69 | 17.47 |
| F5W0 | 250 | 141266 | 35316500 | 95.72; 92.24 | 93.29; 88.04 | 37.14 | 52462 | 13115500 | 92.29; 87.48 | 88.03; 81.02 | 53.82 | 17.02 |
| F5W2 | 250 | 144132 | 36033000 | 95.57; 92.50 | 93.00; 88.62 | 32.13 | 46310 | 11577500 | 90.82; 86.17 | 86.05; 79.34 | 53.24 | 17.31 |
| F5W10 | 250 | 218376 | 54594000 | 95.84; 90.75 | 93.41; 85.54 | 38.59 | 84272 | 21068000 | 92.46; 85.13 | 88.15; 77.47 | 54.1 | 17.83 |
| F5W18 | 250 | 238492 | 59623000 | 95.60; 91.57 | 92.89; 86.95 | 36.26 | 86488 | 21622000 | 91.76; 85.94 | 86.79; 78.68 | 53.76 | 17.52 |
| D5W0 | 250 | 350844 | 87711000 | 95.91; 91.00 | 93.44; 86.18 | 46.31 | 162472 | 40618000 | 93.40; 87.15 | 89.56; 80.42 | 54.36 | 18.42 |
| F6W0 | 250 | 266526 | 66631500 | 95.02; 92.91 | 92.15; 88.81 | 37.13 | 98972 | 24743000 | 90.92; 88.31 | 85.86; 81.84 | 54.74 | 16.86 |
| F6W2 | 250 | 236454 | 59113500 | 94.97; 87.97 | 91.90; 81.96 | 44.09 | 104262 | 26065500 | 92.28; 86.86 | 87.71; 79.83 | 53.8 | 17.56 |
| F6W4 | 250 | 147466 | 36866500 | 95.57; 91.03 | 92.91; 86.19 | 45.42 | 66978 | 16744500 | 93.05; 87.85 | 89.03; 81.39 | 53.98 | 17.64 |
| F6W11 | 250 | 233562 | 58390500 | 94.26; 91.59 | 90.82; 86.97 | 45.15 | 105462 | 26365500 | 90.98; 88.26 | 85.76; 81.91 | 54.06 | 17.48 |
| D6W0 | 250 | 305446 | 76361500 | 95.58; 90.07 | 92.80; 84.61 | 55.31 | 168944 | 42236000 | 93.98; 87.48 | 90.22; 80.72 | 54.78 | 18.24 |
| C4W0 | 250 | 168938 | 42234500 | 93.48; 91.86 | 89.78; 87.13 | 32.75 | 55330 | 13832500 | 87.80; 86.11 | 81.01; 78.38 | 54.64 | 16.78 |
| N4W0 | 250 | 356614 | 89153500 | 95.81; 91.21 | 93.14; 86.30 | 48.47 | 172844 | 43211000 | 93.53; 87.82 | 89.57; 81.25 | 54.23 | 17.68 |
| F7W0 | 250 | 283910 | 70977500 | 95.39; 91.97 | 92.67; 87.39 | 33.77 | 95884 | 23971000 | 90.79; 85.86 | 85.54; 78.32 | 55.08 | 18.15 |
| F7W2 | 250 | 200238 | 50059500 | 96.30; 92.38 | 94.04; 87.90 | 30.26 | 60588 | 15147000 | 91.65; 85.35 | 86.84; 77.46 | 55.17 | 18.01 |
| F7W6 | 250 | 170482 | 42620500 | 94.67; 92.70 | 91.49; 88.64 | 38.49 | 65614 | 16403500 | 90.65; 88.04 | 85.26; 81.81 | 54.36 | 17.75 |

TABLE 4-continued

Read Statistics for 16S rRNA sequencing data

| sample_number | length | raw_reads | raw_data (bp) | Raw_Q20 | Raw_Q30 | clean_data/ raw_data | clean_reads | clean_data (bp) | Clean_Q20 | Clean_Q30 | GC_rate | GC(AT)_separation_rate |
|---|---|---|---|---|---|---|---|---|---|---|---|---|
| F7W10 | 250 | 178994 | 44748500 | 93.84; 91.64 | 90.14; 86.78 | 36.65 | 65606 | 16401500 | 88.94; 86.33 | 82.46; 78.70 | 54.59 | 17.54 |
| D7W0 | 250 | 824186 | 206046500 | 95.85; 92.62 | 93.41; 88.60 | 40.69 | 335336 | 83834000 | 92.78; 88.86 | 88.76; 83.02 | 53.36 | 18.13 |
| F8W0 | 250 | 144894 | 36223500 | 96.49; 92.85 | 94.43; 88.97 | 27.61 | 39998 | 9999500 | 91.41; 85.43 | 86.62; 78.33 | 54.42 | 19.12 |
| F8W10 | 250 | 286358 | 71589500 | 95.20; 90.58 | 92.03; 85.16 | 49.98 | 143108 | 35777000 | 92.84; 87.39 | 88.32; 80.44 | 55.52 | 18.48 |
| D8W0 | 250 | 474850 | 118712500 | 94.68; 90.59 | 91.42; 85.26 | 50.34 | 239062 | 59765500 | 92.14; 87.42 | 87.45; 80.50 | 55.47 | 18.24 |
| S4W0 | 250 | 223636 | 55909000 | 95.97; 91.96 | 93.32; 87.20 | 31.94 | 71434 | 17858500 | 91.21; 85.22 | 85.78; 76.95 | 55.8 | 17.11 |
| F8W0 | 250 | 215272 | 53818000 | 94.62; 91.02 | 91.31; 86.15 | 42.74 | 92012 | 23003000 | 91.26; 86.45 | 86.01; 79.52 | 53.28 | 16.25 |
| F8W2 | 250 | 195352 | 48838000 | 95.40; 91.19 | 92.63; 86.51 | 44.86 | 87634 | 21908500 | 92.55; 87.56 | 85.23; 81.09 | 53.31 | 16.97 |
| F8W4 | 250 | 193674 | 48418500 | 95.84; 92.93 | 93.36; 88.86 | 29.48 | 57096 | 14274000 | 90.62; 86.02 | 85.33; 78.64 | 55.18 | 18.32 |
| D8W0 | 250 | 183434 | 45858500 | 93.90; 91.76 | 90.07; 86.93 | 47.41 | 86968 | 21742000 | 91.60; 88.79 | 86.38; 82.41 | 55.82 | 18.57 |
| F9W0 | 250 | 130132 | 32533000 | 96.33; 91.93 | 94.23; 87.95 | 28.16 | 36646 | 9161500 | 90.94; 83.79 | 86.02; 76.52 | 51.56 | 18.11 |
| F9W2 | 250 | 256932 | 64233000 | 94.64; 91.89 | 91.56; 87.57 | 47.87 | 122998 | 30749500 | 92.27; 88.76 | 87.79; 82.99 | 52.79 | 17.91 |
| F9W4 | 250 | 442748 | 110687000 | 95.87; 91.18 | 93.38; 86.58 | 38.11 | 168732 | 42183000 | 92.35; 85.88 | 87.97; 78.81 | 52.41 | 17.55 |
| F9W10 | 250 | 376794 | 94198500 | 95.75; 90.40 | 93.04; 85.16 | 44.61 | 168084 | 42021000 | 93.07; 86.18 | 88.81; 78.89 | 54.27 | 18.06 |
| C6W0 | 250 | 225218 | 56304500 | 95.78; 93.02 | 93.16; 88.78 | 28.02 | 63114 | 15778500 | 90.04; 85.79 | 84.32; 77.77 | 55.92 | 16.95 |
| S5W0 | 250 | 241924 | 60481000 | 95.83; 92.35 | 93.20; 87.91 | 32.86 | 79506 | 19876500 | 91.30; 86.11 | 86.02; 78.66 | 55.38 | 17.27 |
| C5W0 | 250 | 232140 | 58035000 | 95.60; 90.53 | 92.72; 84.82 | 36.89 | 85644 | 21411000 | 91.50; 84.58 | 86.25; 75.83 | 56.9 | 18.42 |
| N5W0 | 250 | 279832 | 69958000 | 95.29; 91.46 | 92.52; 86.79 | 57.13 | 159864 | 39966000 | 93.75; 89.41 | 90.13; 83.74 | 54.04 | 18.52 |
| N6W0 | 250 | 588188 | 147047000 | 95.50; 92.07 | 92.83; 87.77 | 49.31 | 290050 | 72512500 | 93.22; 89.13 | 89.38; 83.50 | 52.71 | 17.14 |
| N7W0 | 250 | 510334 | 127583500 | 95.87; 91.61 | 93.37; 87.05 | 50.07 | 255508 | 63877000 | 93.89; 88.61 | 90.30; 82.63 | 53.17 | 17.37 |
| N8W0 | 250 | 203468 | 50867000 | 93.42; 91.18 | 89.27; 86.35 | 50.32 | 102382 | 25595500 | 91.35; 88.52 | 85.82; 82.31 | 54.61 | 18.35 |
| N9W0 | 250 | 242486 | 60621500 | 94.36; 91.01 | 90.81; 85.96 | 58.72 | 142396 | 35599000 | 92.93; 89.03 | 88.49; 82.94 | 55.31 | 18.25 |
| N10W0 | 250 | 462154 | 115538500 | 95.48; 92.10 | 92.79; 87.83 | 48.56 | 224408 | 56102000 | 93.08; 89.09 | 89.09; 83.40 | 53.21 | 17.69 |
| C7W0 | 250 | 192778 | 48194500 | 96.05; 89.98 | 93.84; 84.79 | 45.56 | 87836 | 21959000 | 93.72; 86.32 | 90.25; 79.32 | 53.87 | 18.89 |
| C8W0 | 250 | 295522 | 73880500 | 96.32; 92.60 | 94.16; 88.49 | 35.97 | 106314 | 26578500 | 92.80; 87.26 | 88.75; 80.63 | 54.32 | 18.36 |
| C9W0 | 250 | 131878 | 32969500 | 96.16; 92.69 | 93.89; 88.70 | 26.67 | 35168 | 8792000 | 90.64; 84.74 | 85.32; 77.30 | 54.94 | 19.39 |
| N11W0 | 250 | 519884 | 129971000 | 95.94; 90.60 | 93.51; 85.62 | 52.17 | 271218 | 67804500 | 94.25; 87.82 | 90.90; 81.51 | 52.91 | 17.3 |

REFERENCES

1. Lessa F C, Winston L G, McDonald L C, et al. Burden of *Clostridium difficile* Infection in the United States REPLY. N Engl J Med 2015; 372:2369-70.
2. Khoruts A, Dicksved J, Jansson J K, et al. Changes in the composition of the human fecal microbiome after bacteriotherapy for recurrent *Clostridium difficile*-associated diarrhea. J Clin Gastroenterol 2010; 44:354-60.
3. van Nood E, Vrieze A, Nieuwdorp M, et al. Duodenal Infusion of Donor Feces for Recurrent *Clostridium difficile*. N Engl J Med 2013; 368:407-15.
4. Drekonja D, Reich J, Gezahegn S, et al. Fecal microbiota transplantation for *Clostridium difficile* infection a systematic eeview. Ann Intern Med 2015; 162:630-U230.
5. Lee C H, Steiner T, Petrof E O, et al. Frozen vs fresh fecal microbiota transplantation and clinical resolution of diarrhea in patients with recurrent *Clostridium difficile* infection a randomized clinical trial. Jama-J Am Med Assoc 2016; 315:142-9.
6. Khoruts A, Sadowsky M J. Therapeutic transplantation of the distal gut microbiota. Mucosal Immunol 2011; 4:4-7.
7. Manichanh C, Reeder J, Gibert P, et al. Reshaping the gut microbiome with bacterial transplantation and antibiotic intake. Genome Res 2010; 20:1411-19.
8. Rea M C, Dobson A, O'Sullivan O, et al. Effect of broad- and narrow-spectrum antimicrobials on *Clostridium difficile* and microbial diversity in a model of the distal colon. Proc Natl Acad Sci USA 2011; 108(Suppl 1):4639-44.
9. Barr J J, Auro R, Furlan M, et al. Bacteriophage adhering to mucus provide a non-host-derived immunity. Proc Natl Acad Sci USA 2013; 110:10771-6.
10. Duerkop B A, Clements C V, Rollins D, et al. A composite bacteriophage alters colonization by an intestinal commensal bacterium. Proc Natl Acad Sci USA 2012; 109:17621-6.
11. Reyes A, Wu M, McNulty N P, et al. Gnotobiotic mouse model of *phage*-bacterial host dynamics in the human gut. Proc Natl Acad Sci USA 2013; 110:20236-41.
12. Broecker F, Klumpp J, Schuppler M, et al. Long-term changes of bacterial and viral compositions in the intestine of a recovered *Clostridium difficile* patient after fecal microbiota transplantation. Mol Case Stud 2016; 2:a000448.
13. Chehoud C, Dryga A, Hwang Y, et al. Transfer of viral communities between human individuals during Fecal Microbiota rransplantation. MBio 2016; 7:e00322.
14. Broecker F, Klumpp J, Moelling K. Long-term microbiota and virome in a Zurich patient after fecal transplantation against *Clostridium difficile* infection. Ann N Y Acad Sci 2016; 1372:29-41.
15. Ott S J, Waetzig G H, Rehman A, et al. Efficacy of sterile fecal filtrate transfer for treating patients with *Clostridium difficile* infection. Gastroenterology 2017; 152:799-811.e7.
16. Broecker F, Russo G, Klumpp J, et al. Stable core virome despite variable microbiome after fecal transfer. Gut Microbes 2016:1-7.
17. Norman J M, Handley S A, Baldridge M T, et al. Disease-specific alterations in the enteric virome in inflammatory bowel disease. Cell 2015; 160:447-60.
18. Langmead B, Salzberg S L. Fast gapped-read alignment with Bowtie 2. Nat Methods 2012; 9:357-U54.
19. Bryson S J, Thurber A R, Correa A M S, et al. A novel sister clade to the enterobacteria microviruses (family Microviridae) identified in methane seep sediments. Environ Microbiol 2015; 17:3708-21.
20. Reyes A, Haynes M, Hanson N, et al. Viruses in the faecal microbiota of monozygotic twins and their mothers. Nature 2010; 466:334-U81.
21. Yang J Y, Kim M S, Kim E, et al. Enteric viruses ameliorate gut inflammation via toll-like receptor 3 and toll-like receptor 7-mediated interferon-beta production. Immunity 2016; 44:889-900.
22. Colman R J, Rubin D T. Fecal microbiota transplantation as therapy for inflammatory bowel disease: a systematic review and meta-analysis. J Crohns Colitis 2014; 8:1569-81.
23. De Leon L M, Watson J B, Kelly C R. Transient flare of ulcerative colitis after fecal microbiota transplantation for recurrent *Clostridium difficile* infection. Clin Gastroenterol H 2013; 11:1036-8.
24. Kelly C R, Kahn S A, Kashyap P. Update on fecal microbiota transplantation 2015: indications, methodologies, mechanisms, and outlook. Gastroenterology 2015; 149:223-37.
25. Virgin H W. The Virome in Mammalian Physiology and Disease. Cell 2014; 157:142-50.
26. Cortez M H, Weitz J S. Coevolution can reverse predator-prey cycles. Proc Natl Acad Sci USA 2014; 111:7486-91.
27. Thingstad T F. Elements of a theory for the mechanisms controlling abundance, diversity, and biogeochemical role of lytic bacterial viruses in aquatic systems. Limnol Oceanogr 2000; 45:1320-8.
28. Rodriguez-Valera F, Martin-Cuadrado A B, Rodriguez-Brito B, et al. OPINION Explaining microbial population genomics through *phage* predation. Nat Rev Microbiol 2009; 7:828-36.
29. Lim E S, Zhou Y J, Zhao G Y, Bauer I K, Droit L, Ndao I M, et al. Early life dynamics of the human gut virome and bacterial microbiome in infants. Nat Med 2015; 21:1228-+.
30. Schmieder R, Edwards R. Fast Identification and Removal of Sequence Contamination from Genomic and Metagenomic Datasets. PloS one 2011; 6.
31. Peng Y, Leung H C M, Yiu S M, Chin F Y L. IDBA—A Practical Iterative de Bruijn Graph De Novo Assembler. Lect N Bioinformat 2010; 6044:426-40.
32. Fu L M, Niu B F, Zhu Z W, Wu S T, Li W Z. CD-HIT: accelerated for clustering the next generation sequencing data. Bioinformatics 2012; 28:3150-2.
33. Delcher A L, Bratke K A, Powers E C, Salzberg S L. Identifying bacterial genes and endosymbiont DNA with Glimmer. Bioinformatics 2007; 23:673-9.
34. Hannigan G D, Meisel J S, Tyldsley A S, Zheng Q, Hodkinson B P, SanMiguel A J, et al. The Human Skin Double-Stranded DNA Virome: Topographical and Temporal Diversity, Genetic Enrichment, and Dynamic Associations with the Host Microbiome. mBio 2015; 6:e01578-15.
35. Minot S, Bryson A, Chehoud C, Wu G D, Lewis J D, Bushman F D. Rapid evolution of the human gut virome. Proceedings of the National Academy of Sciences of the United States of America 2013; 110:12450-5.
36. Schloss P D, Westcott S L, Ryabin T, Hall J R, Hartmann M, Hollister E B, et al. Introducing mothur: Open-Source, Platform-Independent, Community-Supported Software for Describing and Comparing Microbial Communities. Appl Environ Microb 2009; 75:7537-41.
37. McDonald D, Price M N, Goodrich J, Nawrocki E P, DeSantis T Z, Probst A, et al. An improved Greengenes taxonomy with explicit ranks for ecological and evolutionary analyses of bacteria and archaea. Isme J 2012; 6:610-8.

What is claimed is:

1. A method for assessing likelihood of effective fecal microbiota transplantation (FMT) for treating *Clostridium difficile* Infection, comprising determining Caudovirales richness or diversity in a stool sample obtained from a donor prior to FMT, wherein FMT is assessed as likely to be effective for a potential recipient when Caudovirales richness is greater than 400 (Chao1 richness index) or Caudovirales diversity is greater than 4 (Shannon's diversity index), and wherein FMT is assessed as unlikely to be effective for a potential recipient when Caudovirales richness is no greater than 400 (Chao1 richness index) or Caudovirales diversity (Shannon's diversity index) is no greater than 4.

2. The method of claim 1, wherein Caudovirales richness is greater than 400 (Chao1 richness index) or Caudovirales diversity is greater than 4 (Shannon's diversity index), and FMT is assessed as likely to be effective for a potential recipient.

3. The method of claim 2, further comprising performing FMT on the potential recipient.

4. The method of claim 3, further comprising determining Caudovirales richness or diversity in a stool sample obtained from the recipient after FMT.

5. The method of claim 1, wherein Caudovirales richness is no greater than 400 (Chao1 richness index) or Caudovirales diversity (Shannon's diversity index) is no greater than 4, and FMT is assessed as unlikely to be effective for a potential recipient.

6. The method of claim 1, further comprising determining Caudovirales richness or diversity in a stool sample obtained from a potential recipient prior to FMT.

7. The method of claim 6, wherein the donor's Caudovirales richness or Caudovirales diversity is greater than the potential recipient's Caudovirales richness or Caudovirales diversity, and FMT is assessed as likely to be effective for the potential recipient.

8. The method of claim 7, wherein the donor's Caudovirales richness or Caudovirales diversity is greater than the potential recipient's Caudovirales richness or Caudovirales diversity by at least 10%.

9. The method of claim 7, further comprising performing FMT on the potential recipient.

10. The method of claim 6, wherein donor's Caudovirales richness or Caudovirales diversity is no greater than the potential recipient's Caudovirales richness or Caudovirales diversity, and FMT is assessed as unlikely to be effective for the potential recipient.

11. The method of claim 1, wherein Caudovirales richness or diversity is determined in a first stool sample obtained from a first potential donor prior to FMT and in a second stool sample obtained from a second potential donor prior to FMT.

12. The method of claim 11, wherein the first potential donor has a lower Caudovirales richness or diversity than the second potential donor and is assessed to have a lower likelihood of being an appropriate donor for an effective FMT than the second potential donor.

13. The method of claim 12, further comprising performing FMT using fecal matter obtained from the second potential donor.

14. The method of claim 1, wherein Caudovirales richness or diversity is determined by quantitative polymerase chain reaction (PCR) or metagenomics sequencing.

* * * * *